(12) United States Patent
Hageman

(10) Patent No.: US 7,108,982 B1
(45) Date of Patent: Sep. 19, 2006

(54) DIAGNOSTICS AND THE THERAPEUTICS FOR MACULAR DEGENERATION

(75) Inventor: Gregory S. Hageman, Coralville, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/511,416

(22) Filed: Feb. 22, 2000

Related U.S. Application Data

(60) Provisional application No. 60/123,052, filed on Mar. 5, 1999, provisional application No. 60/120,668, filed on Feb. 19, 1999, provisional application No. 60/120,822, filed on Feb. 19, 1999.

(51) Int. Cl.
*G01N 33/53* (2006.01)
*C12Q 1/00* (2006.01)

(52) U.S. Cl. .......................................... 435/7.1; 435/4
(58) Field of Classification Search ................. 435/7.1, 435/4
See application file for complete search history.

(56) References Cited

U.S. PATENT DOCUMENTS

| 6,197,770 B1 * | 3/2001 | Natchus et al. .......... 514/238.2 |
| 2003/0149997 A1 | 8/2003 | Hageman et al. | |

FOREIGN PATENT DOCUMENTS

| WO | WO 94/01123 | | 1/1994 |
| WO | WO 95/17673 | A1 | 6/1995 |
| WO | WO 97/40849 | | 11/1997 |
| WO | WO 01/02866 | A1 | 1/2001 |
| WO | WO 01/06262 | A1 | 1/2001 |

OTHER PUBLICATIONS

G Chaine et al., Br F Ophthalmol, "Case-control study of the risk factors for age related macular degeneration," 1998;82:996-1002.*
JR Vingerling et al., American Journal of Epidemiology. "Age-related Macular Degeneration is Associated with Atherosclerosis," 1995, vol. 142, No. 4, pp. 404-409.*
Cobb et al, IOVS May 1997; 38:S354/1651.*
Bizbiz et al, Atherosclerosis 1997; 131:73-8.*
Nicoloff et al, Gen Pharmacol Aug. 2000;35:83-7.*
Fulop et al, Clin Physiol Biochem 1990;8:273-82.*
Kohner et al, Br Med Bull 1989;45:148-73.*
Klein et al, Ophthalmol 2003;110:1273-80.*
Grange JJ, et al., "Phthogenesis of abdominal aortic aneurysm: an update and look toward the future," Cardiovasc Surg, 5(3):256-65, 1997.
Gregory, et al., "Features of autoimmunity in the abdominal aortic aneurysm," Arc Surg, 131:85-88, 1996.
Guo, et al., "Matrix metalloproteinase and their inhibitors in vitreous in age-related macular degeneration and proliferative diabetic retinopathy" IOVS (Suppl) 38:S354, 1997.
He, et al., "The composition and mechanical properties of abdominal aortic aneurysm," J Vasc Surg, 20(1): 6-13 1994.
Hirose, H. et al., "Molecular cloning of the complementary DNA for an additional member of the family of aortic aneurysm antigenic proteins," J. Vasc. Surg. 26: 313-318, 1997.
Hirose, H., et al., "Genetic risk factor for abdominal aortic aneurysm: HLA-DR2(15), A Japanese study," J. Vasc. Surg. 27:500-503, 1998.
Holmes DR, et al., "Indomethacin prevents elastase-induced abdominal aortic aneurysms in the rat," J Surg Res, 63(1):305-9, 1996.
Holz, F., et al. "Analysis of lipid deposits extracted from human macular and peripheral bruch's membrane," Arch. Ophthalmol., 112, 402-406, 1994.
Keen RR, et al., "Interleukin-1 beta induces differential gene expression in aortic smooth muscle," J Vasc Surg, 20(5):774-86, 1994.
Koch, et al., Human abdominal aortic aneurysms, Am. J. Path., 137:1199-1213, 1990.
Kuivaniemi, et al., "Fibulin-2 exhibits high degree of variability, but no structural changes concordant with abdominal aortic aneurysm," Eur. J. Hum. Gen 6:642-646, 1998.
Kuivaniemi, H. et al., "Genetic causes of aortic aneurysms," J. Clin. Invest. 88:1441-1444, 1991.
Menashi, S., "Collagen in abdominal aortic aneurysm: typing, content, and degradation," J. Vasc. Surg., 578-582, 1987.
Minion DJ, et al., "Elastin is increased in abdominal aortic aneurysms," J Surg Res, 57(4):443-6, 1994.
Miralles M, et al., "Indomethacin inhibits expansion of experimental aortic aneurysms via inhibiting the cox2 isoform of cyclooxygenase," J Vasc Surg, 29(5):884-93, 1999.
Moore G, et al., "Suppression of experimental abdominal aortic aneurysms by systemic treatment with hydroxamate-based matrix metalloproteinase inhibitor (RS 132908)," J Vasc Surg, 20(3):522-32, 1999.

(Continued)

*Primary Examiner*—Q. Janice Li
(74) *Attorney, Agent, or Firm*—Townsend and Townsend and Crew LLP

(57) ABSTRACT

The invention relates to diagnostics and therapeutics and animal models for macular degeneration, specifically as they relate to the association described herein between macular degeneration and arterial wall disruptive disorders. In one embodiment, the invention provides kits and methods for diagnosing macular degeneration comprising identifying a marker for an arterial wall disruptive disorder, including an aneurysm. In one embodiment, the invention provides therapeutics for treating macular degeneration comprising delivering to a subject an agent useful for treating an arterial wall disruptive disorder, including an aneurysm.

7 Claims, No Drawings

OTHER PUBLICATIONS

Newman KM, et al., "Matrix metalloproteinases in abdominal aortic aneurysm: characterization, purification, and their possible sources," Connect Tissue Res, 30(4):265-76, 1994.

Newsome, D., et al., "Reaction of specific extracellular matrix molecules in drusens, bruch's membrane, and ciliary body," *Amer. J. Ophthalmol.,* 104, 373-381, 1987.

Ozsvath, K., et al., "Molecular mimicry in human aortic aneruysmal diseases," Annals NY Acad. Sci., 800:288-293, 1996.

Powell JT, et al., "Interaction between fibrillin genotype and blood pressure and the develop aneurysmal disease," Ann NY Acad Sci, 800(-HD-):198-207, 1996.

Rasmussen TE, et al., "Genetic risk factors in inflammatory abdominal aneurysms: polymorphic residue 70 in the HLA-DR B1 gene as a key genetic element," J Vasc Surg, 25(2):356-64, 1997.

Reilly, J. M., "Plasminogen activators in abdominal aortic aneurysmal disease," Annals NY Acad. Sci., 800:151-156, 1996.

Robert L, et al., "Elastin-elastase-atherosclerosis revisited," Atherosclerosis, 140(2):281-95, 1998.

Sacks, S.G. et al., "The pathogenesis of optic nerve drusen. A hypothesis," Archives of Ophthalmology 95(3), pp. 425-8, 1977.

Sakalihasan N, et al., "Activated forms of MMP2 and MMP9 in abdominal aortic aneurysms," J Vasc Surg, 24(1):127-33, 1996.

Sauvage M, et al., "Localization of elastin mRNA and TGF-beta in rat aorta and caudal artery as a function of age," Cell Tissue Res. 29:305-314, 1998.

Sobolewaski, K. et al., Act. Biocim. Polonica, 42:301-308, 1995.

Stanley JC et al., "Splanchnic and renal artery aneurysms," pp. 468-481 in WS Moore, *Vascular Surgery: A Comprehensive Review,* WB Saunders, 1998.

Starita, C., et al., Exp. Eye Res., 62, 565-572, 1996.

Allaire E, et al., "Local overexpression of TIMP-1 prevents aortic aneurysm degeneration an a rat model," J Clin Invest, 102(7), 1413-20, 1998.

Anidjar S, et al., "Experimental study of determinants of aneurysmal expansion of the abdomen," Ann Vasc Surg, 9(2), 127-36, 1994.

Aoyagi M, et al., "Smooth muscle cell proliferation, elastin formation, and tropoelastin transcripts during the development of intimal thickening in rabbit carotid arteries after endothelial denudation," Histochem Cell Biol 107:117, 1997.

Beckman, EN, "Plasma cell infiltrates in atherrosclerotic abdominal aortic aneurysms," AM. J. Clin. Pathol., 85:21-24, 1986.

Bigatel DA, et al., "The matrix metalloproteinase inhibitor BB-94 limits expansion of experimental abdominal aortic aneurysms," J Vasc Surg, 29(1):130-8; discussion 138-9, 1999.

Bilato and Crow "Atherosclerosis and the vascular biology of aging." Aging 8(4):221-34, 1996.

Bobryshev, Y. V. et al., "Immunophenotypic analysis of the aortic aneursm wall suggests that vascular dendritic cells are involved in immune reponses," Cardiovascular Surgery, 6(3):240-249, 1998.

Boyle JR, et al., "Amlodipine potentiates metalloproteinase activity and accelerates elastin degradation in a model of aneurysmal disease," Eur J Vasc Endovasc Surg, 16(5):408-14, 1998.

Boyle JR, et al., "Doxycycline inhibits elastin degradation and reduces metalloproteinase activity in a model of aneurysmal disease," J Vasc Surg, 27(2):354-61, 1998.

Brophy, CM et al., "The role of inflammmation in nonspecific abdomonal aortic aneurysm disease," Annals Vasc. Surg., 5:229-233, 1991.

Brophy, CM et al., "Decreased tissue inhibitor of metalloproteinases (TIMP) in abdominal aortic aneurysm tissue: a preliminary report," J Surg Research 50:653-657, 1991.

Buckmaster MJ, et al., "Source of elastin-degrading enzymes in mycotic aortic aneurysms: bacterial or inflammatory response?," Cardiovasc Surg, 71:16-26, 1999.

Campa, "Elastin degradation in abdominal aortic aneurysms," JS, Athersclerosis 65:13-21, 1987.

Capella, et al. "Complement activation and subclassification of tissue immunoglobin G in the abdominal aortic aneurysm," (J. Surg. Research 65:31-33, 1996.

Cattell MA, et al., "Increased elastin content and decreased elastin concentration may be predictive factors in dissecting aneurysms of human thoracic aorta," Cardiovasc Res, 27(2):176-81, 1993.

Cohen, et al., "α1-Antitrypsin phenotypes in patients with abdominal aortic aneurysms," J. Surg. Res. 49:319-321, 1990.

Cunningham, R.D. et al., "Aneurysm of the ophthalmic artery with drusen of the optic nerve head," American Journal Opthalmology, 72(4), pp. 743-745, 1971.

Curci JA, et al., "Expression and localization of macrophage elastase matrix metalloprotein abdominal aortic aneurysms," J Clin Invest, 102(11):1900-10, 1998.

Davis V, et al., "Matrix metalloproteinase-2 production and its binding to the matrix are in abdominal aortic aneurysms," Arterioscler Thromb Vasc Biol, 18(10):1625-33, 1998.

Elmore JR, et al., "Expression of matrix metalloproteinases and TIMPs in human abdominal aneurysms," Ann Vasc Surg, 12(3):221-8, 1998.

Feeney-Burns, L., and Ellersieck, M. "Age-related changes in the ultrastructure of bruch's membrane," Amer. J. Ophthalmol., 100, 686-697, 1985.

Gargiulo M, et al., "Content and turnover of extracellular matrix protein in human "nonspecific" inflammatory abdominal aortic aneurysms," Eur J Vasc Surg, 7(5):546-53, 1993.

Tamarina NA, et al., "Expression of matrix metalloproteinases and their inhibitors in aneurysms of the aorta," Surgery, 122(2):264-72, 1997.

Tamarina et al., "Proteoglycan gene expression is decreased in abdominal aortic aneurysms," J. Surg. Research 74:76-80, 1998.

Tarkkanen and Laatikainen,, "Late ocular manifestations in neonatalherpes simplex infection," Br. J. Ophthaloml., vol. 61, pp. 608-616, 1977.

Tromp, G. et al., "Sequencing of cDNA from 50 unrelated patients reveals that mutations in the triple-helical domain of type III procollagen are in infrequent cause of aortic aneurysms," J. Clin. Invest., 91:2539-2545, 1993.

Verloes, A., et al., "Aneurysms of the abdominal aorta: familial and genetic aspects in three hundred thirteen pedigrees," *J. Vasc. Surg.* 21:646-655, 1995.

Vine and Powell, "Metalloproteinases in degenerative aortic disease," Clinical Sci., 81:233-239, 1991.

Vingerling, J.R. et al., "Age related macular degeneration and smoking. The rotterdam study," Arch Phthalmol., vol. 114, No. 10, pp. 1193-1196, 1996.

Walton LJ, et al., "Inhibition of prostaglandin E2 synthesis in abdominal aortic aneruysms: implications for smooth muscle cell viability, inflammatory processes, and the expansion of abdominal aortic aneurysms," Circulation, 100(1):48-54, 1999.

White, et al., "Adventitial elastolysis in a primary event in aneurysm formation," J Vasc Surg, 17(2):371-81, 1993.

Xia, S et al., "Partial amino acid sequence of a novel 40-kDa human aortivc protein, with vitronectin-like, fibrinogen-like, and calcium binding domains: aortic aneurysm-associated protein-40 (AAAP-40) [human MAGP-3,proposed]," Biochem. Biophys. Research Communication, 219:36-39, 1996.

Anidjar, S. et al., "Elastase-induced experimental aneurysms in rats" Circulation, Sep. 1990, pp. 973-981, vol. 82, No. 3.

Cohen, J.R. et al. "Role of the neutrophil in abdominal aortic aneurysm development" Cardiovasc. Surg., Aug. 1993, pp. 373-376, vol. 1, No. 4.

Cohen, J.R. et al. "Urinary L-valyl proline in patients with aortic aneurysms" Surg. Gynecol. Obstet., Jun. 1989, pp. 507-512, vol. 168, No. 6.

Depalma, R.G. et al. "Approaches to evaluating regression of experimental atherosclerosis" Adv. Exp. Med. Biol., 1977, pp. 459-470, vol. 82.

Gineitis, A. et al. "Two-dimensional high-resolution electrophoresis of elastin-derived peptides" J. Chromatogr. B. Biomed. Sci. Appl., May 9, 1997, pp. 303-310, vol. 692, No. 2.

Goldberg, J. et al. "Factors associated with age-related macular degeneration. An analysis of data from the first National Health and Nutrition Examination Survey" Am J. Epidemiol., Oct. 1988, pp. 700-710, vol. 128, No. 4.

Hirvela, H. et al. "Risk factors of age-related maculopathy in a population 70 years of age or older" Ophthalmology, Jun. 1996, pp. 871-877, vol. 103, No. 6.

Hyman, L.G. et al. "Senile macular degeneration: a case-control study" Am. J. Epidemiol., Aug. 1983, pp. 213-227, vol. 118, No. 2.

Juvonen, T. et al. "Demonstration of a bioactive elastin-derived peptide (Val-Gly-Val-Ala-Pro-Gly) in vascular lesions characterized by the segmental destruction of media" Ann. Chir. Gynaecol., 1994, pp. 296-302, vol. 83, No. 4.

Juvonen, T. et al. "Segmented Mediolytic Arteritis-Electronmicroscopic and Immunohistochemical Study" Eur. J. Vasc. Surg., 1994, pp. 70-77, vol. 8.

Klein, R. et al. "Early age-related maculopathy in the cardiovascular health study" Opthalmology, Jan. 2003, pp. 25-33, vol. 110, No. 1.

Klein, R. et al. "Prevalence of age-related maculopathy in the Atherosclerosis Risk in Communities Study" Arch. Opthalmol., Sep. 1999, pp. 1203-1210, vol. 117, No. 9.

Klein, R. et al. "The relation of cardiovascular disease and its risk factors in the 5-year incidence of age-related maculopathy: the Beaver Dam Eye Study" Ophthalmology, Nov. 1997, pp. 1804-1812, vol. 104, No. 11.

Kuivaniemi, H. et al. "Candidate genes for abdominal aortic aneurysms" Ann. NY Acad. Sci., Nov. 1996, pp. 186-197, vol. 800.

Lindholt, J.S. et al, "Serum-elastin-peptides as a predictor of expansion of small abdominal aortic aneurysms" Eur. J. Vasc. Endovasc. Surg. Jul. 1997, pp. 12-16, vol. 14, No. 1.

Louwrens, H.D. et al. "Risk factors for the atherosclerosis in men with stenosing or aneurysmal disease of the abdominal aorta" Int. Angiol., Mar. 1993, pp. 21-24, vol. 12, No. 1.

Macsweeney, S.T. et al. "Pathogenesis of abdominal aortic aneurysm" Br. J. Surg., Jul. 1994, pp. 935-941, vol. 81, No. 7.

Malinow, M.R. & Maruffo, C.A. "Naturally occurring atherosclerosis in howler monkeys (Alouatta caraya)" J. Atheroscler. Res. Jul.-Aug. 1966, pp. 368-380, vol. 6, No. 4.

Nackman, G.B. et al. "Elastin degredation products induce adventitial angiogenesis in the Anidjar/Dobrin rat aneurysm model" Surgery, Jul. 1997, pp. 39-44, vol. 122, No. 1.

Nitatore et al. "Fast Dynamic MRI of Aortic Dissection: flow assessment by subsecondal imanging", Radiation Med., Jan.-Feb. 1999, pp. 9-14, vol. 17, No. 1.

Norrgard, O. et al. "Familial aortic aneurysms: serum concentrations of triglyceride, cholesterol, HDL-cholesterol and (VLDL+LDL)-cholesterol" Br. J. Surg., Feb. 1985, pp. 113-116, vol. 72, No. 2.

Norrgard, O. et al. "High concentrations of Lp(a) lipoprotein in serum are common among patients with abdominal aortic aneurysms" Int. Angiol., Jan.-Mar. 1988, pp. 46-49, vol. 7, No. 1.

Pearce et al. "Cellular components and features of immune response in abdominal aortic aneurysms." Annals NY Acad. Sci., Nov. 1996, pp. 175-186, vol. 800.

Satta, J. et al. "Chronic Inflammation and Elastin Degradation in Abdominal Aortic Aneurysm Disease: an Immunohistochemical and Electron Microscopic Study" Eur. J. Vasc. Endovasc. Surg., Apr. 1998, pp. 313-319, vol. 15.

Schneider et al. "Indocyanine green videoangiography of hemorrhagic retinal arterial macroaneurysms", Ophthalmologica, 1997, pp. 115-118, vol. 211.

Smith, W. et al. "Plasma fibrinogen levels, other cardiovascular risk factors, and age-related maculopathy: the Blue Mountains Eye Study" Arch. Ophthalmol. May 1998, pp. 583-587, vol. 116, No. 5.

Smith, W. et al., "Risk factors for age-related macular degeneration: Pooled findings from three continents" Ophthalmology, Apr. 2001, pp. 697-704, vol. 108, No. 4.

Sperduto, R.D. & Hiller, R. "Systemic hypertension and age-related maculopathy in the Framingham study" Arch. Opthalmol., Feb. 1986, pp. 216-219, vol. 104, No. 2.

Strickland, H.L. & Bond, M.G. "Aneurysms in a large colony of squirrel monkeys (Saimiri sciureus)" Lab Anim. Sci., Dec. 1983, pp. 589-592, vol. 33, No. 6.

Thompson, R.W. "Basic science of abdominal aortic aneurysms: emerging therapeutic strategies for an unresolved clinical problem" Curr. Opin. Cardiol., Sep. 1996, pp. 504-518, vol. 11, No. 5.

Tilson, M.D. & Stansel, H.C. "Differences in results for aneurysm vs occlusive disease after bifurcation grafts: results of 100 elective grafts." Arch. Surg., Oct. 1980, pp. 1173-1175, vol. 115, No. 10.

Tilson, MD, & Newman, K. "Rationale for molecular approaches to the etiology of abdominal aortic aneurysm disease" J. Vasc. Surg., May 1992, pp. 924-925, vol. 15, No. 5.

Van Der Wel et al. "CD1 and major histocompatibility complex II molecules follow a different course during dendritic cell maturation.", Mol Biol Cell. Aug. 2003;14(8):3378-88. Epub 2003 Jun. 13.

Verloes, A. et al. "Genetic aspects of abdominal aortic aneurysm." Ann. NY Acad. Sci. Nov. 18, 1996, pp. 44-55, vol. 800.

Vinding, T. et al. "Risk factor analysis for atrophic and exudative age-related macular degeneration. An epidemiological study of 1000 aged individuals" Acta. Opthalmol., Feb. 1992, pp. 66-72, vol. 70, No. 1.

Wilmink, A.B. & Quick, C.R. "Epidemiology and potential for prevention of abdominal aortic aneurysm" Br. J. surg., Feb. 1998, pp. 155-162, vol. 85, No. 2.

Zarins, C.K. et al. "Aneurysm formation in experimental atherosclerosis: relationship to plaque evolution" J. Vasc. Surg., 1990, pp. 246-256, vol. 12.

Zarins, C.K. et al. "Aneurysmal enlargement of the aorta during regression of experimental atherosclerosis" J. Vasc. Surg., Jan. 1992, pp. 90-101, vol. 15, No. 1.

* cited by examiner

DIAGNOSTICS AND THE THERAPEUTICS FOR MACULAR DEGENERATION

This application claims the benefit of U.S. Provisional Application No. 60/120,822, filed Feb. 19, 1999; U.S. Provisional Application No. 60/120,668, filed Feb. 19, 1999; and U.S. Provisional Application No. 60/123,052, filed Mar. 5, 1999.

FIELD OF THE INVENTION

The invention relates to diagnostics and therapeutics and animal models for macular degeneration, specifically as they relate to the association described herein between macular degeneration and arterial wall disruptive disorders.

BACKGROUND OF THE INVENTION

Macular degeneration is a clinical term that is used to describe a variety of diseases that are all characterized by a progressive loss of central vision associated with abnormalities of Bruch's membrane, the neural retina and the retinal pigment epithelium. Clinically, macular degeneration is associated with progressive diminution of visual acuity in the central portion of the visual field, changes in color vision, and abnormal dark adaptation and sensitivity (Steinmetz, et al., 1993; Brown & Lovie-Kitchin, 1983; Brown, et al., 1986; Sunness, et al., 1985; Sunness, et al., 1988; Sunness, et al., 1989; Eisner, et al., 1987; Massof, et al., 1989; Chen, et al., 1992). When the manifestations of macular degeneration occur after age 50 years, the disorder is termed age-related macular degeneration (AMD).

AMD is the leading cause of legal blindness in North America and Western Europe (Hyman, 1992) and has become a significant health problem as the percentage of individuals above the age of 50 increases. In the Beaver Dam, Wis. population, the incidence of AMD was estimated to be 9.2% for persons over the age of 40 (Klein, et al., 1995). The Framingham Eye Study found the overall incidence of AMD to be 8.8%, with a 27.9% incidence in the 75–85 year old population (Kahn, et al., 1977; Leibowitz, et al., 1980). In an Australian study, 18.5% of those over age 85 were estimated to be afflicted with AMD (O'Shea, 1996). Variations in estimated incidence are likely a result of the use of different criteria for a diagnosis of AMD in different studies, or they may result from different risk factors among the various populations studied.

Two principal clinical manifestations of AMD have been described, both of which can occur in the same patient (Green and Key, 1977). They are referred to as the dry, or atrophic, form, and the wet, or exudative, form (Sarks and Sarks, 1989; Elman and Fine, 1989; Kincaid, 1992). In the dry form, the RPE and retina degenerate without coincident neovascularization. The region of atrophy that results is referred to as geographic atrophy. While atrophic AMD is typically considered less severe than the exudative form because its onset is less sudden, no treatment is effective at halting or slowing its progression. In the less common, but more devastating, exudative form, neovascular "membranes" derived from the choroidal vasculature invade Bruch's membrane, leak, and often cause detachments of the RPE and/or the neural retina (Elman and Fine, 1989). This event can occur over a short period of time and can lead to rapid and permanent loss of central vision. If one eye is affected, there is a high degree of probability that the second eye will develop a choroidal neovascular membrane within five years of the initial event (Macular Photocoagulation Study, 1977). Important clinical signs of neovascular AMD include gray-green neovascular membranes, dome-shaped RPE detachments, and disciform scars (caused by proliferation of fibroblasts and retinal glial cells) which are best visualized by their hyperfluorescence on fluorescein angiography (Elman and Fine, 1989). A number of studies have demonstrated that the presence of macular drusen is a strong risk factor for the development of both atrophic and neovascular AMD (Gass, 1973; Lovie-Kitchin and Bowman, 1985; Lewis, et al., 1986; Sarks, 1980; Sarks, 1982; Small, et al., 1976; Sarks, et al., 1985; Vinding, 1990; Bressler, et al., 1994; Bressler, et al., 1990; Macular Photocoagulation Study). Pauleikhoff, et al. (1990) demonstrated that the size, number, density and extent of confluency of drusen are important determinants of the risk of AMD. The risk of developing neovascular complications in patients with bilateral drusen has been estimated at 3–4% per year (Mimoun, et al., 1990). A recent report from the Macular Photocoagulation Study Group shows a relative risk of 2.1 for developing choroidal neovascularization in eyes possessing 5 or more drusen, and a risk of 1.5 in eyes with one or more large drusen (Macular Photocoagulation Study, 1997). The correlation between drusen and AMD is significant enough that many investigators and clinicians refer to the presence of soft drusen in the macula, in the absence of vision loss, as "early AMD" (Midena, et al., 1997; Tolentino, et al., 1994), or "early age-related maculopathy" (Bird, et al., 1995). In addition to macular drusen, Lewis et al. (1986) found that the degree of extramacular drusen is also a significant risk factor for the development of AMD.

A number of population-based studies indicate that AMD has a genetic component, based upon the examination of the rates of AMD in different racial groups and the degree of familial aggregation of AMD (Hyman, et al., 1983). For example, Caucasians appear to be at greater risk than individuals of Hispanic origin (Cruickshanks, et al., 1997). In addition, a black population on Barbados had a lower incidence of advanced AMD than the local Caucasian population (Schachat, et al., 1995). Studies involving twins and other siblings have demonstrated that, the more related two individuals are, the more likely they are to be at the same risk of developing AMD (Heiba, et al., 1994; Klein, et al., 1994; Meyers and Zacchary, 1988; Meyers, 1994; Meyers, et al., 1995; Piguet, et al., 1993; Seddon, et al., 1997; Silvestri, et al., 1994). These findings suggest that heredity contributes significantly to an individual's risk of developing AMD, but the gene(s) responsible have not been identified. Although a recent report suggested that mutations in the photoreceptor ABCR rim protein cause up to 15% of AMD cases in the United States (Allikmets, et al., 1997), more recent data has shown this not to be the case (De La Paz, et al., 1998; Stone et al., 1998). Thus, no gene accounting for all AMD has been identified.

Other maculopathies, typically with an earlier onset of symptoms than AMD, have been described. These include North Carolina macular dystrophy (Small, et al., 1993), Sorsby's fundus dystrophy (Capon, et al., 1989), Stargardt's disease (Parodi, 1994), pattern dystrophy (Marmor and Byers, 1977), Best disease (Stone, et al., 1992), dominant drusen (Deutman and Jansen, 1970), and radial drusen ("malattia leventinese") (Heon, et al., 1996). Several of these inherited disorders, including those that map to distinct chromosomal loci or for which the genes have been identified, are characterized by the presence of drusen (or other extracellular deposits in the subRPE space). Based on this information, it is likely that: (1) AMD is not a single, genetic disease, since different diseases with distinct chromosomal loci share morphologic differences (Holz, et al., 1995a; Mansergh et al., 1995; and (2) that drusen may develop as a result of a biological pathway induced by a variety of different insults, genetic or otherwise. AMD may actually be several diseases most of which are genetic, with environmental factors play some role in its development.

A number of gene loci have been reported as indicating a predisposition to macular degeneration: 1p21–q13, for recessive Stargardt's disease or findus flavi maculatus (Allikmets, R. et al. *Science* 277:1805–1807, 1997; Anderson, K. L. et al., *Am. J. Hum. Genet.* 55:1477, 1994; Cremers, F. P. M. et al., *Hum. Mol. Genet.* 7:355–362, 1998; Gerber, S. et al., *Am. J. Hum. Genet.* 56:396–399, 1995; Gerber, S. et al., *Genomics* 48:139–142, 1998; Kaplan, J. et al., *Nat. Genet.* 5:308–311, 1993; Kaplan, J. et al., *Am. J. Hum. Genet.* 55:190, 1994; Martinez-Mir, A. et al., *Genomics* 40:142–146, 1997; Nasonkin, I. et al., *Hum. Genet.* 102: 21–26, 1998; Stone, E. M. et al., *Nat. Genet.* 20:328–329, 1998); 1q25–q31, for recessive age related macular degeneration (Klein, M. L. et al., *Arch. Ophthalmol.* 116:1082–1088, 1988); 2p16, for dominant radial macular drusen, dominant Doyne honeycomb retinal degeneration or Malattia Leventinese (Edwards, A. O. et al., *Am. J. Ophthalmol.* 126:417–424, 1998; Heon, E. et al., *Arch. Ophthalmol.* 114:193–198, 1996; Heon, E. et al.,. *Invest. Ophthalmol Vis. Sci.* 37:1124, 1996; Gregory, C. Y. et al., *Hum. Mol. Genet.* 7:1055–1059, 1996); 6p1.2-cen, for dominant macular degeneration, adult vitelloform (Felbor, U. et al. *Hum. Mutat.* 10:301–309, 1997); 6p21.1 for dominant cone dystrophy (Payne, A. M. et al. *Am. J. Hum. Genet.* 61:A290, 1997; Payne, A. M. et al., *Hum. Mol. Genet.* 7:273–277, 1998; Sokol, I. et al., *Mol. Cell.* 2:129–133, 1998); 6q, for dominant cone-rod dystrophy (Kelsell, R. E. et al. *Am. J. Hum. Genet.* 63:274–279, 1998); 6q11–q15, for dominant macular degeneration, Stargardt's-like (Griesinger, I. B. et al., *Am. J. Hum. Genet.* 63:A30, 1998; Stone, E. M. et al., *Arch. Ophthalmol.* 112:765–772, 1994); 6q14–q16.2, for dominant macular degeneration, North Carolina Type (Kelsell, R. E. et al., *Hum. Mol. Genet.* 4:653–656, 1995; Robb, M. F. et al., *Am. J. Ophthalmol.* 125:502–508, 1998; Sauer, C. G. et al., *J. Med. Genet.* 34:961–966, 1997; Small, K. W. et al., *Genomics* 13:681–685, 1992; Small, K. W. et al., *Mol. Vis.* 3:1, 1997); 6q25–q26, dominant retinal cone dystrophy 1 (Online Mendelian Inheritance in Man (™). Center for Medical Genetics, Johns Hopkins University, and National Center for Biotechnology Information, National Library of Medicine. http://www3.ncbi.nlm.nih.gov/omim (1998); 7p21–p15, for dominant cystoid macular degeneration (Inglehearn, C. F. et al., *Am. J. Hum. Genet.* 55:581–582, 1994; Kremer, H. et al., *Hum. Mol. Genet.* 3:299–302, 1994); 7q31.3–32, for dominant tritanopia, protein: blue cone opsin (Fitzgibbon, J. et al., *Hum. Genet.* 93:79–80, 1994; Nathans, J. et al., *Science* 193:193–232, 1986; Nathans, J. et al., *Ann. Rev. Genet.* 26:403–424, 1992; Nathans, J. et al., *Am. J. Hum. Genet.* 53:987–1000, 1993; Weitz, C. J. et al., *Am. J. Hum. Genet.* 50:498–507, 1992; Weitz, C. J. et al., *Am. J. Hum. Genet.* 51:444–446, 1992); not 8q24, for dominant macular degeneration, atypical vitelliform (Daiger, S. P. et al., In 'Degenerative Retinal Diseases', LaVail, et al., eds. Plenum Press, 1997; Ferrell, R. E. et al., *Am. J. Hum. Genet.* 35:78–84, 1983; Leach, R. J. et al., *Cytogenet. Cell Genet.* 75:71–84, 1996; Sohocki, M. M. et al., *Am. J. Hum. Genet.* 61:239–241, 1997); 11p12–q13, for dominant macular degeneration, Best type (bestrophin) (Forsman, K. et al., *Clin. Genet.* 42:156–159, 1992; Graff, C. et al., *Genomics,* 24:425–434, 1994; Petrukhin, K. et al., *Nat. Genet.* 19:241–247, 1998; Marquardt, A. et al., *Hum. Mol. Genet.* 7:1517–1525, 1998; Nichols, B. E. et al., *Am. J. Hum. Genet.* 54:95–103, 1994; Stone, E. M. et al., *Nat. Genet.* 1:246–250, 1992; Wadeilus, C. et al., *Am. J. Hum. Genet.* 53:1718, 1993; Weber, B. et al., *Am. J. Hum. Genet.* 53:1099, 1993; Weber, B. et al., *Am. J. Hum. Genet.* 55:1182–1187, 1994; Weber, B. H., *Genomics* 20: 267–274, 1994; Zhaung, Z. et al., *Am. J. Hum. Genet.* 53:1112, 1993); 13q34, for dominant macular degeneration, Stargardt type (Zhang, F. et al., *Arch. Ophthalmol.* 112:759–764, 1994); 16p12.1, for recessive Batten disease (ceroid-lipofuscinosis, neuronal 3), juvenile; protein:Batten disease protein (Batten Disease Consortium, *Cell* 82:949–957, 1995; Eiberg, H. et al., *Clin. Genet.* 36:217–218, 1989; Gardiner, M. et al., *Genomics* 8:387–390, 1990; Mitchison, H. M. et al., *Am. J. Hum. Genet.* 57:312–315, 1995, Mitchison, H. M. et al., *Am. J. Hum. Genet.* 56:654–662, 1995; Mitchison, H. M. et al., *Genomics* 40:346–350, 1997; Munroe, P. B. et al., *Am. J. Hum. Genet.* 61:310–316, 1997; 17p, for dominant areolar choroidal dystrophy (Lotery, A. J. et al., *Ophthalmol. Vis. Sci.* 37:1124, 1996); 17p13–p12, for dominant cone dystrophy, progressive (Balciuniene, J. et al., *Genomics* 30:281–286, 1995; Small, K. W. et al., *Am. J. Hum. Genet.* 57:A203, 1995; Small, K. W. et al., *Am. J. Ophthalmol.* 121:13–18, 1996); 17q, for cone rod dystrophy (Klystra, J. A. et al., *Can. J Ophthalmol.* 28:79–80, 1993); 18q21.1–q21.3, for cone-rod dystrophy, de Grouchy syndrome (Manhant, S. et al., *Am. J. Hum. Genet.* 57:A96, 1995; Warburg, M. et al., *Am. J. Med. Genet.* 39:288–293, 1991); 19q13.3, for dominant cone-rod dystrophy; recessive, dominant and 'de novo' Leber congenital amaurosis; dominant RP; protein: cone-rod otx-like photoreceptor homeobox transcription factor (Bellingham, J. et al., In 'Degenerative Retinal Diseases', LaVail, et al., eds. Plenum Press, 1997; Evans, K. et al., *Nat. Genet.* 6:210–213, 1994; Evans, K. et al., *Arch. Ophthalmol.* 113:195–201, 1995; Freund, C. L. et al., *Cell* 91:543–553, 1997; Freund, C. L. et al., *Nat. Genet.* 18:311–312, 1998; Gregory, C. Y. et al., *Am. J. Hum. Genet.* 55:1061–1063, 1994; Li, X. et al., *Proc. Natl. Acad. Sci USA* 95:1876–1881, 1998; Sohocki, M. M. et al., *Am. J. Hum. Genet.* 63:1307–1315, 1998; Swain, P. K. et al., *Neuron* 19:1329–1336, 1987; Swaroop, A. et al., *Hum. Mol. Genet. In press,* 1999); 22q12.1–q13.2, for dominant Sorsby's fundus dystrophy, tissue inhibitors of metalloproteases-3 (TIMP3) (Felbor, U. et al., *Hum. Mol. Genet.* 4:2415–2416, 1995; Felbor, U. et al., *Am. J. Hum. Genet.* 60:57–62, 1997; Jacobson, S. E. et al., *Nat. Genet.* 11:27–32, 1995; Peters, A. et al., *Retina* 15:480–485, 1995; Stöhr, H. et al., *Genome Res.* 5:483–487, 1995; Weber, B. H. F. et al., *Nat. Genet.* 8:352–355, 1994; Weber, B. H. F. et al., *Nat. Genet.* 7:158–161, 1994; Wijesvriya, S. D. et al., *Genome Res.* 6:92–101, 1996); and Xp11.4, for X-linked cone dystrophy (Bartley, J. et al., *Cytogenet. Cell. Genet.* 51:959, 1989; Bergen, A. A. B. et al., *Genomics* 18:463–464, 1993; Dash-Modi, A. et al., *Invest. Ophthalmol. Vis. Sci.* 37:998, 1996; Hong, H.-K., *Am. J. Hum. Genet* 55:1173–1181, 1994; Meire, F. M. et al., *Br. J. Ophthalmol.* 78:103–108, 1994; Seymour, A. B. et al., *Am. J. Hum. Genet.* 62:122–129, 1998), the teachings of which are incorporated herein by reference. In addition, the world wide web site http://WWW.SPH.UTH.TMC.EDU/RETNET/disease.htm lists genetic polymorphisms for macular degeneration and for additional retinal degenerations that also may be associated with macular degeneration. However, none of the above genes or polymorphisms has been found to be responsible for a significant fraction of typical late-onset macular degeneration.

"Environmental" conditions may modulate the rate at which an individual develops AMD or the severity of the disease. Light exposure has been proposed as a possible risk factor, since AMD most severely affects the macula, where light exposure is high. (Young, 1988; Taylor, et al., 1990; Schalch, 1992). The amount of time spent outdoors is associated with increased risk of choroidal neovascularization in men, and wearing hats and/or sunglasses is associated with a decreased incidence of soft drusen (Cruickshanks, et al., 1993). Accidental exposure to microwave irradiation has also been shown to be associated with the development of numerous drusen (Lim, et al., 1993). Cataract removal and light iris pigmentation has also been reported as a risk factor in some studies (Sandberg, et al., 1994). This suggests that: 1) eyes prone to cataracts may be more likely to develop AMD; 2) the surgical stress of cataract removal may result in increased risk of AMD, due to inflammation or other surgically-induced factors; or 3) cataracts prevent excessive light exposure from falling on the macula, and are in some way prophylactic for AMD. While it is possible that dark iris pigmentation may protect the macula from light damage, it is difficult to distinguish between iris pigmentation alone and other, cosegregating genetic factors which may be actual risk factors.

Dietary factors may also influence an individual's risk of developing AMD. Anecdotal evidence from Japan suggests that the incidence of AMD, while very low 20 years ago, has increased as urban Japanese acquired a more Western diet and lifestyle (Bird, 1997). Chemical exposure (Hyman, et al., 1983), smoking (Vingerling, et al., 1996), cardiovascular disease/atherosclerosis (Hyman, et al., 1983; Vingerling, et al., 1995; Blumenkranz, et al., 1986), hypertension (Christen, et al., 1997), dermal elastotic changes in non-sun exposed skin (Blumenkranz, et al., 1986), dietary fat intake (Mares-Perlman, et al., 1995b), low concentrations of serum lycopene (Mares-Perlman, et al., 1995a), and alcohol consumption (Ritter, et al., 1995) have been identified, in some studies, as additional risk factors for the development of wet and/or dry AMD. One recent prospective dietary study found that it is often possible to increase macular pigment density and/or serum concentrations of lutein and zeaxanthin by dietary intake (Hammond, et al., 1997), although the significance of this alteration in modulating macular disease remains to be determined. Thus, dietary consumption of some vegetables, (e.g., spinach, collard greens, kale) may be inversely associated with the risk of developing AMD (Seddon, et al., 1994), an effect which is presumably due to their lutein and zeaxanthin content.

Currently, there is no therapy that is capable of significantly slowing the degenerative progression of AMD, and treatment is limited to laser photocoagulation of the subretinal neovascular membranes that occur in 10–15% of affected patients, which may halt the progression of the disease but does not repair the damage or improve vision. A few clinical studies have shown that drusen regress and that visual acuity improves in some cases, following laser photocoagulation (Sigelman, 1991; Little, et al., 1997; Figueroa, et al., 1994; Frenneson and Nilsson, 1996). While prophylactic laser treatment may be helpful for some patients (Little, et al., 1997), it appears that other patients react adversely to laser treatment of the macula (Hyver, et al., 1997). In addition, while there may be long term benefits for the patient following photocoagulation, these may not be worth the loss of vision frequently associated with this procedure. Indocyanine green angiography is a promising imaging tool that may help identify those patients likely to benefit from laser therapy.

Better understanding of the biology of AMD may allow the development of therapies that can alter the natural history of the disease, serving to halt or reverse its progression. It is understood in the medical arts that any therapeutic intervention is more likely to have a beneficial effect on a patient if undertaken before irreversible pathological changes have occurred. In AMD, however, there exists no readily undertaken screening test that can identify those individuals at risk for developing the disease or for experiencing its unremitting progression. Early identification of AMD could also permit early intervention with greater likelihood of success using established or experimental treatment modalities, including photocoagulation or other techniques familiar to skilled artisans in ophthalmology. Discerning various phenotypes of AMD may identified that respond notably better or worse to a particular method of local treatment, and treatments may be selected accordingly. If the biological basis for certain phenotypes of AMD can be identified, then preventive measures may be undertaken to forestall the onset of the disease or to attenuate its progression. Hence, there exists a need in the art for diagnostic methods adapted for early detection of the disorder when it may still be at a stage amenable to therapeutic intervention.

Further, if the pathophysiological mechanisms for the disease can be elucidated, they can be compared to those mechanisms at work in diseases that appear to coexist with AMD with statistically significant frequency. Then, as therapies are identified for those coexistent diseases, there will be a rational basis for applying those same therapies or their analogues to treat AMD. Thus there exists a need for determining those pathological mechanisms that AMD shares with other disease entities, and a further need for using research in other fields of medicine to apply in the treatment of AMD. As common mechanisms for co-existent diseases are understood, it would be desirable to formulate therapies that beneficially affect the co-existent disease and the AMD, either by preventing the onset of the ocular disorder or by limiting its progression.

A method for diagnosing risk for AMD would permit the clinician to undertake those dietary, environmental or lifestyle interventions that may prevent the onset of the disease or limit its progress. For example, eliminating certain risk factors such as smoking and hypertension from the patient's lifestyle may positively affect the patient's likelihood of developing AMD, or may limit the severity of the disease. Determining an increased risk for developing AMD would provide the patient motivation for making difficult, though healthful, lifestyle choices, or would provide motivation for modifying her or his environment to minimize the risk of developing the disease. Further, determining an increased risk for developing AMD might provide for the patient a rational basis for undertaking other nutritional modifications or supplementations, such as increasing intake of vegetables, vitamins, minerals or nutriceuticals, that may decrease the likelihood of developing AMD or may decrease the severity of its progression. Susceptible individuals could then be targeted for improved health promotion and disease prevention measures for this disabling and highly prevalent disorder.

SUMMARY OF THE INVENTION

The invention relates to the discovery that the incidence of arterial wall disruptive disorders, including but not limited to aortic aneurysms, abdominal aortic aneurysms, etc. correlates with the incidence of age-related Macular Degeneration (AMD). The present invention therefore provides a novel method for diagnosing macular degeneration or a predisposition to developing macular degeneration, methods for treating or preventing the development of macular degeneration in a subject, by administering to the subject, a pharmaceutically effective amount of an arterial wall disruptive disorder therapeutic, and in vitro and in vivo assays for screening test compounds to identify macular degeneration therapeutics. Though the data used to determine the correlation between AMD with the development of arterial wall disruptive disorders used humans having an abdominal aortic aneurysm (AAA, it is likely that aneurysms that develop elsewhere in the body, such as the thoracic aorta, iliac artery, visceral artery, or peripheral aneurysms (e.g., popliteal artery, femoral artery), for example, also correlate with the incidence of AMD. Moreover, it is likely that other forms of macular degeneration in addition to AMD correlate with the incidence of AAA. In a preferred embodiment, a form of aneurysm that is associated with arterial inflammation, degeneration or autoimmunity may correlate with the incidence of AMD. Not to be limited to any particular theory, the aneurysm may be causes at least in part by atherosclerosis or infection. Alternatively, the aneurysm may be caused at least partially by an inherited connective tissue disorder.

In one aspect, the invention provides methods for diagnosing, or determining a predisposition to developing, macular degeneration in a subject by detecting one or more markers for arterial wall disruptive disorders which is indicative of macular degeneration or of a predisposition to developing macular degeneration. In one embodiment, the marker for arterial wall disruptive disorders is detected in the blood, urine, tissue, DNA or RNA of a subject. In a preferred embodiment, the arterial wall disruptive disorders is an aortic aneurysm, more specifically, it is an abdominal aortic aneurysm (AAA). In another preferred embodiment, the aortic aneurysm is a thoracic aortic aneurysm (TAA). In yet another preferred embodiment, the macular degeneration is Age Related Macular Degeneration (AMD).

In a preferred embodiment of the invention, the marker for an arterial wall disruptive disorder is a physical finding such as a pulsatile mass in the abdomen and is detected using a technique selected from the group consisting of physical exam, ultrasonography, computed tomography (CT scan), magnetic resonance imaging (MRI) and arteriography.

In another preferred embodiment, the marker is a cytokine, a chemokine, a protease, collagen, a collagen fragment, elastin, an elastin degradation product, an elastin associated molecule and immune cells, wherein levels of the marker differ in a subject with aortic aneurysm, or with a predisposition to developing aortic aneurysm, as compared to a normal healthy subject. In another preferred embodiment, the cytokine or chemokine is tumor necrosis factor α (TNFα), interleukin-1β (IL-1β), interleukin-6 (IL-6), interleukin-8 (IL-8), intracellular adhesion molecule (ICAM), soluble ICAM (sICAM) or oxidized low density lipoprotein (LDL). In another preferred embodiment, the protease is matrix metalloproteases 2 and 9 (MMP2, MMP9), plasmin, plasminogen activator inhibitor −1 (PAI-1), urokinase plasminogen activator (uPA), tissue plasminogen activators (tPAs), tissue inhibitors of metalloproteases (TIMPs) or α1-antitrypsin. In another embodiment, the elastin-associated molecule is serum amyloid P, emilin, fibrillin1, fibrillin2, fibrillin3, fibulins, vitronectin, lysyl oxidase, MFAP1, MFAP2, MFAP3, MFAP4 or MAGP2. In another embodiment, the immune cells are T cells, dendritic cells, B cells or macrophages, preferably dendritic cells.

In another embodiment, the marker may be selected from the group consisting of immunoglobulins, amyloid A (α1 amyloid A), amyloid P component, C5 and C5b-9 terminal complexes, HLA-DR, fibrinogen, Factor X, and prothrombin, complements 3, 5 and 9, complement reactive protein (CRP), immunoglobulin lambda and kappa light chains, Factor X, HLA-DR, apolipoprotein A, apolipoprotein E, antichymotrypsin, P2 microglobulin, factor X, fibrinogen, prothrombin, thrombospondin, elastin, collagen, vitronectin, ICAM-1, LFA1, LFA3, B7, IL-1, IL-6, IL-12, TNF-alpha, GM-CSF, heat shock proteins, colony stimulating factors (GM-CSF, M-CSFs), TNFα, and IL-10.

In another aspect, the invention provides a method for diagnosing, or determining a predisposition to, macular degeneration in a subject by isolating a nucleic acid from a subject and genotyping the nucleic acid, wherein at least one allele from an arterial wall disruptive disorder-associated haplotype is predictive of an increased risk of macular degeneration. In one embodiment, the invention provides a method for diagnosing, or determining a predisposition to, macular degeneration in a subject having family members diagnosed with arterial wall disruptive disorder by isolating a nucleic acid from a subject, amplifying the nucleic acid with primers which amplify a region of a chromosome corresponding to a polymorphic marker for arterial wall disruptive disorders and analyzing the amplification product, wherein the presence of a polymorphism indicative of an allele type linked to arterial wall disruptive disorder is indicative of an allele type linked to macular degeneration or a predisposition for developing macular degeneration. In another embodiment, the invention provides a method for diagnosing, or determining a predisposition to, macular degeneration in a subject having family members diagnosed with arterial wall disruptive disorder by isolating a genomic nucleic acid from a subject, amplifying short tandem repeat sequences in the genomic DNA to obtain a genotype, comparing the genotype to the genotype of known DNA sequences to detect nucleotide sequence polymorphisms and determining the presence or absence of a polymorphism in the genomic DNA of the subject, wherein the presence of a polymorphism indicative of an allele type linked to arterial wall disruptive disorder is indicative of an allele type linked to macular degeneration or a predisposition for developing macular degeneration. In a preferred embodiment, the genotype is a polymorphism in one of the fibrillin 1, type III collagen, α1-antitrypsin, COL3A1, TIMP(1) or haptoglobin loci. In a preferred embodiment, the subject is a mammal, more preferably a human. In yet another embodiment, the aortic aneurysm is an AAA or a TAA and the macular degeneration is AMD and preferably contains disciform scars and choroidal neovascularization (DS/CNV). In another embodiment, the invention provides a method for diagnosing, or detecting a predisposition to developing, macular degeneration in a subject by performing an immunoassay on a sample obtained from the subject using an antibody specific for a gene product indicative of aortic aneurysm, wherein detection of the presence of bound antibody indicates that the subject has aortic aneurysm or a predisposition to developing aortic aneurysm and therefore has macular degeneration or a predisposition for developing macular degeneration. The invention/also provides kits for performing the above immunoassay. In another embodiment, the invention provides a kit for diagnosing macular degeneration, containing primers for amplifying a region of a chromosome having a polymorphism indicative of aortic aneurysm, reagents for performing DNA amplification and reagents for analyzing the amplified nucleic acid.

In another aspect, the invention provides a method for treating or preventing the development of macular degeneration in a subject by administering a pharmaceutically effective amount of an arterial wall disruptive disorder therapeutic. In an embodiment, the arterial wall disruptive disorder therapeutic is an inhibitor of MMP2, MMP9, propranolol, CD18, IL-1β, IL-6, IL-8, TNFα or IFNγ. In another embodiment, the therapeutic is an inhibitor of a cytokine, a chemokine, a protease, collagen, a collagen fragment, elastin, an elastin degradation product, an elastin associated molecule or immune cells. In a preferred embodiment, the cytokine or chemokine is TNFα, IL-1β, IL-6, IL-8, ICAM, sICAM or oxidized LDL. In another preferred embodiment, the protease is selected MMP2, MMP9, plasmin, PAI-1, uPA, tissue plasminogen activators (tPAs), tissue inhibitors of metalloproteases (TIMPs) and α1-antitrypsin. In another preferred embodiment, the elastin associated molecule is serum amyloid P, emilin, fibrillin1, fibrillin2, fibrillin3, fibulins, vitronectin, lysyl oxidase, MFAP1, MFAP2, MFAP3, MFAP4 or MAGP2. The immune cells are preferably T cells, dendritic cells, B cells and macrophages, in particular dendritic cells.

In another aspect, the invention relates to a pharmaceutical composition useful for treating or preventing macular degeneration, comprising an effective amount of an aortic aneurysm therapeutic and a therapeutically acceptable carrier. The aortic aneurysm is preferably an AAA or TAA and the macular degeneration is AMD, in particular the exudative or neovascular (wet) form, which contains disciform scars and/or choroidal neovascularization (DS/CNV).

In another aspect, the invention provides methods for identifying an agent for, or determining the efficacy of, an agent for treating or preventing macular degeneration in a subject by administering to a subject an agent at a non-toxic dosage and determining whether an aneurysm has stopped enlarging or has resolved. In another embodiment, the invention provides a method for identifying an agent for treating or preventing macular degeneration in a subject by contacting a non-human model for aortic aneurysm with an agent and monitoring one or more markers of aortic aneurysm, wherein the absence or disappearance of one or more markers is indicative of the inhibition of macular degeneration. Preferably the arterial wall disruptive disorder is an AAA or a TAA, and the macular degeneration is AMD, particularly the exudative or neovascular (wet) form, which contains disciform scars and/or choroidal neovascularization (DS/CNV). In another preferred embodiment, the marker is a pulsatile mass in the abdomen which is detected by one or more of physical exam, ultrasonography, computed tomography (CT scan), magnetic resonance imaging (MRI) and arteriography. Alternatively, the marker is selected from the group consisting of a cytokine, a chemokine, a protease, collagen, a collagen fragment, elastin, an elastin degradation product, an elastin associated molecule and immune cells, wherein levels of said marker differ in a subject with arterial wall disruptive disorder, or with a predisposition to developing aortic aneurysm, as compared to a normal healthy subject. In a preferred embodiment, the cytokine or chemokine is tumor necrosis factor α (TNFα), interleukin-1β (IL-1β), interleukin-6 (IL-6), interleukin-8 (IL-8), intracellular adhesion molecule (ICAM), soluble ICAM (sICAM) or oxidized low density lipoprotein (LDL). In another embodiment, the protease is MMP2, MMP9, plasmin, PAI-1, a uPA, a tPA, a TIMP or α1—antitrypsin. In another embodiment, the elastin associated molecule is serum amyloid P, emilin, fibrillin1, fibrillin2, fibrillin3, fibulins, vitronectin, lysyl oxidase, MFAP1, MFAP2, MFAP3, MFAP4 or MAGP2. In still another embodiment, the immune cells are T cells, dendritic cells, B cells or macrophages, preferably dendritic cells.

In another aspect, the invention provides animal models for macular degeneration which have or are predisposed for developing aortic aneurysm, wherein the presence of, severity of, or predisposition for aortic aneurysm in the animal is indicative of the presence of, severity of, or predisposition for macular degeneration. In a preferred embodiment the animal has been treated with an agent so that it develops aortic aneurysm. In another preferred embodiment, the animal is a transgenic animal.

Other features and advantages of the invention will be apparent from the following figures, detailed description, and claims.

DETAILED DESCRIPTION OF THE INVENTION

The invention relates to the discovery that the incidence of certain arterial wall disruptive disorders correlates with the incidence of Age-Related Macular Degeneration (AMD). In particular, the invention relates to methods and kits for diagnosing AMD or for predicting risk of developing AMD or for determining risk of progression in established AMD, wherein the diagnosis of AMD or the prediction or determination of risk for AMD relates to the diagnosis of an arterial wall disruptive disorder. In one embodiment, the arterial wall disruptive disorder may be an aneurysm. In one embodiment, the aneurysm may be located in the abdominal aorta.

In one embodiment, described in detail herein, the invention relates to the discovery that the incidence of aneurysmal disorders correlates with the incidence of Age-Related Macular Degeneration. While the invention will be described by particular reference to aortic aneurysmal disorders, it is understood that those pathological processes implicated in these disorders are at work on a more generalized basis within the vascular system. (Baxter BT, et al., "Abdominal aortic aneurysms are associated with altered matrix proteins of nonaneurysmal aortic segments", J Vasc Surg, 19(5):797–802; discussion 803 1994 May.) Other locations for aneurysmal disorders are familiar to practitioners in the relevant arts. In certain of these locations, pathological processes have been identified that are similar to those detected in aortic aneurysms. For example, pathological processes have been identified in aneurysm formation in the cerebral vasculature that are similar to those associated with aortic aneurysms. (Gaetani P, et al., "Metalloproteases and intracranial vascular lesions", Neurol Res, 21(4):385–90 1999 Jun). However, the anatomy of the aorta, with its variable distribution of structural elements such as collagen and elastin, makes this vessel a particularly exemplary one to study. (Halloran B G, et al., "Localization of aortic disease is associated with intrinsic differences in aor," J Surg Res, 59(1):17–22 1995 Jul). Hence, while the present invention will be illustrated by reference to the aorta, it is understood that the kits and methods described herein may be related to the presence of arterial wall disruptive disorder in any artery of the body.

4.1: Definitions

The meaning of certain terms and phrases as used in the following detailed description and claims are defined as follows:

The term "agonist", as used herein, is meant to refer to an agent that enhances or upregulates (e.g., potentiates or supplements) the production or activity of a gene product.

An agonist can also be a compound which increases the interaction of a gene product, molecule or cell with another gene product, molecule or cell, e.g., of a gene product with another homologous or heterologous gene product, or of a gene product with its receptor. A preferred agonist is a compound which enhances or increases binding or activation of a transcription factor to an upstream region of a gene and thereby activates the gene. Any agent that activates gene expression, e.g., by increasing RNA or protein synthesis or decreasing RNA or protein turnover, or gene product activity may be an agonist whether the agent acts directly on the gene or gene product or acts indirectly, e.g., upstream in the gene regulation pathway. Agonists may be RNAs, peptides, antibodies and small molecules, or a combination thereof.

The phrase "AMD associated fundus findings," refers to those abnormal findings indicative of AMD. As examples, AMD associated fundus findings may include the presence of multiple drusen in the periphery, a greyish macula, peripapillary atrophy, choroidal neovascular membrane and/or disciform scars or geographic atrophy (GA). AMD associated fundus findings may include those findings detected in vivo by conventional optical methods known in the ophthalmological arts or by any other method that is non-destructive to the fundus.

The term "animal model", as used herein, includes transgenic animals, naturally occurring animals with genetic mutations and non-transgenic animals that have been treated with one or more agents, or combinations thereof (e.g., a skid mouse), any of which may serve as experimental models for a disease, e.g., macular degeneration or aortic aneurysm. For example, a transgenic mouse may be a mouse in which a gene is knocked out or in which a gene is overexpressed.

The term "antagonist" as used herein is meant to refer to an agent that down-regulates (e.g., suppresses or inhibits) the production or activity of a gene product. Such an antagonist can be an agent which inhibits or decreases the interaction between a gene product, molecule or cell and another gene product, molecule or cell. A preferred antagonist is a compound which inhibits or decreases binding or activation of a transcription factor to an upstream region of a gene and thereby blocks activation of the gene. Any agent that inhibits gene expression or gene product activity may be an antagonist whether the agent acts directly on the gene or gene product or acts indirectly, e.g., upstream in the gene regulation pathway. An antagonist can also be a compound that downregulates expression of a gene or which reduces the amount of gene product present, e.g., by decreasing RNA or protein synthesis or increasing RNA or protein turnover. Antagonists may be RNAs, peptides, antibodies and small molecules, or a combination thereof.

The term "arterial wall disruptive disorder" refers to those abnormalities of arterial walls characterized by the formation of aneurysms or by the formation of frank disruptions such as dissections.

The term "associate" or "interact" as used herein is meant to include detectable relationships or associations (e.g., biochemical interactions) between molecules, such as interaction between protein—protein, protein-nucleic acid, nucleic acid-nucleic acid, protein-carbohydrate, carbohydrate—carbohydrate, protein-lipid, lipid—lipid, etc., and protein-small molecule or nucleic acid-small molecule in nature.

The term "dendritic cell" or "DC" as used herein refers to hematopoietic cells characterized by their unusual dendritic morphology, their potent antigen-presenting capability and their lack of lineage-specific markers such as CD3, CD 19, CD 16, CD 14, which distinguishes them respectively from T cells, B cells, NK cells, and monocytes. Currently there are at least two ontogenic pathways for dendritic cell development: those that derive from myeloid-committed hematopoietic precursors and those that derive from lymphoid-committed hematopoietic precursors. Myeloid-committed precursors which give rise to granulocytes and monocytes can also differentiate into Langerhans cells of the skin and myeloid related dendritic cells in the secondary lymphoid tissue. (See Lotze, M. T. and Thomson, A. W. (Eds.) (1999) "Dendritic Cells", Academic Press, San Diego, Calif., for a number of reviews on dendritic cells, the teachings of which are incorporated herein by reference).

The term "dendritic cell precursor" or "DC precursor" as used herein refers to cell types from which a dendritic cell is derived upon differentiation and maturation. A dendritic cell precursor may be a bone marrow stem cell, a lymphiod cell lineage-committed cell or a myeloid cell lineage-committed cell from which a dendritic cell may develop after exposure to certain DCRMs. For example, DC precursors of the myeloid lineage can be induced to differentiate into DCs by treatment with GM-CSF.

The term "dendritic cell process" refers to a portion of a dendritic cell which projects or extends away from the center of the dendritic cell.

A "disease" is a disorder, as defined herein, characterized by clinical events including clinical symptoms and clinical signs. Clinical symptoms are those experiences reported by a patient that indicate to the clinician the presence of pathology. Clinical signs are those objective findings on physical or laboratory examination that indicate to the clinician the presence of pathology.

A "disorder" refers broadly to any abnormality of an organ, whether structural, histological, biochemical or any other abnormality.

The term "drusen" as used herein encompasses a number of phenotypes, all of which develop, between the inner collageous layer of Bruch's membrane and the RPE basal lamina. Hard drusen are small distinct deposits comprised of homogeneous eosinophilic material and are usually round or hemispherical, without sloped borders. Soft drusen are larger, usually not homogeneous, and typically contain inclusions and spherical profiles. Some drusen may be calcified. The term "diffuse drusen," or "basal linear deposit," is used to describe the amorphous material which forms a layer between the inner collagenous layer of Bruch's membrane and the retinal pigment epithelium (RPE). This material can appear similar to soft drusen histologically, with the exception that it is not mounded.

The term "drusen associated marker" refers to a phenotype or genotype that is involved with the development of drusen formation and ultimately the development of a drusen associated ocular disease ocular disorder. Examples of phenotypic markers include: dysfuncational and/or RPE death, immune mediated events, dendritic cells proliferation, migration and differentiation extrusion of the DC process into the sub RPE space (e.g. by detecting the presence or level of a dendritic cell marker such as CD68, CD1a and S100), the presence of geographic atrophy or disciform scars, the presence of choroidal neovascularization and/or choroidal fibrosis, especially in the macula. Examples of genotypic markers include mutant genes and/or a distinct pattern of differential gene expression (Drusen Development Pathway"), including genes that are upregulated or down-regulated in drusen forming ocular tissue associated with drusen biogenesis. For example genes expressed by dysfunctional and/or dying RPE cells include: HLA-DR, CD68, vitronectin, apolipoprotein E, clusterin and S-100, heat shock protein 70, death protein, proteasome, Cu/Zn superoxide dismutase, cathepsins, and death adaptor protein RAIDD. Markers involved in immune mediated events include: autoantibodies (e.g. directed against drusen, RPE and/or retina components), leukocytes, dendritic cells, myofibroblasts, type VI collagen, and a cadre of chemokines and cytokines. Molecules associated with drusen include: immunoglobulins, amyloid A, amyloid P component, HLA-DR, fibrinogen, Factor X, prothrombin, complements 3, 5, 9, and 56–9, creactive protein (CRP) apolipoprotein A, apolipoprotein E, antichymotrypsin, β2 microglobulin, thrombospondin, and vitronectin autoantibodies (e.g. directed against drusen, RPE and/or retina components), leukocytes and type VI collagen. Molecules associated with drusen include: immunoglobulins, amyloid A (α1 amyloid A), amyloid P component, C5 and C5b-9 terminal complexes, HLA-DR, fibrinogen, Factor X, and prothrombin, complements 3, 5 and 9, complement reactive protein (CRP), immunoglobulin lambda and kappa light chains, Factor X, HLA-DR, apolipoprotein A, apolipoprotein E, antichymotrypsin, β2 microglobulin, factor X, fibrinogen, prothrombin, thrombospondin, elastin, collagen, and vitronectin. Markers of drusen associated dendritic cells include: CD1a, CD4, CD14, CD68, CD83, CD86, and CD45, PECAM, MMP14, ubiquitin, and FGF. Important dendritic cell-associated accessory molecules that participate in T cell recognition include ICAM-1, LFA1, LFA3, and B7, IL-1, IL-6, IL-12, TNF-alpha, GM-CSF and heat shock proteins. Markers associated with dendritic cell expression include: colony stimulating factor, TNFα, and I1-1. Markers associated with dendritic cell proliferation include: GM-CSF, IL-4, I1-3, SCF, FLT-3 and TNFα. Markers associated with dendritic cell differentiation include IL-10, M-CSF, IL-6 and IL-4.

The term "drusen-associated ocular disease" as used herein refers to any disease in which drusen formation takes place and for which drusen causes or contributes thereto. Macular degenerations, the accumulation of drusen creates a physical barrier that appears to impede normal metabolite and waste diffusion between the choriocapillaris and the retina. As a result, the diffusion of oxygen, glucose, and other nutritive or regulatory serum-associated molecules required to maintain the health of the retina and RPE are inhibited.

A "drusen-associated molecule" or "DRAM" as used herein refers to any protein, carbohydrate, glycoconjugate (e.g., glycoprotein or glycolipid), other lipid, nucleic acid or other molecule which is found in association with, or interacting with, a drusen deposit. DRAMS may include cellular fractions or organelles that are not normally found deposited in, or in association with, a tissue unless it is affected by drusen or which is not present in drusen-affected and normal tissue in equivalent amounts.

The term "extracellular matrix" ("ECM") refers to, e.g., the collagens, proteoglycans, non-collagenous glycoproteins and elastins that surround cells and provide structural and functional support for cells as well as maintain various functions of cells, such as cell adhesion, proliferation, differentiation and protein synthesis. A skilled artisan will appreciate that the precise composition and physical properties of ECM, as well as its function, vary between various cell types, between various tissues, and between various organs.

A "fibrosis associated reaction" is any process that relates to tissue repair, including the formation of new blood vessels (angiogenesis), the migration and proliferation of fibroblasts, the deposition of extracellular matrix and the maturation and organization of fibrous tissue.

An "immune mediated event" refers to any event that occurs as part of the processes of acute or chronic inflammation. The histological, biochemical and genetic processes of acute and chronic inflammation are familiar to practitioners of ordinary skill in the art.

The term "inhibit" as used herein means to prevent or prohibit and is intended to include total inhibition, partial inhibition, reduction or decrease.

The term "macular degeneration" refers to any of a number of conditions in which the retinal macula degenerates or becomes dysfunctional, e.g., as a consequence of decreased growth of cells of the macula, increased death or rearrangement of the cells of the macula (e.g., RPE cells, loss of normal biological function, or a combination of these events. Macular degeneration results in the loss of integrity of the histoarchitecture of the cells of the normal macula and/or the loss of function of the cells of the macula. Any condition which alters or damages the integrity or function of the macula (e.g., damage to the RPE or Bruch's membrane) may be considered to fall within the definition of macular degeneration. Other examples of diseases in which cellular degeneration has been implicated include retinal detachment, chorioretinal degenerations, retinal degenerations, photoreceptor degenerations, RPE degenerations, mucopolysaccharidoses, rod-cone dystrophies, cone-rod dystrophies and cone degenerations.

The term "marker" is used herein to refer to any phenotype or genotype that is characteristic of a disorder or a disease. The phenotype may include physical findings, biochemical components, or any molecule or gene product which is upregulated or downregulated in the disorder or disease, and when measured is therefore indicative of the disorder or disease when levels are measured. Genotypes that can act as markers include any polymorphism or mutation that is associated with a particular disorder or disease.

The terms "modulation", "alteration", "modulate", or "alter"are used interchangeably herein to refer to both upregulation (i.e., activation or stimulation (e.g., by agonizing or potentiating)) and downregulation (i.e., inhibition or suppression (e.g., by antagonizing, decreasing or inhibiting)) of an activity. For example, the activity that is modulated may be gene expression or may be the growth, proliferation, migration or differentiation of dendritic cells. "Modulates" or "alters" is intended to describe both the upregulation or downregulation of a process, since, as is well known to a skilled artisan, a process which is upregulated by a certain stimulant may be inhibited by an antagonist to that stimulant. Conversely, a process that is downregulated by a certain stimulant may be inhibited by an antagonist to that stimulant. Thus, e.g., the identification of an agent that induces a cellular response modulates or alters cellular behavior in an inductive manner and it is inherently understood that the response may be modulated in an inhibitory manner by an inhibitor of that agent (e.g., by an antibody or antisense RNA, as is well understood and described in the art).

The term "nucleic acid" as used herein refers to polynucleotides or oligonucleotides such as deoxyribonucleic acid (DNA), and, where appropriate, ribonucleic acid (RNA). The term should also be understood to include, as equivalents, analogs of either RNA or DNA made from nucleotide analogs and as applicable to the embodiment being described, single (sense or antisense) and double-stranded polynucleotides.

The term "physical finding," as the term is used herein, refers to any sign or symptom that is elicitable during the face-to-face evaluation of a patient by a health care provider. A physical finding then may include a symptom, such as pain, described by the patient during medical history-taking. A physical finding may refer to those features of the patient's anatomy identified during the observation, auscultation, percussion or palpation of the patient's body. A physical finding may also refer to those aspects of the patient's anatomy that are discerned by observation, auscultation, percussion or palpation amplified by instrumentation directly manipulated by the health care provider, instrumentation such as endoscopes, stethoscopes, otoscopes and fundoscopes. Other, more sophisticated instruments for observation, such as slit lamps, are capable of discerning "physical findings," as the term is used herein. Within the scope of this invention are those findings produced by amplifying the observational capacity of the health care provider during the direct encounter with the patient. For example, administering fluoroscein and observing its effect on a tissue with a slit lamp at a preselected wavelength would result in the determination of a set of physical findings, as the term is used herein. Other types of physical findings consistent with this definition will be readily apparent to practitioners of ordinary skill in the relevant arts. Physical findings for aortic aneurysms could include, for example, a pulsatile abdominal mass, a tender abdominal mass, back pain, alteration of peripheral pulses or an abdominal bruit.

The term "polymorphism" refers to the coexistence of more than one form of a gene or portion (e.g., allelic variant) thereof. A portion of a gene of which there are at least two different forms, i.e., two different nucleotide sequences, is referred to as a "polymorphic region of a gene". A polymorphic region can be a single nucleotide, the identity of which differs in different alleles. A polymorphic region can also be several nucleotides long. A "polymorphic gene" refers to a gene having at least one polymorphic region.

The terms "protein", "polypeptide" and "peptide" are used interchangeably herein when referring to a gene product comprising amino acids. The term "recombinant protein" refers to a polypeptide of the present invention which is produced by recombinant DNA techniques, wherein generally DNA encoding a polypeptide is inserted into a suitable expression vector which is in turn used to transform a host cell to produce the heterologous protein. Likewise the term "recombinant nucleic acid" or "recombinant DNA" refers to a nucleic acid or DNA of the present invention which is produced by recombinant DNA techniques, wherein generally DNA encoding a polypeptide is inserted into a suitable expression vector which is in turn used to transform a host cell to produce the heterologous protein. Moreover, the phrase "derived from", with respect to a recombinant gene, is meant to include within the meaning of "recombinant protein" those proteins having an amino acid sequence of a native polypeptide, or an amino acid sequence similar thereto which is generated by mutations including substitutions and deletions (including truncation) of a naturally occurring form of the polypeptide.

A "radiological finding," as used herein, refers to any digital or graphic representation resulting from the diagnostic administration of a dose of electromagnetic radiation or sound waves to a patient. A radiological finding would include the output of tests such as MRI, CT scan, IV contrast angiography, conventional XRay, ultrasound, echocardiography, doppler angiography, or radionuclide scans. Other types of radiological findings will be apparent to practitioners of ordinary skill in the medical arts. Radiological findings consistent with a AAA might include, for example, calcification on lateral lumbosacral spine films, a mass discernible on ultrasound, or a characteristic appearance of the infrarenal aorta on angiography, CT scan or MRI.

"Small molecule" as used herein, is meant to refer to a composition which has a molecular weight of less than about 5 kD and most preferably less than about 4 kD. Small molecules can be nucleic acids, peptides, polypeptides, peptidomimetics, carbohydrates, lipids (e.g., glycolipids and pig-tail lipids) or other organic (carbon containing) or inorganic molecules. Many pharmaceutical companies have extensive libraries of chemical and/or biological mixtures, often fungal, bacterial, or algal extracts, which can be screened with any of the assays of the invention to identify therapeutic compounds.

A "therapeutic" as used herein refers to an agonist or antagonist of the bioactivity of a drusen associated marker. Preferred therapeutics reduce or inhibit RPE cell death, factors involved in the inflammatory response, factors involved in fibroblast proliferation and migration resulting in fibrosis and/or dendritic cell proliferation, migration or differentiation into drusen. Other preferred therapeutics include agents that have shown some efficacy in treating or preventing aortic diseases (e.g. AAA), including: antiinflammatory agents (e.g. anti CD-18 antibody), protease inhibitors, inhibitors of elastolytic MMPs (e.g. the hydroxamate based RS312908, batimastat, antibiotics (e.g. doxycycline), tetracycline), inhibitors of prostaglandin synthesis and beta-blockers (e.g. propanalol).

The term "transcriptional regulatory sequence" is a generic term used throughout the specification to refer to DNA sequences, such as initiation signals, enhancers, and promoters, which induce or control transcription of protein coding sequences with which they are operably linked.

As used herein, the term "transfection" means the introduction of a nucleic acid, e.g., via an expression vector, into a recipient cell by nucleic acid-mediated gene transfer. "Transformation", as used herein, refers to a process in which a cell's genotype is changed as a result of the cellular uptake of exogenous DNA or RNA.

As used herein, the term "transgene" means a nucleic acid sequence (encoding, e.g., one of the polypeptides of the invention, or an antisense transcript thereto) which has been introduced into a cell. A transgene could be partly or entirely heterologous, i.e., foreign, to the transgenic animal or cell into which it is introduced, or can be homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout or may result in over expression). A transgene can also be present in a cell in the form of an episome. A transgene can include one or more transcriptional regulatory sequences and any other nucleic acid, such as 5' UTR sequences, 3' UTR sequences, or introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to fail to express a specific normal gene product, to express a recombinant form of one or more DRAM polypeptides, e.g., either agonistic or antagonistic forms, or molecules that regulate the biosynthesis, accumulation or resorption of DRAMs or dendritic cells. Transgenic knockouts may, for example, be produced which cause alterations in dendritic cell behavior (e.g., cell growth, proliferation, migration, differentiation or gene expression). For example, mice whose Rel-B, transforming growth factor b1 (TGF-b1) or Ikaros genes are disrupted lack dendritic cells from various cell lineages (see Caux, C. et al., 1999). However, transgenic animals in which the recombinant DCRM or DRAM gene is silent are also contemplated, as for example, the FLP or CRE recombinase dependent constructs. Moreover, "transgenic animal" also includes those recombinant animals in which gene disruption is caused by human intervention, including both recombination and antisense techniques.

The term "treating" or "treatment" as used herein is intended to encompass curing as well as ameliorating at least one symptom of the condition or disease. As applied to an aneurysm, for example, "treating" may refer to preventing the expansion of an existent aneurysm, or to increasing the structural stability of the wall of the aneurysmal artery.

The terms "vector," "cloning vector," or "replicative cloning vector," are interchangeable as used herein, and refer to a nucleic acid molecule, which is capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors." The term "expression system" as used herein refers to an expression vector under conditions whereby an mRNA may be transcribed and/or an mRNA may be translated into protein. The expression system may be an in vitro expression system, which is commercially available or readily made according to art known techniques, or may be an in vivo expression system, such as a eukaryotic or prokaryotic cell containing the expression vector. In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as a plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

4.2: Pathophysiology of Macular Degeneration and Arterial Wall Disruptive Disorders In one embodiment, the methods and kits of the present invention rely upon the novel discovery disclosed herein that there are significant pathophysiological and biological similarities between those patients afflicted with AMD and those patients afflicted with arterial wall disruptive disorders, in particular AAA. Some of these similarities are summarized below.

| AAA/AMD Similarities | | |
|---|---|---|
| AAA Features | AMD | Data Support |
| Heritable | X | |
| Age-related | X | |
| Elastin destruction & other ECM | X | University of Iowa data |
| Collegen and elastin neosynthesis | X | University of Iowa data |
| Exacerbated by hypertension | ? | |
| Smoking as a risk factor | X | |
| Autoimmune involvement | ? | University of Iowa data |
| Aortic neovascularization | X | |
| Assoc. with atherosclerosis | X | |
| Potential assoc. with COPD | ? | University of Iowa data |
| Loss of vascular smooth muscle cells | ? | University of Iowa data |
| Influx of dendritic cells | X | University of Iowa data |
| Chronic inflammation (subset) | ? | University of Iowa data |
| Upregulation of MMP2 & MMP9, t-PA, uPA, PAI-1, C3, IgG, TNFX, IL1, IL6, IL8 | X | |
| Downreg. of TIMP, GAG, PG | ? | |
| Assoc. with alpha-1 antitrypsin deficiency (subset) | ? | University of Iowa data |

Certain of these associations are supported by data presented in more detail in the Examples incorporated herein. Other associations not specified above will be readily apparent to practitioners of ordinary skill in the relevant arts. The descriptions presented below of the disease processes of macular degeneration and arterial wall disruptive disorder will allow the ordinarily skilled practitioner to determine, with no more than routine experimentation, other associations between these disease processes that will fall within the scope of the present invention.

4.2a: Macular Degeneration 4.2a(i) General

Macular degeneration is a clinical term that is used to describe a variety of diseases that are all characterized by a progressive loss of central vision associated with abnormalities of Bruch's membrane, the neural retina and the retinal pigment epithelium (RPE). These disorders include very common conditions that affect older patients (age related macular degeneration or AMD) as well as rarer, earlier-onset dystrophies that in some cases can be detected in the first decade of life (Best F. Z., *Augenheilkd.*, 13:199–212, 1905; Sorsby, A., et al., *Br J. Opthalmol.* 33:67–97, 1949; Stargardt, K., *Albrecht Von Graefes Arch Klin Exp Opthalmol.* 71: 534–550, 1909; Ferrell, R. E., et al., *Am J. Hum Genet.* 35:78–84, 1983; Jacobson, D. M., et al., *Ophthalmology,* 96:885–895, 1989; Small, K. W., et al. *Genomics* 13:681–685, 1992; Stone, E. M., et al., *Nature Genet.* 1:246–250, 1992; Forsman, K., et al. *Clin Genet.* 42:156–159, 1992; Kaplan, J. S., et al. *Nature Genet.* 5:308–311, 1993; Stone, E. M., et al. *Arch Opthalmol.* 112:763–772, 1994; Zhang, K., et al. *Arch Opthalmol.* 112:759–764, 1994; Evans, K., et al. *Nature Genet.* 6:210–213, 1994; Kremer, H., et al. *Hum Mol Genet.* 3:299–302, 1994; Kelsell, R. E., et al. *Hum Mol Genet.*

4:1653–1656, 1995; Nathans, J., et al. *Science* 245:831–838, 1989; Wells, J., et al. *Nature Genet.* 3:213–218, 1993; Nichols, B. E., et al. *Nature Genet.* 3:202–207, 1993a; Weber, B. H. F., et al. *Nature Genet.* 8:352–355, 1994). Macular degeneration diseases include, for example, Age Related Macular Degeneration, North Carolina macular dystrophy, Sorsby's fundus dystrophy, Stargardt's disease, pattern dystrophy, Best disease, malattia leventinese, Doyne honeycomb choroiditis, dominant drusen and radial drusen.

Histopathologically, the condition is characterized by accumulation of membranous debris on both sides of the retinal pigment epithelium (RPE) basement membrane. Pathophysiological hallmarks include the formation of drusen, atrophy of the RPE/choriocapillaris, RPE detachment, and choroidal new vessel (CNV) formation. Histopathologic studies have documented significant and widespread abnormalities in the extracellular matrices associated with the RPE, choroid, and photoreceptors of aged individuals and of those with clinically-diagnosed AMD (Sarks, 1976; Sarks, et al., 1988; Bird, 1992a; van der Schaft, et al., 1992; Green and Enger, 1993; Feeney-Burns and Ellersieck, 1985; Young, 1987; Kincaid, 1992). The most prominent extracellular matrix (ECM) abnormality is drusen, deposits that accumulate between the RPE basal lamina and the inner collagenous layer of Bruch's membrane (FIG. 1). Drusen appear to affect vision prior to the loss of visual acuity; changes in color contrast sensitivity (Frennesson, et al., 1995; Holz, et al., 1995b; Midena, et al., 1994; Stangos, et al., 1995; Tolentino, et al., 1994), macular recovery function, central visual field sensitivity, and spatiotemporal contrast sensitivity (Midena, et al., 1997) have been reported.

Drusen also cause a lateral stretching of the RPE monolayer and physical displacement of the RPE from its immediate vascular supply, the choriocapillaris. This displacement creates a physical barrier that may impede normal metabolite and waste diffusion between the choriocapillaris and the retina. It is likely that wastes may be concentrated near the RPE and that the diffusion of oxygen, glucose, and other nutritive or regulatory serum-associated molecules required to maintain the health of the retina and RPE are inhibited. It has also been suggested that drusen perturb photoreceptor cell function by placing pressure on rods and cones (Rones, 1937) and/or by distorting photoreceptor cell alignment (Kincaid, 1992).

The terminology most commonly used to distinguish drusen phenotypes is hard and soft (see, for example, Eagle, 1984; Lewis, et al., 1986; Yanoff and Fine, 1992; Newsome, et al., 1987; Mimoun, et al., 1990; van der Schaft, et al., 1992; Spraul and Grossniklaus, 1997), although numerous phenotypes exist (Mullins and Hageman, Mol. Vision, 1999). Hard drusen are small distinct deposits comprised of homogeneous eosinophilic material. Histologically, they are round or hemispherical, without sloped borders. Soft drusen are larger and have sloped, indistinct borders. Unlike hard drusen, soft drusen are not usually homogeneous, and typically contain inclusions and spherical profiles. An eye with many large/soft drusen is at a significantly higher risk of developing complications of AMD than is an eye with no drusen or a few, small drusen. The term "diffuse drusen," or "basal linear deposit," is used to describe the amorphous material which forms a layer between the inner collagenous layer of Bruch's membrane and the RPE. This material can appear similar to soft drusen histologically, with the exception that it is not mounded.

Our knowledge of drusen composition, especially as it relates to phenotype, is scant. Wolter and Falls (1962) observed that drusen stain with oil red 0, indicating the presence of neutral lipids in at least some drusen. Pauleikhoff, et al. (1992) used lipid-based histochemical staining approaches to show that different phenotypes of drusen contain either phospholipids or neutral lipids. These "hydrophilic" drusen were also bound by an anti-fibronectin antibody. Pauleikhoff et al. (1992) concluded that phospholipid-containing, but not neutral lipid-containing, drusen were anti-fibronectin antibody-reactive. Other investigators have not been able to reproduce the observation of an association of fibronectin with drusen (van der Schaft, et al., 1993; Mullins et al., 1999). These data suggest that drusen are either hydrophobic or hydrophilic, and that different drusen classes may indicate significantly different pathologies, suggesting the existence of different compositional classes of drusen, not solely based on morphology (i.e., hard and soft).

Farkas, et al. (1971b) analyzed drusen composition by enzymatic digestion, organic extraction, and histochemical staining methods for carbohydrates and other molecules. They concluded that drusen are comprised of sialomucins (glycoproteins with O-glycosidically-linked oligosaccharides) and cerebrosides and/or gangliosides.

Newsome et al. (1987) described labeling of soft drusen with antibodies directed against fibronectin, and to hard and soft drusen with antibodies directed against IgG and IgM. In addition, weak labeling of drusen with antibodies directed against beta amyloid (Loeffler, et al., 1995) and complement factors (C1q, C3c, C3d, and C4) (van der Schaft, et al., 1993), and more intense labeling with antibodies directed against ubiquitin (Loeffler and Mangini, 1997) and TIMP-3 (Fariss, et al., 1997), has been reported. Antibodies to other ECM molecules, including collagen types I, III, IV, and V, laminin, and heparan sulfate proteoglycan, have also been reported as being components of drusen in "diffuse, mottled or superficial laminar" patterns (Newsome, et al., 1987).

Discrepancies between the results of the immunohistochemical studies described above are likely due to disagreement upon a universal classification system for drusen, the use of dehydrated, paraffin-embedded tissues (which potentially resulting in the extraction of some drusen constituents) as opposed to frozen sections, and the use of antibodies directed against different epitopes of the same protein. Additionally, the use of tissues that are fixed or frozen within a short period after death reduces false negatives (due to post-mortem autolysis and loss of antigenicity) and false positives (due to post-mortem diffusion and loss of physiologic barriers).

In addition to the lipid, protein and carbohydrate composition of drusen, several investigators have identified plasma membrane or cellular organelles in drusen. Farkas et al. (1971 a) described the presence of numerous degenerating organelles in drusen, including what appeared to be lysosomes. Based on the observation that similar material was present on the RPE side of Bruch's membrane prior to drusen formation, they suggested that drusen constituents were derived from the RPE. However, lysosomal enzyme activity within drusen has not been verified (Feeney-Burns, et al., 1987). Burns and Feeney-Burns (1980) described the presence of "cytoplasmic debris" in small drusen, which they inferred was derived from the RPE. Feeney-Burns and Ellersieck (1985) later described a paucity of debris in Bruch's membrane directly beneath drusen, and suggested that drusen may result from an inability of the choroid to clear debris from sites of drusen deposition.

Drusen contain a number of drusen-associated molecules (DRAMs), including amyloid A protein, amyloid P component, antichymotrypsin, apolipoprotein E, $\beta 2$ microglobulin, complement 3, complement C5, complement C5b-9 terminal complexes, factor X, fibrinogen, immunoglobulins (kappa and lambda), prothrombin, thrombospondin or vitronectin.

A comprehensive understanding of drusen biogenesis is lacking. At least twelve pathways for drusen genesis have been suggested in the literature (Duke-Elder and Dobree, 1967; Wolter and Falls, 1962; Ishibashi, et al., 1986a). These fall into two general categories based on whether drusen are derived from the RPE or the choroid. Theories related to the derivation of drusen from RPE cells include the concepts that: drusen result from secretion of abnormal material derived from RPE or photoreceptors ("deposition theories"—Muller, 1856; Ishibashi, et al., 1986; Young, 1987); transformation of degenerating RPE cells into drusen ("transformation theories"—Donders, 1854; Rones, 1937; Fine, 1981; El Baba, et al., 1986) or some combination of these pathways. Specifically, some investigators have concluded, based on ultrastructural data, that drusen are formed when the RPE expels its basal cytoplasm into Bruch's membrane (Ishibashi, et al., 1986a), possibly as a mechanism for removing damaged cytosol (Burns and Feeney Burns, 1980). However, very few convincing images of this process have been demonstrated. Others have postulated that drusen are formed by autolysis of the RPE, due to aberrant lysosomal enzyme activity (Farkas, et al., 1971 a), although more recent enzyme histochemical studies have failed to demonstrate the presence of lysosomal enzymes in drusen (Feeney-Burns, et al., 1987). Other mechanisms, including lipoidal degeneration of the RPE (Fine, 1981) and a derivation from vascular sources (Friedman, et al., 1963) have also been postulated (summarized in Duke-Elder and Dobree, 1967).

Duvall et al. (1985) suggested a role for choroidal pericytes in keeping Bruch's membrane clear of debris. They suggested that dysfunction of pericytes leads to the formation of drusen, either by the accumulation of material from the choroid or by the failure to remove material deposited by the RPE. Killingsworth et al. (1990) described macrophages participating in the breakdown of Bruch's membrane in the neovascular stage of AMD and in drusen regression, and show one electron micrograph depicting structures resembling drusen cores. Duvall and Tso (1985) showed choroidal macrophages in the region of the Bruch's membrane are involved in the removal of drusen in monkey eyes, following laser photocoagulation. Penfold and others (Penfold et al., 1985; Penfold et al., 1986; Oppenheim and Leonard, 1989) provided "circumstantial evidence . . . for the involvement of (choroidal) leukocytes, in the promotion of neovascular proliferation." However, these data were restricted to morphological observations only. Based on those observations investigators suggested that macrophages participate in the neovascularization stage of drusen formation.

Changes related to AMD that are observed in the fundus may vary with different AMD phenotypes. At least ten distinct AMD fundus patterns have been identified at the University of Iowa that may be termed "The University of Iowa AMD/Drusen Classification." Certain fundus patterns may correlate with particular arterial wall disruptive disorders; for example, a certain pattern may be identified that correlates with an increased likelihood of developing a AAA or of having expansion occur in an established AAA, while other fundus patterns may be indicative of an increased likelihood of developing a TAAA or a dissecting TAA. The different fundus patterns, like the different forms of arterial wall disruptive disorders, may correlate with different underlying genetic patterns.

4.2a(ii) Working Hypothesis of Drusen Biogenesis

Proposed herein is a unifying theory of drusen biogenesis that attempts to incorporate a large body of new and previously published data generated in this, and other, laboratories. This theory is put forth with the acknowledgment that numerous AMD genotypes may exist. Thus, only some aspects of the proposed hypothesis may be involved in any given AMD genotype. Importantly, the theory is based upon novel data generated in this laboratory documenting that dendritic cells are associated with drusen. This observation invokes, for the first time, the potential for a direct role of cell-mediated processes in drusen biogenesis. Thus, we believe that any working hypothesis pertaining to drusen biogenesis and the etiology of drusen associated ocular diseases must include a role for dendritic cells.

The presence of dendritic cells in inflammatory lesions is well-recognized. It is clear that dendritic cells must be recruited, activated, and migrate to, sites of inflammation, rather than passively migrating to these sites. Dendritic cells are typically recruited to sites of tissue damage by various chemoattractants, heat shock proteins, DNA fragments, and others. Choroidal dendritic cell processes are associated with the smallest of drusen, and are often observed in the sub-RPE space in association with whole, or portions of, RPE cells that have been shunted into Bruch's membrane, prior to the time that drusen, per se, are detectable. Based on these observations, proposed herein is a mechanism in which choroidal dendritic cells are activated and recruited by locally damaged and/or sublethally injured RPE cells. This idea is consistent with recent data showing that dendritic cells, and thus the innate immune system, can be activated by microenvironmental tissue damage. In this state, these cells extend a cellular process through Bruch's membrane in order to gain access to the site of tissue damage. In this role, choroidal dendritic cells may thus serve as sentinel receptors with the capacity to respond to local cell injury, and ultimately provide for the overall integration of immune-mediated processes that determine the outcome of the overall response.

In this model, the injured RPE itself (by whatever mechanism this occurs) may serve as a source of soluble cytokines or other stimulatory factors that initiate dendritic cell recruitment and activation. The data presented herein clearly supports accelerated RPE cell death in eyes derived from donors with AMD, as compared to age-matched controls. Based on available information from other systems, and upon previous suggestions pertaining to the etiology of AMD, RPE cell death might occur by several mechanisms, including ischemia, necrosis, gene-mediated injury, Bruch's membrane-induced dysfunction, oxidative injury from light or systemic factors (e.g. smoking-generated compounds), lipofuscin accumulation, or autoimmune phenomena, to list a few. Based on existing data, it is likely that RPE cell death would most likely have to be due to necrosis, rather than to apoptosis, since cells undergoing apoptotic cell death do not recruit dendritic cells. Indeed, the data provides compelling evidence for an absence of apoptotic RPE cell death in human donor eyes.

Several known pathways can initiate receptor-ligand interactions between dendritic cell precursors and injured tissue. These include cytokines such as IL-1, IL-6, IL-12, TNF-alpha, and GM-CSF, heat shock proteins, altered expression of cell surface proteins and DNA in the presence of free radicals. The novel observation of clonal expression of HLA-DR, CD68, vitronectin, S-100, clusterin, and apolipoprotein E by RPE cells in eyes from donors with drusen may be particularly significant in this respect. Furthermore, up-regulation of various cell death- and immune-associated molecules by the RPE/choroid in eyes with developing drusen and AMD have been identified using differential display and gene array analyses. In addition, there is evidence that free radicals, which are known to be present in high concentrations at the RPE-retina-choroid interface, might be immunostimulatory. There is also data suggesting that ceroid (a potential component of lipofuscin) derived from necrotic cells may serve as an antigen in the generation of certain autoimmune diseases. This could explain the general contention that oxidative stress and/or lipofuscin may lead to RPE dysfunction and the development of AMD (Mainster, M. A., *Light and macular degeneration: a biophysical and clinical perspective.* Eye, 1987. 1(Pt 2): p. 304–10).

Once inside the lesion (a.k.a. the drusen), dendritic cells might then contribute to the chronicity (induced chronic inflammatory lesions) of AMD by any number of mechanisms, including immune complex formation, complement activation, and/or in situ activation of choroidal T-cells, other phagocytic cells, and matrix proteolysis. The presence of numerous immune-associated constituents in drusen, including immunoglobulins, complement proteins, and some acute phase proteins, could be explained by such an event. One might predict that the dendritic cell response would be down-regulated once the local tissue damage has been repaired, thus restoring tolerance. This type of self-limiting control is typically accomplished in other systems via turnover of dendritic cells; the influx of new dendritic cell precursors and the concomitant reduction in the influx of mature dendritic cells into the lymph nodes is typically sufficient to shift the balance back to tolerance. In other cases, natural killer cells recognize mature dendritic cells as targets, providing a negative feedback effect on antigen presentation, forcing the system into tolerance. However, in the case of AMD, we suggest that a state of chronic inflammation persist for many years. In this scenario, cyclical events of RPE cell death may occur over a period of many years that do not allow the system to return to tolerance. In one example, this might occur as a result of genetic preprogramming, as in the case of a RPE gene mutation. In another example, local activation of complement and HLA-DR expression by RPE cells, initiated by dendritic cells recruited to the sub-RPE region, might lead to clonal RPE cell death, thereby maintaining a state of chronic inflammation. Other scenarios can certainly be envisioned and must be tested. A negative outcome of this entire process may be that Bruch's membrane and the surrounding extracellular matrix may be degraded, angiogenic factors may be generated, resulting in opportunistic neovascularization of the sub-RPE and subretinal spaces. Although there is little information in the literature concerning matrix-degrading enzyme expression by dendritic cells. However, MT-1-MMP expression within drusen cores has been observed, suggesting a possible mechanism for DC-mediated matrix breakdown.

The notion that dendritic cells may be activated by local tissue injury might also initiate an autoimmune response to retinal and/or RPE antigens that are uncovered during tissue damage. The availability and amount of RPE debris/antigen will most likely determine which ensuing pathway is involved. Such autoimmune responses have been documented as a consequence of ischemia or injury to the heart and we have recently identified autoantibodies in the sera of individuals with AMD that are directed against retinal and RPE proteins of 35 kDa and 53 kDa. This might occur as a consequence of aberrant delayed-type hypersensitivity responses, perhaps explaining the presence of serum autoantibodies in at least some AMD patients. It is also conceivable that the groundwork for this process is primed earlier in life by necrosis of RPE cells, potentially explaining the consequence of the wave of peripheral RPE cell dropout we have observed in the second and third decades of life in preliminary studies.

In the model presented herein, the initiating RPE injury event is followed by the continued deposition of drusen-associated constituents. Early DRAM-matrix complexes, such as immune complexes, or other local ligands might serve as "nucleation sites" for the deposition of additional self-aggregating proteins and/or lipids. These constituents could be derived from either the plasma and/or local cellular sources. Based on the knowledge that many DRAMs are circulating plasma proteins, it is plausible that some DRAMs pass out of choroidal vessels and into the extracellular space adjacent to the RPE where they bind to one or more ligands associated with Bruch's membrane in the aging eye. These ligands could be basement membrane components, plasma membrane receptors, secretory products derived from RPE or choroidal cells, or byproducts of cellular autolysis. As reported herein, a number of drusen-associated molecules, including apolipoprotein E, vitronectin, fibrinogen, C reactive protein, and transthyretin, have been synthesized by the RPE and/or retina. Although unexpected, these data support the concept that some DRAMs may be synthesized and secreted locally. It remains to be determined whether up- or down-regulation of DRAM synthesis by local cells correlates with drusen deposition and/or AMD. As these abnormal deposits increase in size they displace the RPE monolayer and are recognized clinically as drusen.

This model might also predict an imbalance in extracellular matrix synthesis, degradation, and/or turnover, thereby leading to events such as choroidal neovascularization, a hallmark characteristic of some forms of AMD, cellular proliferation, cellular differentiation, and interstitial fibrosis. In many organs, fibrogenesis is a common complication of tissue injury, independent of the initial site of said injury. The recruitment of immune cells, and their activation and/or modulation by resident cells, represents a key step in the cascade of events that ultimately lead to fibrosis. Recent studies also suggest that distinct functional fibroblast phenotypes may play a central role in early fibrosis, including the recruitment of immune cells.

Choroidal fibrosis has been documented in a subset of donor eyes. There is a significant correlation between choroidal fibrosis and age. Furthermore, preliminary data suggest that there is a strong correlation between choroidal fibrosis and AMD, aortic aneurysms, aortic stenosis, and possibly COPD. These choroids are characterized ultrastructurally by massive accumulations of newly synthesized collagen and elastin fibrils, as well as filamentous collagens and microfilaments, that fill the normally loosely packed choroidal stromas. The major collagen fibrils average 0.042–0.063 μm in diameter as compared to the fibrillar collagen in the sclera, which averages 0.211–0.253 μm in diameter. Furthermore, the collagen fibrils in these donors exhibit a classic spiraled morphology in longitudinal and cross sections. It is thought that spiraled collagen results from disaggregation of fibrils and/or to incorporation of uncleaved procollagen molecules. This collagen phenotype is observed in a few heritable connective tissue diseases (Ehler's-Danlos; PXE; dermatoparaxis), as well as in other conditions (collagenofibrotic glomerulopathy, scleroderma, atherosclerosis, amyloid, emphysema, atheromatous plaques). Clear indications of active elastin synthesis (including dilated RER, pockets of microfilaments, and elastin exhibiting the morphological characteristics of newly synthesized protein) are also observed along attenuated fibroblast cell processes and interspersed amongst the collagen fibrils.

A hypothetical pathogenic sequence of events consistent with known data is: 1) RPE dysfunction (e.g., precipitated by an inherited susceptibility and/or environmental exposure); 2) accumulation of intracellular material in the RPE (e.g., accumulation of normal substrate material that is not enzymatically degraded properly vs. abnormal substrate material); 3) abnormal accumulation of extracellular material (basal laminar and basal linear deposit); 4) change in Bruch's membrane composition (e.g., increased lipid deposition and protein crosslinking); 5) change in Bruch's membrane permeability to nutrients (e.g., impaired diffusion of water soluble plasma constituents across Bruch's membrane); and 6) response of the RPE to metabolic distress (i.e., atrophy vs. CNV growth). Histopathological and clinical studies indicate that areas of choroidal ischemia often are seen near CNVs in AMD patients. In response to decreased oxygen delivery/metabolic "distress", the RPE may elaborate substances leading to CNV growth. Perhaps RPE atrophy, followed by choriocapillaris and photoreceptor atrophy, is a response to decreased nutrients/increasing metabolic abnormalities in areas of excessive accumulation of extracellular debris. Unanswered questions regarding AMD include: 1) is AMD an ocular manifestation of a systemic disease or purely an ocular disease?; 2) what determines whether CNVs vs. atrophy of the RPE-choriocapillaris-photoreceptors develops?; and 3) what induces the maturation of CNVs into an inactive scar, and what limits the growth of most CNVs to the area centralis?

Since drusen share a number of molecular constituents in common with abnormal deposits associated with a variety of other age-related diseases, drusen may represent an ocular manifestation of amyloidosis, elastosis, dense deposit disease, and/or atherosclerosis. Although modulated by different genes and/or environmental influences, all these diseases give rise to similar yet distinguishable pathological phenotypes by triggering a similar set of biological responses that include inflammation, coagulation, and activation of the immune system. Thus, the invention provides a valuable recognition of these similarities as compared to other age-related diseases which manifest themselves in deposits or plaques.

4.2b: Arterial Wall Disruptive Disorders

Arterial wall disruptive disorders may affect the abdominal aorta, resulting in the formation of abdominal aortic aneurysm (AAA). AAA are a form of arterial wall disruptive disorders entailing aneurysm formation in the aortic wall that is localized within the abdomen. AAA are therefore a form of aortic wall disruptive disorders. These lesions are becoming increasingly common in developed countries including the United States, Australia, and Europe. (MacSweeney et al., *Brit J. Surg.* 81:935–941, 1994). The prevalence of AAA is approximately 6% (2–9%) in the general population and primarily affects individuals over the age of about 65. (Wilmink, A. B. and Quick, C. R., *Brit. J. Sur.*, 85:152–162, 1998). Because the size of the population over the age of 65 continues to increase, AAA and other arterial wall disruptive diseases will likely place a great burden on health resources in the near future.

Aortic wall disruptive disorder also includes aneurysms of the thoracic aorta. These aneurysms generally have a component extending below the diaphragm, so are more accurately termed thoracoabdominal aortic aneurysms (TAAA). They are classified according to their anatomic extent. (Crawford E S et al., "Thoracoabdominal aortic aneurysms: preoperative and intraoperative factors determining immediate and long-term results of operations in 605 patients," J. Vasc. Surg. 3:389–404, 1986). Thoracic aortic aneurysms without dissection may be caused by a number of factors, including atherosclerotic medial degenerative disease, congenital disorders such as Marfan's and Ehlers-Danlos syndromes, mycotic lesions and Takayasu's aortitis. Aortic wall disruptive disease further includes aortic dissections, whether or not they are associated with aneurysm formation. Atherosclerotic medial degenerative disease (82%) and dissection (17%) are responsible for over 95% of all TAAA. (Panneton J M et al., "Nondissecting thoracoabdominal aortic aneurysms: Part I," Vasc. Surg. 9:503–514, 1995). Hypertension is commonly found in both groups of TAAA patients. Patients with degenerative (atherosclerotic) aneurysms, however, tend to have a higher incidence of coronary artery disease, chronic renal insufficiency, cerebrovascular disease and peripheral vascular disease.

While it is understood herein that the systems, methods and kits of the present invention are related to arterial well disruptive disorders in all anatomic locations, the present invention will be illustrated with particular reference to the disruptive disorder of the aortic wall that culminates in AAA or in TAAA.

4.2b(i) Anatomy of the Arterial Wall

Arteries are divided into three general categories based on the anatomy of their walls: large elastic arteries, medium muscular arteries and small arteries. All arteries possess three layers, the intima, the media and the adventitia. The media, bounded by the internal and the external elastic laminae, contains smooth muscle cells embedded in a matrix of collagen, elastin and proteoglycans. The adventitia, lying outside the external elastic lamina, is composed of loose connective tissues, fibroblasts, capillaries, leukocytes and small nerve fibers. The arterial wall is nourished by a system of blood vessels called vasa vasorum.

The large elastic arteries of the body include the aorta and its major branches. The medium muscular arteries include most of the distributing vessels to the organs. These two classes of arteries differ primarily in the amount of elastic tissue present in the media. In the aortic wall there are well-defined lamellar units consisting of commonly oriented and elongated smooth muscle cells and their surrounding matrix. The matrix includes a meshwork of collagen and a layer of elastin. (Clark J M et al., "Transmural organization of the arterial media: the lamellar unit revisited," Arteriosclerosis 5:19, 1985). The lamellar unit represents the structural and functional unit of the aortic wall. The lamellar unit consists of layers of smooth muscle cells interspersed with clearly defined lamellae of elastin. Tropoelastin monomers are normally produced by fibroblasts and vascular smooth muscle cells (SMCs) and deposited onto a microfibrillar network of fibrillin and other proteins, and cross-linked by lysyl oxidase to form mature elastic fibers, which are arranged in concentric lamellae.

4.2b(ii) Genetics of AAA

A familial tendency to develop aneurysms is well documented in about 15–20% of patients with AAA, suggesting a genetic predisposition to AAA in some patients, a positive family history in a first-degree relative being a significant risk factor for developing AAA. (MacSweeney et al., *Brit J.*

*Surg.* 81:935–941, 1994). The most likely explanation for the occurrence of AAA in families is a single gene showing dominant inheritance and low penetrance. (Verloes, A., et al., *J. Vasc. Surg.* 21:646–655, 1995). Familial associations for other aneurysms have also been noted. (Kojima M, et al., "Asymptomatic familial cerebral aneurysms", Neurosurgery, 43(4):776–81 1998 Oct). Familial clustering has been observed for inflammatory aneurysms, correlated with the identification of an HLA-DR B 1 allele in a cohort of those patients. (Rasmussen T E, et al., "Genetic risk factors in inflammatory abdominal aneurysms: polymorphic residue 70 in the HLA-DR B1 gene as a key genetic element," J Vasc Surg, 25(2):356–64 1997 Feb). Genetic factors have been associated with development of other aneurysmal syndromes, in one case associating a fibrillin genotype, blood pressure and aneurysm formation. (Powell J T, et al., "Interaction between fibrillin genotype and blood pressure and the develop aneurysmal disease," Ann NY Acad Sci, 800(-HD-): 198–207 1996 Nov. 18).

Attempts to define the genetic component(s) underlying AAA have used a variety of strategies, including both linkage analysis and candidate gene approaches. Several candidate genes for AAA, including collagen, α1-antitrypsin, fibulin-2 (Kuivaniemi et al., Eur. J. Hum. Gen 6:642–646, 1999), proteolytic enzymes, tissue inhibitors of metalloproteases (TIMPs) and haptoglobin have been investigated to explain the familial clustering of AAA. Significantly, polymorphisms in the elastin gene have not been demonstrated in patients with AAA. Genetic mutations in fibrillin-1 and type III procollagen have been found to be responsible for aneurysm development in a small number of patients (e.g., in Marfan's syndrome and Ehler-Danlos syndrome, respectively). A mutant gene for the alpha chain of type III collagen co-segregates with aneurysmal disease in 3 out of 50 families, and a single base mutation at position 619 in collagen type III has been described in one family. (Kontusaari, S. et al., *Ann. N.Y. Acad. Sci.*, 580:556–557, 1990). About 2% of aortic aneurysms are thought to be caused by a gly136-to-arg mutation in the type III procollagen gene. (Tromp, G. et al., *J. Clin. Invest.*, 91:2539–2545). A deficiency allele for α1-antitrypsin was found in 5 out of 47 patients and a nucleotide substitution for TIMP(1) was found in 2 out of 6 patients. A mutation in the COL3A1 gene has been implicated in the pathogenesis of some familial aortic aneurysms. (Reviewed in Kuivaniemi, H. et al., *J. Clin. Invest.* 88:1441–1444, 1991). The MZ-α1-antitrypsin phenotype has been found with increased frequencies in individuals with AAA. (Cohen, J. R. et al., *J. Surg. Res.* 49:319–321, 1990). Another study suggested that AAA may be associated with the 2-1 and 1-1 genotypes of haptoglobin. (Norrgard, O., *Hum. Hered.* 34:166–169, 1984). Taken together, available data suggest that, while AAA may be inherited in many cases, the gene or genes responsible for most cases of AAA remain to be identified.

4.2b(iii) Other AAA Risk Factors

Aside from the undefined genetic component, the etiology of AAA is currently thought to arise through a complex interaction among various risk factors including atherosclerosis, aging, autoimmune processes, gender, race, cigarette smoking and hypertension. Severe intimal atherosclerosis is almost invariably found in AAA at the time of surgery or postmortem examination, and patients with atherosclerosis in other circulatory beds have an increased prevalence of AAA. However, unlike atherosclerosis, AAA is dominated primarily by degenerative changes in the elastic media, displays different epidemiological characteristics and has different genetic risk factors. Thus, AAA is thought to arise through pathophysiologic processes that are distinct from occlusive atherosclerosis, and that aortic atherosclerosis is neither sufficient, nor even necessary, for aneurysm, development. Indeed, some evidence has suggested that arterial wall remodeling associated with the regression of atherosclerotic plaques might be linked to aneurysm development. Current dogma would indicate that AAA arises from pathophysiological processes that are distinct from occlusive atherosclerosis, even though certain studies have pointed to their overlap. (Robert L, et al., "Elastin-elastase-atherosclerosis revisited," Atherosclerosis, 140(2):281–95 1998 Oct).

Male gender is also considered a risk factor for AAA, with some studies showing male:female ratios as high as 9:1. The possibility that there might be a relative biological resistance to the development of aneurysm in women suggests a sex-linked genetic component. For reasons that are not yet clear, there also appears to be a predilection for aortic aneurysms in Caucasians as compared to non-Caucasian populations.

There is also a strong association between persistent cigarette smoking and AAA, with a time lag of approximately 40 years. (MacSweeney et al., *Brit J. Surg.* 81:935–941, 1994). Some investigators have suggested that a component of smoke other than tar may contribute to the disease. (MacSweeny, et al., supra). For example, it has been proposed that increased levels of serum cotinine may contribute to the inactivation of α1-antitrypsin, which may subsequently enhance the degradation of the aortic wall by proteolytic enzymes, contributing to aneurysmal dilatation. Interestingly, the incidence of emphysema/COPD is high in patients with AAA, suggesting that the inactivation of α1-antitrypsin in these patients further disrupts the production of elastin need for maintenance of the aortic lumen. (Nicholls S C, et al., "Rupture in small abdominal aortic aneurysms," J Vasc Surg, 28(5):884–8 1998 Nov).

Hypertension is also considered a significant risk factor for AAA. It is associated with both increased prevalence and an increased risk of rupture. Though the risk of rupture of a <3 cm aneurysm with a diastolic pressure of less than 75 mm Hg is only 2%, the risk of rupture can increase to 100% for a 5 cm aneurysm and a diastolic pressure higher than 105 mmHg. (Schwartz, S. I., supra at 942).

4.2b(iv) AAA Pathogenesis

The pathogenesis of AAA involves the complex interaction of a variety of biological processes including marked alterations in elastin and collagen, chronic inflammation, autoimmune-associated processes, neovascularization, and a decrease in vascular smooth muscle cells (Thompson, R W, Current Opinion Cardiology 11:504–518, 1996). These processes act over many years and, ultimately, weaken the aortic wall. (Cenacchi G, et al., "The morphology of elastin in non-specific and inflammatory abdominal as aneurysms. A comparative transmission, scanning and immunoelectron-microscopy study," J Submiscrosc Cytol Pathol, 27(1): 75–81 1995 Jan). Although it is clear that weakening of the aorta involves disruption of the balance between collagen and elastin, controversy surrounds the mechanisms involved and their relative importance. (Anidjar S, et al., "Experimental study of determinants of aneurysmal expansion of the abdomen," Ann Vasc Surg, 9(2):127–36 1994 Mar).

Quantitative analyses show that elastin compromises 35% of the dry weight of an normal aorta media, but only 8% of the aortic media of patients with aneurysms (Campa, J S, Atherosclerosis 65:13–21, 1987). Elastin in the adventitia may also be affected in AAA. (White J V, et al., "Adventitial elastolysis is a primary event in aneurysm formation," J Vasc Surg, 17(2):371–80; discussion 380–1 1993 Feb). The biomechanical effect of the alteration in aortic wall elastin is to increase the stiffness of the affected areas of the aorta, with predictable hemodynamic effects. (He C M, et al., "The composition and mechanical properties of abdominal aortic aneurysm," J Vasc Surg, 20(1):6–13 1994 Jul).

In normal vascular tissues, elastin is produced by smooth muscle cells, and probably by fibroblasts. Elastin, like collagen, is secreted from the producer cells as tropoelastin molecules that combine to form elastin fibrils. Certain factors associated with wound healing can increase the cellular production of elastin, e.g., TGF-beta. (Sauvage M, et al., "Localization of elastin mRNA and TGF-beta in rat aorta and caudal artery as a function of age," Cell Tissue Res. 29:305–314, 1998). Certain other factors, in particular inflammatory cytokines such as TNF, can adversely affect the production of elastin. (Kahari V M et al., TGF-beta up-regulates elastin gene expression in human skin fibroblasts: evidence for post-transcriptional modulation," Lab Invest 66:580–8, 1992) Elastogenesis and elastolysis ideally remain in a steady state.

A model for atherosclerosis has been proposed that focuses on the relationship between elastin breakdown and elastin production in the arterial wall. (Robert L, et al., "Elastin-elastase atherosclerosis revisited," Atherosclerosis 140:281–295, 1998) According to this model, age-related modifications of the vessel wall include upregulation of elastolytic enzymes. The progressive deposition of lipids in elastic tissues, as well as the addition of lipoproteins or lipids to cell or organ cultures have been shown to modify matrix biosynthesis and upregulate elastase expression. Furthermore, the elastin laminin receptor present on vascular smooth muscle cells has been shown to trigger NO dependent vasodilatation and downregulation of cholesterol synthesis in young subjects, functions that decrease or disappear with age. (Varga Z, et al., "Age-dependent changes of K-elastin stimulated effector functions of human phagocytic cells: relevance for atherogenesis," Exp Gerontol 32:653–62, 1997) These findings have also been extended to the T-lymphocytes present in the atherosclerotic plaque. Significantly, after vascular injury such as balloon angioplasty, both intimal and medial smooth muscle cells proliferate. (Strauss B H, et al., "Extracellular matrix remodeling after balloon angioplasty injury in a rabbit model of restenosis," Circ Res 75:650–8, 1994) In those vascular injuries associated with the processes of atherosclerosis, there is likewise a proliferation of both types of cells. Elastin synthesis and smooth muscle cell proliferation are thought to be tightly regulated during repair of arterial wall injury. (Aoyagi M, et al., "Smooth muscle cell proliferation, elastin formation, and tropoelastin transcripts during the development of intimal thickening in rabbit carotid arteries after endothelial denudation," Histochem Cell Biol 107:117, 1997)

Decrease in elastin content in the aortic wall, by whatever mechanism this occurs, is a key element in aneurysm formation. Not to be bound by theory, we are nonetheless aware of various mechanisms that have been proposed. (Minion D J, et al., "Elastin is increased in abdominal aortic aneurysms," J Surg Res, 57(4):443–6 1994 Oct). In addition, elastin degradation products (EDPs) may contribute to the inflammatory processes that further degrade the aortic wall. For example, rats infused with EDPs, such as the peptide Val-Gly-Val-Ala-Pro-Gly (SEQ ID NO:1), develop a weakened aorta and are chemotactic for dendritic cells and macrophages (Senior, R. M. et al., *J. Cell Biol.*, 99:870–874, 1984).

Numerous observations suggest that enzymatic degradation of elastin plays a critical role in the evolution of aneurysm disease. One type of elastase found in aneurysm walls has been associated with human macrophages. (Curci JA, et al., "Expression and localization of macrophage elastase matrix metalloprotein abdominal aortic aneurysms," J Clin Invest, 102(11):1900–10 1998 Dec. 1). In fact, a number of proteolytic enzymes, including elastases, collagenases, and gelatinases are found in increased concentrations in the aortic media of patients with AAA. (Brophy, CM et al., J Surg Research 50:653–657, 1991; Vine and Powell, Clinical Sci., 81:233–239, 1991). In mycotic aneurysms, increases in elastase thought to originate from neutrophils have been identified in the arterial wall. (Buckmaster M J, et al., "Source of elastin-degrading enzymes in mycotic aortic aneurysms: bacterial or inflammatory response?," Cardiovasc Surg, 71:16–26 1999 Jan). MMP2, MMP3 and MMP9, enzymes that have the capability to degrade elastin, are expressed and produced in increased amounts in the aortas of humans with AAA. (Sakalihasan N, et al., "Activated forms of MMP2 and MMP9 in abdominal aortic aneurysms," J Vasc Surg, 24(1):127–33 1996 Jul.; Davis V, et al., "Matrix metalloproteinase-2 production and its binding to the matrix are in abdominal aortic aneurysms," Arterioscler Thromb Vasc Biol, 18(10):1625–33 1998 Oct). The association of MMP overexpression with aneurysm formation has also been observed in a rat model. (Allaire E, et al., "Local overexpression of TIMP-1 prevents aortic aneurysm degeneration an a rat model," J Clin Invest, 102(7):1413–20 1998 Oct. 1). Macrophages bearing MMP-9 have also been identified in temporal arteritis, raising the possibility that there is some similarity between the pathological processes at work in both conditions. (Nikkari S T, et al., "Macrophages contain 92-kd gelatinase (MMP-9) at the site of degenerated elastic lamina in temporal arteritis," Am J Pathol, 149(5):1427–33 1996 Nov).

Recent studies have suggested that increased elastase activity is more likely to be a primary event than a response to aneurysm formation (Cohen J R et al. Annals Vascular Surgery 4:570–574, 1990). Changes in elastin composition have been observed in dissecting thoracic aneurysms, possibly associating this mechanism with tendency for dissections to rupture. (Cattell M A, et al., "Increased elastin content and decreased elastin concentration may be predictive factors in dissecting aneurysms of human thoracic aorta," Cardiovasc Res, 27(2):176–81 1993 Feb). Plasmin, which is capable of destroying the extracellular matrix directly and indirectly via activation of latent MMPs, is also elevated in AAA tissues. Decreased activity of TIMPs has been suggested as a genetic basis underlying AAA, although DNA sequencing has provided no evidence to support this claim. (Tamarina N A, et al., "Expression of matrix metalloproteinases and their inhibitors in aneurysms of the aorta," Surgery, 122(2):264–71; discussion 271-2 1997 Aug; Elmore J R, et al., "Expression of matrix metalloproteinases and TIMPs in human abdominal aneurysms," Ann Vasc Surg, 12(3):221–8 1998 May).

Although factors that result in fragmentation of elastin may be important in the etiology of AAA, factors regulating the balance of collagen synthesis and degradation may also determine the rate of AAA progression. (Halloran, B. G. and Baxter, B. T., *Sem. Vasc. Surg.* 8:85–92, 1995). Early studies suggested that collagen comprises an increased proportion of the dry weight of the aortic media in patients with AAA, though other studies suggest the normal human abdominal aortic wall and that of patients with AAA contain similar amounts of collagen, as well as similar ratios between collagen types. (Menashi, S., *J. Vasc. Surg.*, 578–582, 1987). However, the solubility of collagen in the aneurysmal wall and its susceptibility to EDTA-induced dissociation are distinctly decreased in AAA. (Sobolewski, K. et al., *Act. Biocim. Polonica*, 42:301–308, 1995). Moreover, collagen turnover is increased in AAA, as determined, for example, by the concentration of the amino terminal propeptide of type III procollagen in patient blood or of collagen hydroxyproline in the urine of AAA patients. It is thought by some that whereas proteolytic degradation of elastin appears to be most specifically related to aneurysmal dilatation, collagen degradation is ultimately required for aneurysm rupture. (Dobrin, P. B. and Mrkvicka, R. *Cardiovascular Surgery*, 2:484–488, 1994).

In addition to collagen and elastin levels, the amount of glycosaminoglycans is slightly decreased, the percentage of chondroitin sulfate is increased, and that of heparan sulfate is significantly decreased in the abdominal aortas of AAA patients. Furthermore, a marked decrease in biglycan mRNA levels is unique to AAA, as compared to atherosclerosis and re-stenosis (Tamarinana et al., J. Surg. Research 74:76–80, 1998). Tumor necrosis factor alpha, interleukin-1 beta, interleukin-6 and interleukin-8 have also been shown to be elevated in AAA tissue as compared to controls (Hirose, H., et al., 1997). Further discussion of the role of inflammatory cytokines in AAA will be provided in the next section.

Neovascularization of the aortic wall is also a prominent component of AAA. A significant increase in the density of microvessels in the medial layer of AAA has recently been documented (Holmans, DR et al, Gay Vasc. Surg. 21:761–772, 1995). Studies have demonstrated that AAAs are associated with a marked angiogenic response, which is related to the degree of inflammation within the aortic wall. (Thompson MM, et al., "Angiogenesis in abdominal aortic aneurysms," Eur J Vasc Endovasc Surg, 11(4):464–9 1996 May).

AAA tissue has a significantly elevated concentration of nitrite ion, at concentrations that are known to be destructive of elastic fibers in vitro. Endothelial cells of the neovascular nets associated with AAA may produce nitric oxide that has matrix destructive effects. Although not yet established, it is logical to propose that the source of nitrite in AAA tissue could be endogenous (e.g. endothelial cells) or exogenous (e.g. tobacco smoke), or both. The deleterious effect of nitrites on elastin has been observed in a variety of clinical conditions, including premature skin aging and pulmonary emphysema, as well as AAA, all conditions with known associations with cigarette smoking. (Paik D C, et al., "The nitrite/elastin reaction: implications for in vivo degenerative effects," Connect Tissue Res, 36(3):241–51 1997). It is interesting that emphysema/COPD, which involves a deficiency of alpha 1-antitrypsin, appears associated with exacerbation or initiation of AAA. The MZ-alpha 1-antitrypsin phenotype has been found with increased frequencies in individuals with AAA in one study, although this has not been confirmed in a larger series (Cohen, JR et al., J Surg Research 49:319–321, 1990).

4.2b(v) Immune-Mediated Processes in AAA

The complex interaction of a variety of biological processes which act over many years to ultimately weaken the aortic wall, also include chronic inflammation, autoimmune-associated processes, neovascularization, and a decrease in the number of vascular smooth muscle cells, which may explain at least in part the alterations in the balance between matrix-degrading proteinases and their inhibitors, particularly among members of the matrix metalloproteinase (MMP) and plasminogen activator families.

A conspicuous example of the interaction of these various biological processes is found in those patients undergoing surgery for an "inflammatory abdominal aortic aneurysm" (IAAA), a AAA characterized by a massive inflammatory cell infiltrate that extends from the aortic wall into the surrounding tissues. (Grange, J. J. et al. *Cardiovasc. Surg.*, 5:256–265, 1997). This manifestation of AAA is found in 5–10% of AAA patients undergoing surgery. In this condition, the inflammatory processes extend outward from the aortic adventitia to involve surrounding structures, particularly in the retroperitoneum. It has been postulated that this condition arises from an allergic-type process in the adventitia that has the ultimate effect of stimulating localized inflammation and fibrosis. (Di Marzo, et al., "Inflammatory aneurysm of the abdominal aorta. A prospective clinical study," J Cardiovasc Surg (Torino), 40(3):407–12 1999 Jun). Increased collagen deposition in the periaortic tissues has been observed in IAAA, consistent with the established association in AAA and in other settings between chronic inflammation and stimulation of fibrosis. (Gargiulo M, et al., "Content and turnover of extracellular matrix protein in human "nonspecific" inflammatory abdominal aortic aneurysms," Eur J Vasc Surg, 7(5):546–53 1993 Sep).

Indeed, AAA is associated with a number of inflammatory diseases, including Takayasu's disease (10–30%) and syphilis (66%). (See Pearce, W. H. and Koch, A. E., Annals N.Y. Acad. Sci., 800:175–185, 1996). AAA may also be associated with an autoimmune process targeting certain components of the aortic wall. Additional studies provide evidence of apoptosis and cellular senescence. Certain inflammatory processes affecting blood vessels, termed arteritis, can result in aneurysm formation. Giant cell arteritis and Takayasu's disease are inflammatory processes affecting blood vessels, both with a propensity for insidious development of aneurysms of the thoracic and abdominal aorta which may be accompanied by dissection. (Joyce J W, "Uncommon arteriopathies," in RB Rutherford, ed., Vascular Surgery, W B Saunders, 1989, pp. 276–286). Both conditions are charracterized by a localized periarteritis with inflammatory mononuclear cell infiltrates and giant cells, accompanied by disruption and fragmentation of the elastic fibers of the arterial wall. The arterial inflammation in both disorders begins and is most pronounced in the media.

The presence of arterial wall disruption in the predominantly inflammatory disorder of arteritis and the presence of inflammation in those disorders predominately characterized by arterial wall disruption points to an interrelation between inflammation and structural attack on vessel walls. Further, however, an association has been observed in these conditions with abnormal patterns of vascular and perivascular fibrosis. Taken together, the spectrum of changes observed in arterial wall disruptive disorders appears to reflect an accelerated but ineffectual wound healing response to chronic injury and chronic inflammation which is largely localized to the aortic wall.

4.2b(vi) Fibrotic Processes in AAA and Arterial Wall Disruptive Disorders

Normal wound healing is understood to involve mechanisms of inflammation, connective tissue matrix degradation and deposition and scar tissue formation. Generally, wound healing proceeds through discrete sequential stages, including the initial response to injury (with hemorrhage, vasoconstriction and edema formation), inflammation (with the recruitment of leukocytes into the wound and the expression of growth factors), and fibroplasia (with the synthesis and cross-linking of collagen, the production of ground substance in the matrix and the proliferation of new blood vessels). Wound healing that is prolonged because of repeated trauma or because of an underlying pathological condition results in a chronic wound, where the inflammatory stage of wound repair persists, resulting in extensive tissue damage and ineffective fibroplasia.

Fibroblasts are the primary mesenchymal cells involved in wound healing. Undifferentiated mesenchymal cells in an injured area may be induced to differentiate into fibroblasts when stimulated by macrophage products. More recent data suggest that a subclass of interstitial fibroblasts can play an early role in immune-related processes by direct recruitment of inflammatory cells, release of soluble mediators, and/or promotion of fibroblast-to-immune cell communication. Additional fibroblasts are attracted to the injured area by chemotactic cytokines. PDGF, for example, has been demonstrated to be chemotactic for both fibroblasts and for smooth muscle cells. (Seppa H, et al., "Platelet derived growth factor is a chemoattractant for fibroblasts," J. Cell Biol 92:584–588, 1984; Grotendorst G R et al., "Platelet derived growth factor is a chemoattractant for vascular smooth muscle cells: J. Cell Physiol 112:261–266, 1982). The mesenchymal cell population in a wound is further augmented by the proliferation of both resident and newly arrived cells. Mesenchymal cell proliferation can be stimulated by PGDF, TNF, IL-1, lymphokines, insulin and IGF. Fibroblasts are responsible for the production of collagen in the wound. After the collagen molecule is synthesized within the fibroblast, it is secreted into the extracellular space in the form of procollagen. Procollagen can be identified by persistent nonhelical extensions of the alpha chains of he collagen molecule. Cleavage of this linear extension or registration peptide by enzymes in the extracellular space yields tropocollagen, which can aggregate into collagen fibrils. Intermolecular cross-links form between separate collagen molecules that are replaced by covalent bonds as the fibrils mature. While unaggregated tropocollagen molecules are soluble in saline, strong acid and high temperatures are needed to solubilize maturely cross-linked collagen. Extracellular connective tissue matrix contains components other than collagen, including proteoglycans, attachment proteins such as fibronectin, microfilaments and elastin. Elastin typically is not synthesized as part of an inflammatory, wound healing or injury response, although it may be synthesized in these conditions in some cases.

Response to vascular injury is understood to be a possible explanation for the development of atherosclerosis, a disorder commonly associated with certain arterial wall disruptive disorders, in particular AAA. The atherosclerosis process involves lipid induced biological changes in the arterial walls resulting in a disruption of homeostatic mechanisms that keeps the fluid phase of the blood compartment separate from the vessel wall. Other injuries to the endothelium have also been implicated in atherosclerosis. Injuries as diverse as physical injury, ischemia, toxins, biological injury, mechanical stress and immunological attack have been associated with atherosclerosis. At least four cell types are involved in the response of the vessel wall to injury: endothelial cells, monocytes, platelets and smooth muscle cells. Each can release growth factors, chemokines, fibrogenic peptides, chemoattractants and synthetic products, intended to reconstitute the injured vascular wall.

The histological progression of atherosclerosis begins with intimal thickening, which may reflect the vessel's adaptation to intraluminal hemodynamic alterations. Intimal thickening and more progressive atherosclerotic lesions are typically identified at vessel bifurcations, where turbulence and shear stress on the endothelium is greatest. The lesion of intimal thickening may progress to form a fatty streak, where fat is seen microscopically in the intimal layer, borne by fat-laden macrophages called foam cells. Fatty streaks may resolve, but more commonly progress to form fibrous plaques. Fibrous plaques are found in the immediate subendothelial region of the vessel wall, consisting of compact and stratified layers of organized smooth muscle cells coveed with a fibrous cap. The most advanced atherosclerotic lesions, and those associated with aneurysmal dilatation of the vessel wall, consist of dense fibrous tissue with prominent calcium deposition.

Since the normal response to tissue injury is inflammation, it is understandable that the atherosclerotic lesion shows a complex chronic inflammatory response, including infiltration of mononuclear leukocytes, cell proliferation and migration, reorganization of extracellular matrix, and neovascularization. In fact, the atheromatous plaque consists of a mixture of inflammatory and immune cells, fibrous tissue, and fatty material such as low density lipids (LDL) and modifications thereof, and alpha-lipoprotein. The causes and mechanisms of the atheromatous plaque build-up are not completely understood, though many theories exist. One theory on the pathogenesis of atherosclerosis involves the following stages: (1) endothelial cell dysfunction and/or injury, (2) monocyte recruitment and macrophage formation, (3) lipid deposition and modification, (4) vascular smooth muscle cell proliferation, and (5) synthesis of extracellular matrix.

In its initial phase, the inflammatory response to endothelial injury is characterized by the adherence of leukocytes to the vessel wall. Leukocyte adhesion to the surface of damaged endothelium is mediated by several complex glycoproteins on the endothelial and neutrophil surfaces. Two of these binding molecules have been well-characterized: the endothelial leukocyte adhesion molecule-1 (ELAM-1) and the intercellular adhesion molecule-1 (ICAM-1). During inflammatory states, the attachment of neutrophils to the involved cell surfaces is greatly increased, primarily due to the upregulation and enhanced expression of these binding molecules. Substances thought to be primary mediators of the inflammatory response to tissue injury, including interleukin-1 (IL-1), tumor necrosis factor alpha (TNF), lymphotoxin and bacterial endotoxins, all increase the production of these binding substances.

After binding to the damaged vessel wall, leukocytes migrate into it. Once in place within the vessel wall, the leukocytes, in particular activated macrophages, then release additional inflammatory mediators, including IL-1, TNF, prostaglandin $E_2$, ($PGE_2$), bFGF, and transforming growth factors β and β (TGFα, TGFβ). All of these inflammatory mediators recruit more inflammatory cells to the damaged area, and regulate the further proliferation and migration of smooth muscle. A well-known growth factor elaborated by the monocyte-macrophage is monocyte- and macrophage-derived growth factor (MDGF), a stimulant of smooth muscle cell and fibroblast proliferation. MDGF is understood to be similar to platelet-derived growth factor (PDGF); in fact, the two substances may be identical. By stimulating smooth muscle cell proliferation, inflammation can contribute to the development and the progression of myointimal hyperplasia.

Leukocytes, attracted to the vessel wall by the abovementioned chemical mediators of inflammation, produce substances that have direct effects on the vessel wall that may exacerbate the local injury and prolong the healing response. First, leukocytes activated by the processes of inflammation secrete lysosomal enzymes that can digest collagen and other structural proteins. Releasing these enzymes within the vessel wall can affect the integrity of its extracellular matrix, permitting SMCs and other migratory cells to pass through the wall more readily. Hence, the release of these lysosomal proteases can enhance the processes leading to myointimal hyperplasia. Second, activated leukocytes produce free radicals by the action of the NADPH system on their cell membranes. These free radicals can damage cellular elements directly, leading to an extension of a local injury or a prolongation of the cycle of injury-inflammation-healing.

According to this theory, the initiation of atherosclerosis is potentially due to a form of injury, possibly from mechanical stress or from chemical stress. How the body responds to this injury then defines whether, and how rapidly, the injury deteriorates into an atherosclerotic lesion. It is known that following endothelial injury, a series of repair mechanisms are initiated. Within minutes of the injury, a layer of platelets and fibrin is deposited over the damaged endothelium. Within hours to days, inflammatory cells begin to infiltrate the injured area. Within 24 hours after an injury, vascular smooth muscle cells (SMCs) located in the vessel media commence DNA synthesis. A few days later, these activated, synthetic SMCs migrate through the internal elastic lamina towards the luminal surface. A neointima is formed by these cells by their continued replication and their production of extracellular matrix. An increase in the intimal thickness occurs with ongoing cellular proliferation matrix deposition. When these processes of vascular healing progress excessively, pathological conditions result. An overgrowth of smooth muscle cells and neointima, for example, is associated with the development of restenosis after angioplasty.

While the above-described cycle of injury repair in the wall of blood vessels has been described in detail with respect to endothelial injury and the development of atherosclerosis, it is understood that other injuries to the vessel wall are likely to trigger comparable processes of injury repair. For example, the source of vessel wall injury may arise from immunologically activated cells within the vessel wall, or from inflammatory cytokines, or from abnormal proteins or from genetic mutations or abnormalities. Other tissues manifest analogous interactions between tissue injury and repair, with the association of inflammation and fibrotic processes. Conditions in the lung, for example idiopathic pulmonary fibrosis, may manifest the interrelation of these processes, with tissue fibrosis as the pathological outcome. Systemic sclerosis, as another example, is a multisystemic disorder characterized by diffuse tissue fibrosis, wherein immunological mechanisms, vascular damage and fibroblast activation are key events. Renal interstitial fibrosis likewise manifests the combination of immune and non-immune mediated components of injury repair. Other examples of the interaction of inflammation and fibrosis in wound healing will be readily evident to practitioners of ordinary skill in the medical arts. Potential therapeutic targets for treatment of fibrotic conditions include those agents that affect various factors in the injury repair process, for example, those agents that affect b1 integrins, where a1b1 is understood to mediate signals that induce down-regulation of collagen gene expression and a2b1 is understood to mediate MMP-1 expression, those agents that affect fibroblast proliferation, those agents that affect macrophage activation and recruitment, those agents that affect smooth muscle cell differentiation and proliferation, those agents that affect TGF-beta and other cytokinases and chemokinases, and those agents that affect gene expression, transgenes, etc. Representative therapeutic targets include CTGF, interferons, relaxin, TGFb3, HGF, prolyl hydroxylase, C-proteinase, lysyl oxidase, and antisense oligonucleotides, although other therapeutic targets will be identified by practitioners in the relevant arts using no more than routine experimentation.

Table 1 presents a list of those molecules whose expression in "choroidal fibrosis" has been evaluated. These molecules represent additional targets for therapeutic manipulations to influence the course of injury repair and fibrosis. Recognizing the association between fibrotic processes and arterial wall disruptive disorders may permit the development of therapeutic agents directed to those processes that will have a beneficial effect on the development or progression of arterial wall disruptive disorders such as AAA.

TABLE 1

| Molecule | Expression in Choroidal Fibrosis vs Controls |
| --- | --- |
| BIG H3 | Decreased |
| b1-integrin | Increased |
| Collagen 3 a1 | Unchanged |
| Collagen 1 a1 | Unchanged |
| Collagen 1 a2 | Unchanged |
| Collagen 6 a1 | Unchanged |
| Collagen 6 a2 | Increased |
| Collagen 6 a3 | Increased |
| Elastin | Increased |
| Fibulin-1 | Unchanged |
| Fibulin-2 | Unchanged |
| Fibulin-3 | Unchanged |
| Fibulin-4 | Unchanged |
| Fibulin-5 | Unchanged |
| FBN-2 | Unchanged |
| HLA-DR b | Unchanged |
| HME | Increased |
| IgK | Unchanged |
| Laminin Receptor | Unchanged |
| Lam C2 | Unchanged |

Based on the observed associations between inflammation, injury, healing, and related biological phenomena, therefore, one major thrust of AAA research is directed to the inflammatory process and its regulation of arterial wall matrix remodeling. (Grange, J. J., et al. Cardio. Vasc. Surg. 5:256–265, 1997). It is proposed that the presence of inflammatory cells within the media of aneurysmal aortas may play a critical role in the destruction of elastin and collagen through production of matrix-degrading proteinases. (Newman K M, et al., "Matrix metalloproteinases in abdominal aortic aneurysm: characterization, purification, and their possible sources," Connect Tissue Res, 30(4):265–76 1994). The presence of inflammatory cells within the media of aneurysmal aortas may play a critical role in the destruction of elastin and collagen through production of matrix-degrading proteinases. The predominant immune cells associated with inflammatory AAA are activated T-cells, and macrophages, dendritic cells and B cells have also been identified. (Lebermann, J. et al., J. Vasc. Surg. 15:569–572, 1992). Immune cells have also been associated with expanding AAAs. (Freestone T, et al., "Inflammation and matrix metalloproteinases in the enlarging abdominal a aneurysm," Arterioscler Thromb Vasc Biol, 15(8):1145–51 1995 Aug). Vascular dendritic cells (CD1a and S100 positive) have been shown to be present in both the media and the adventitia of the aneurymic aorta, in contact with both CD3, CD4, and CD8 positive T cells or CD20 positive B cells. (Bobryshev, Y. V. et al., Cardiovascular Surgery, 6(3):240–249, 1998). Since the T-cell inflammatory reaction resolves after aneurysm replacement, there may be a substance in the aneurysm wall that elicits the inflammatory response. Whether the immune response antedates the aneurysm, or results therefrom, awaits further studies.

Other investigators (Coch, A E et al., Am. J. Path., 137:1199–1213, 1990) have provided data to suggest that not only "inflammatory AAA", but also non-inflammatory AAA, is an immune-mediated event. A number of observations support the contention that AAA may be caused by autoimmune response to components of the aortic wall. It has been proposed that ceroid, an "age-pigment" ("aortic content") that leaks into the surrounding tissues in AAA may be the immunogen responsible for this condition (Coch, A E, et al., AM. J. Path., 137:1199–1213, 1990; Beckman, E N, AM. J. Clin. Pathol., 85:21–24, 1986; Ball, R Y, et al., Arc. Pathol. Lab. Med., 111:1134–1140, 1987; Brophy, C M et al., Annals Vasc. Surg., 5:229–233, 1991; Ball, R Y, et al., Arc. Pathol. Lab. Med., 111:1134–1140, 1987). Ceroid, generally considered to be related to the lipofuscin group of pigments, is believed to be derived from previous oxidation of unsaturated lipid or lipid-protein complexes. It is an autofluorescent material that is insoluble in organic solvents and binds lipids-soluble dyes such as oil-red O. In the event of AAA-associated necrosis, ceroid may be spilled from dead cells and subsequently phagocytosed by macrophages. A similar situation occurs in atherosclerosis, where ceroid is abundant in the atheromatous debris of atherosclerotic plaques in drusen and other structures. (Yardley et al., Arch. Pathol. Lab. Med. 111:1134–1140, 1987) Furthermore, histologic examination of AAA specimens reveals the presence of Russell bodies, which are hallmarks of autoimmune disease.

In the spectrum of autoimmune disorders, certain HLA alleles play a key role in the presentation of cell-proteins as autoantigens in different specific conditions. A recent study provides data that Class II histocompatibility antigens are expressed by vascular smooth muscle cells in human AAA and that these altered smooth muscle cells may be a target for lymphocytes infiltrating the aorta (Kosierkiewicz, T A et al., Surg. Forum 46:365–367, 1995). More recent studies indicate that HLA-DR2(15) has an important role as a genetic risk factor for AAA in the Japanese population (Hirose, H., et al., J. Vasc. Surg. 27:500–503, 1998) and that a genetic risk of determinate can be mapped to the HLA-DRB1 locus of patients with inflammatory AAA (Rasmussen, T. E. et al, J. Vasc. Surg. 25:356–364, 1997).

In some immune-mediated disorders, such as rheumatoid arthritis and glomerulonephritis, immunoglobulin deposition and complement activation are associated with tissue destruction. The complement system is understood to be an important mediator of inflammation and immunity with roles in chemotaxis, macrophage activation, and cell death. The complement cascade is activated in the classical pathway by immunoglobulin M and G, or alternatively, by activating surfaces with tissues. Significant to AAA, Capella et al. (J. Surg. Research 65:31–33, 1996) have demonstrated the presence of elevated levels of C3 and IgG in the aortic wall of AAA donors, lending further support to the notion of an immune-mediated pathophysiology for AAA. The presence of large amounts of IgG in the degenerating media of AAAs has further lead to speculation that a specific immune response might contribute to the etiology of AAA. B-cells have also been identified. (Pasquinelli G, et al., "An immunohistochemical study of inflammatory abdominal aortic aneury," J Submicrosc Cytol Pathol, 25(1):103–12 1993 Jan). It is pointed out, however, that in one recent study investigating the repertoire of immunoglobulin heavy chain genes in AAA suggests that, in the vast majority of atherosclerotic AAA, the B-cell rich adventitial infiltrates are not an autoimmune response to a limited repertoire of tissue antigens (Walton, L. J. et al., Atherosclerosis 135:65–71, 1997).

A number of investigators have recently demonstrated that IgG isolated from AAAs react against major protein bands migrating at 40 kDa and 80 kDa on Western blots of separated AAA aorta extracts (Tilson, M D, Biochem. Biophys. Research Communication, 213:40–43, 1995; Xia, S et al., Biochem. Biophys. Research Communication, 219:36–39, 1996; Gregory A K et al., Arc Surg, 131:85–88, 19960. Further studies of the 40 kDa auto-antigen indicate that it has a high degree of amino acid sequence homology to microfibril-associate glycoprotein (MAGP). Because microfibrils serve as architectural scaffolds for tropoelastin deposition during elastogenesis, one might speculate that enzymatic degradation of elastin in AAA exposes previously masked epitopes associated with microfibrillar proteins. This, in turn, might lead to recognition of these epitopes and the initiation of an autoimmune response. Tilson and colleagues (J. Vasc. Surg. 26:313–318, 1997) have purified a protein, designated AAAP-40, from the human aorta that is homologous to bovine aortic MAGP-36; this protein in immunoreactive with IgG purified from the serum and aortic wall of patients with AAA. AAAP-40 (as well as MAGP-36) has fibrinogen-like and vitronectin-like motifs and shares similarities with immunoglobulins of the kappa family. Tilson and co-workers have also suggested that some bacterial and viral pathogens (e.g. CMV, herpes virus) may be molecular mimics of AAAP-40, capable of initiating an autoimmune response against self-proteins (Ozsvath, K., et al., Annals NY Acad. Sci., 800:288–293, 1996).

A variety of inflammatory cytokines, chemoattractants, peptide growth factors and immune cells have been found in aneurysm tissues, suggesting a possible model for inflammatory mediators or immune cells in the pathogenesis of the disease. Tumor necrosis factor alpha (TNFα), interleukin-1β (IL-1β), interleukin-6 (IL-6) and interleukin-8 (IL-8) are elevated in AAA tissue as compared to controls. (Hirose, H. et al., J. Vasc. Surg. 26: 313–318, 1997). I1–1B has been associated with AAA. (Keen RR, et al., "Interleukin-1 beta induces differential gene expression in aortic smooth muscle," J Vasc Surg, 20(5):774–84; discussion 784–6 1994 Nov). Perhaps a consequence of increased IL-1 or TNF-α levels, significant elevation of ICAM-1 expression has also been demonstrated in AAA, which may enhance the recruitment of inflammatory cells to the aortic wall. (Davis, C. et al., *J. Vasc. Surg.*, 16:474–475A, 1992; Pearce, W. H., supra at 179). In addition, soluble ICAM has been detected in supernatants of AAA diseased tissue, probably due to cleavage of membrane bound ICAM-1. Oxidized LDL or elastin fragments may also initiate the inflammatory response.

Specific factors attracting macrophages and lymphocytes into the aorta have not been reported, but chemotactic elastolytic peptides and other matrix bound mediators of inflammation may serve as a potential stimulus for monocyte infiltration. (Senior, R. M. et al., *J. Cell Biol.*, 99:870–874,1984). In addition, elevated levels of urokinase-type (uPA) and tissue-type (tPA) plasminogen activators have been documented in AAA tissues and localized to macrophages within the inflammatory infiltrate characteristic of AAA. (Reilly, J. M., *Annals NY Acad. Sci.*, 800: 151–156, 1996). Associations between inflammatory cytokines and atherosclerosis are well-established. Cytokine-mediated or immunological mechanisms may overlap between atherosclerosis and atherosclerotic occlusive disease and arterial wall disruptive disorders.

4.2b(vii) Pharmacological Interventions in AAA

It is well established in the art that the treatment for AAA is surgical. There are no pharmacological interventions that are presently employed clinically. Recognition of the underlying pathophysiological processes has permitted conjectures to be made about therapies that may be valuable in treating AAAs, to stabilize them and prevent their expansion, to prevent their rupture, or, optimally, to effect their regression. Identification of aneurysm-associated genes may permit the manipulation of DNA, mRNA or proteins related to the development or the progression of AAA. (Grange J J, et al., "Pathogenesis of abdominal aortic aneurysm: an update and look toward the future," Cardiovasc Surg, 5(3): 256–65 1997 Jun). Alternatively, clinical trials of anti-inflammatory agents or protease inhibitors may be warranted. Furthermore, identification of agents that induce or exacerbate aneurysms or other arterial wall disruptive disorders may be important to clinicians so that they can make decisions about avoiding the use of those agents in patients at risk for the development or progression of such disorders, even when the agent in question may have an unrelated beneficial therapeutic effect. Further, as agents are identified with effect in treating arterial wall disruptive disorders, these agents may be applicable also for the treatment of AMD.

The notion that aneursymal disease shares features in common with other autoimmune diseases opens the way for new approaches to the treatment and prevention of AAA. These treatment modalities in turn may have a beneficial effect on associated diseases such as AMD. If tolerance for an aortic autoantigen could be induced, for example, it might be possible to modulate the progression of aortic degeneration in a fashion similar to that which has been employed in patients with rheumatoid arthritis (Trentham, D. E., et al., Science 261:1727–1730, 1993). Monoclonal antibodies directed to the leukocyte CD-18 molecule have been shown experimentally to reduce inflammation associated with AAA and to slow its expansion. (Ricci M A, et al., "Anti-CD 18 monoclonal antibody slows experimental aortic aneurysm expansion," J Vasc Surg, 23(2):301–7 1996 Feb). Further evaluation of the role of immune-related cell surface molecules and adhesion molecules in the expansion of AAA will allow identification of pharmacological interventions to modulate these receptor sites.

The finding that elastolytic MMPs, particularly MMP9 and MMP2, are expressed and produced in increased amounts in human AAA, has led to the possibility that these enzymes might serve as rationale targets for pharmocotherapy in this disease (Thompson, R. W. and W. C. Parks Annals N.Y. Acad. Sci., 800:157–174, 1996). Indeed, inhibition of MMP activities has been shown to suppress aortic elastin degradation in vivo in an animal model of AAA. (Thompson RW, et al., "MMP inhibition in abdominal aortic aneurysms. Rationale for a prospective randomized clinical trial," Ann NY Acad Sci, 878(—HD-):159–78 1999 June 30). A number of MMP inhibitors with effect on experimentally induced AAAs have been identified. A hydroxamate based MMP antagonist RS 312908 has been found to inhibit elastase, promote the preservation of elastin in the aortic wall and enhance the pro-fibrotic response therein. (Moore G, et al., "Suppression of experimental abdominal aortic aneurysms by systemic treatment with hydroxamate-based matrix metalloproteinase inhibitor (RS 132908)," J Vasc Surg, 20(3):522–32 1999 Mar). The MMP inhibitor BB-94 (also known as batimastat) limits the expansion of experimental AAAs by the direct inhibition of MMP and by a further control of the local inflammatory response. (Bigatel D A, et al., "The matrix metalloproteinase inhibitor BB-94 limits expansion of experimental abdominal aortic aneurysms," J Vasc Surg, 29(1):130–8; discussion 138–9 1999 Jan).

Calcium channel blockers have been shown to increase proteolytic activity of metalloproteinases secreted by vascular smooth muscle cells. For example, amlodipine has been identified as an agent that enhances elastin degradation and potentiates MMP-9 activity in tissue cultures. (Boyle J R, et al., "Amlodipine potentiates metalloproteinase activity and accelerates elastin degradation in a model of aneurysmal disease," Eur J Vasc Endovasc Surg, 16(5):408–14 1998 Nov). Further elaboration of this mechanism may permit interventions to counteract MMP activity and thus protect the arterial wall tissue from further degeneration. This finding may also lead clinicians to avoid the use of calcium channel blockers for other cardiovascular conditions in patients at increased risk for aneurysm formation. Identification of other substances that initiate or exacerbate the development of arterial wall disruptive disorders, including aneurysm and dissection, can be anticipated. Once such substances are identified, the clinician is likely to avoid their use in the patient suffering from or at risk for arterial wall disruptive disorders. It may be determined that these agents similarly have a deleterious effect on the development or the progression of AMD.

Further understanding of the basic science of AAAs is likely to lead to the development of further therapeutic strategies that involve the manipulation of proteinases associated with mononuclear inflammatory cells as well as the manipulation of related inflammatory processes. (Thompson R W, "Basic science of abdominal aortic aneurysms: emerging therapeutic strategies for an unresolved clinical problem," Curr Opin Cardiol, 11(5):504–18 1996 Sep). Further understanding of the vascular biology of AAAs may also give rise to unexpected findings with therapeutic implications. For example, certain antibiotics exhibiting MMP-inhibiting properties, e.g., doxycycline, have been studies as inhibiting agents for expansion of experimental aneurysms. (Boyle J R, et al., "Doxycycline inhibits elastin degradation and reduces metalloproteinase activity in a model of aneurysmal disease," J Vasc Surg, 27(2):354–61 1998 Feb). In one study, non-antibiotic tetracyclines and the common antibiotic doxycycline have been identified as having a dose-dependent aneurysm suppressing effect that resulted in limiting the disruption of elastin without altering either the inflammatory response or the aortic wall production of MMPs (Curci J A, et al., "Pharmacologic suppression of experimental abdominal aortic aneurysms: trial of doxycycline and four chemically modified tetracyclines," J Vasc Surg, 28(6):1082–93 1998 Dec).

General inhibition of inflammation appears to have some effect on limiting the expansion of AAAs. There may be related beneficial effects on AMD. For example, the adverse effects of PGE2 on aortic smooth muscle viability and cytokine secretion are understood in the art. Drugs inhibiting prostaglandin synthesis may be useful in treating or preventing aneurysms. (Walton L J, et al., "Inhibition of prostaglandin E2 synthesis in abdominal aortic aneurysms: implications for smooth muscle cell viability, inflammatory processes, and the expansion of abdominal aortic aneurysms," Circulation, 100(1):48–54 1999 Jul. 6). In the rat model, indomethacin has been shown to inhibit aneurysmal growth, possibly by decreasing macrophage expression of MMP-9. (Holmes D R, et al., "Indomethacin prevents elastase-induced abdominal aortic aneurysms in the rat," J Surg Res, 63(1):305–9 1996 Jun). The role of indomethacin in attenuating aneurysm growth is thought to be mediated by the cox2 isoform of cyclooxygenase, which decreases PGE2 and MMP-9. (Miralles M, et al., "Indomethacin inhibits expansion of experimental aortic aneurysms via inhibiting the cox2 isoform of cyclooxygenase," J Vasc Surg, 29(5): 884–92; discussion 892–3 1999 May).

Propranalol, a beta-blocker, has also been documented to suppress aneurysm development in a mouse model of AAA, the mechanism of action thought to be due to enhancement of connective tissue cross-linking (Brophy, C M et al., J. Surg. Research 46:330–332, 1989). Propranalol and related beta-blockers are also known to be effective in reducing systemic hypertension, which is understood to promote the expansion of aneurysms. Beta-blockers and other anti-hypertensive agents form a mainstay of treatment for aortic dissections, a manifestation of arterial wall disruptive disorder not typically associated with AAA. (Dzau V J et al., "Diseases of the aorta," pp. 1394–1398 in A S Fauci et al., eds., Harrison's Principles of Internal Medicine, 14th Ed., McGraw-Hill 1998).

4.4 Arterial Wall Disruptive Disorders and AMD

A number of striking similarities exist between the structure, composition, and pathology of the ocular RPE-Bruch's membrane-choroid complex and that of the arterial wall. Additional similarities are observed between the various known risk factors for diseases, namely macular degeneration and arterial wall disruptive disorders, caused by pathological changes in these tissues. These shared risk factors include heritability, exasercbation by hypertension, smoking, age, and potential associations with chronic obstructive pulmonary disease, a1-antitrypsin deficiency, and atherosclerosis.

The RPE-Bruch's membrane-choroid complex is comprised of a confluent epithelial cell monolayer, a laminar collagen-elastin-collagen matrix referred to as Bruch's membrane, and a choroidal stroma comprised of loosely arranged fibroblasts, smooth muscle cells, pericytes, capillaries, bundles of collagen fibers (near the scleral junction), and other extracellular matrix constituents. The overlying sclera is comprised largely of densely packed collagen and some elastin. Bruch's membrane is a trilaminar extracellular matrix complex that lies between the retinal RPE and the primary capillary bed of the choroid, the choriocapillaris. Bruch's membrane is comprised of two collagen layers, referred to as the inner and outer collagenous layers, that flank a central domain comprised largely of elastin. The strategic location of Bruch's membrane between the retina and its primary source of nutrition, the choroidal vasculature, is essential for normal retinal function (Marshall et al, 1998; Guymer and Bird, 1998). Immunohistochemical studies have documented the presence of collagen types I, III, IV, V, and VI within Bruch's membrane proper [Das, 1990 #670; Marshall, 1992 #671]. Type VI is associated specifically with the elastic lamina, types IV and V with the basal laminae of the choriocapillaris and RPE, and types I and III with the inner and outer collagenous layers. The presence of collagen types I, III, IV and V in these tissues has been confirmed biochemically. Histochemical studies have suggested the presence of glycosphingolipids in Bruch's membrane [Farkas, 1971 #38].

In addition to these structural and compositional similarities, pathogenic mechanisms similar to those described for arterial wall disruptive disorders (AAA, TAA, TAAA, acute dissecting aneurysms, aortic stenosis, atherosclerosis) are observed within the RPE-Bruch's membrane-choroid complex. Distinct pathologic features associated with arterial disease include the deposition and rupture of protein-lipid plaques; degradation of elastin and collagen; up-and/or down-regulation of various extracellular matrix proteins and associated constituents; infiltration of inflammatory cells, including dendritic cells; generation of autoantibodies directed against extracellular components of the vessel wall; "chronic inflammation"; neovascularization; and proliferation of fibroblasts and smooth muscle cells/pericytes. In many respects, many of the age-related changes in Bruch's membrane parallel those observed in the vascular wall during atherosclerosis [Bilato, 1996 #680].

Pathological changes known to occur within Bruch's membrane in aging and age-related diseases, including AMD, that are similar to those in arterial wall disruptive disorders include: the deposition of abnormal extracellular deposits referred to as drusen, basal laminar deposits, and basal linear deposits (Hageman, 1997; Marshall et al., 1998; Guymer and Bird, 1998), progressive thickening (Feeney-Burns and Ellersieck, 1985; Bird, 1992; Newsome et al, 1987a,b; Ramrattan et al, 1994), accumulation of lipids and other extracellular material (Pauleikhoff et al, 1990, 1992; Sheraidah et al, 1993; Holz et al, 1994a,b), changes in the degree of calcification and fragmentation (Spraul and Grossniklaus, 1997), modification and degeneration of collagen and elastin (Feher and Valu, 1967), increase in the advanced glycation end (AGE) products pentosidine and carboxymethyllysine (Ishibashi et al, 1998; Hanada et al, 1999), and an overall increase in the amount of noncollagenous proteins in the macula, but not the periphery (Hewitt et al, 1989; Karatowski et al, 1995); and a significant decline in the solubility of Bruch's membrane collagen with age, from 100% in the first decade to 40–50% in the ninth decade (Wojciech). Functionally, these processes may cause the exponential reduction in the hydraulic conductivity of Bruch's membrane that has been documented to occur with age (Moore et al, 1995; Starita et al, 1996; Hodgetts et al, 1998a,b) which, intuitively, must impair normal function of the RPE-Bruch's membrane interface. The fact that debris accumulates first in the inner collagenous layer (Feeney-Burns and Ellersieck, 1985; Newsome et al, 1987) may suggest that the elastic lamina is an important site of resistance to permeability with age. This age-related interruption of bulk flow through Bruch's membrane may result in pigment epithelial detachments (Bird, 1992), having a profound effect on the physiology of the RPE.

Thus, it appears that many of the basic structural and functional properties of Bruch's membrane likely depend on the integrity and nature of its collagen and elastin fibers. Choroidal neovascularization is a common manifestation of the exudative form of AMD, typically resulting in severe vision loss. It is likely that degradation of collagen and elastin in Bruch's membrane represents a crucial step in this process. Indeed, MMP-2 and MMP-9, two metalloproteinases with elastolytic properties, increase in Bruch's membrane with age (Guo et al, 1997). These metalloproteinases, which are typically secreted at sites of inflammation, cause the destruction of elastin in diseases such as emphysema, atherosclerosis, and arthritis, and may be responsible for similar pathology in Bruch's membrane. Moreover, TIMP-3 has been shown to be synthesized by RPE and choroidal endothelial cells and is found in relatively high concentrations in Bruch's membrane and drusen (Vranka et al, 1997). Thus, this inhibitor of metalloproteinases may play a major role in maintaining ECM homeostasis in Bruch's membrane. It is known that elastin fragmentation products are capable of inducing macrophage migration (Kamisato et al, 1997) and are potent stimulators of angiogenesis/neovascularization. Thus, it is logical to propose that any AMD-associated process that leads to the destruction of the elastic lamina may also induce choroidal neovascularization.

Far less is known pertaining to the changes that occur in the choroidal stroma proper in macular disease. It is known that there is a significant loss of capillary endothelial cells, especially in the macula. In addition, there has been some suggestion that the choroid thins with age and AMD, although this has not been rigorously documented.

Studies conducted in our laboratory provide additional new insight into the similarities between macular degeneration and arterial wall disruptive disorders. These include:

1) A strong statistical correlation between AAA and neovascular AMD (P<0.00001) has been documented in a large repository of human donor eyes.

2) In a small clinical trial, five out of eight patients with AAA were diagnosed with a characteristic AAA fundus phenotype and AMD when examined ophthalmoscopically.

3) A review of patients seen at the University of Iowa over the past five years for both AAA and AMD reveals a similar AAA fundus phenotype.

4) Rigorous histochemical and biochemical analyses of drusen have revealed that drusen and arterial disease plaques are similar in composition.

5) Significantly, a novel association between drusen and dendritic cells has been identified.

6) Ultrastructural and immunohistochemical examination of choroids from 151 human donors between 6 hours and 101 years of age, with and without AMD and various arterial wall disruptive disorders (AAA, TAA, TAAA, acute dissecting aneurysms, aortic stenosis, atherosclerosis), has revealed a novel pathology associated with these conditions. The choroidal stromas of 30 of these individuals are filled with newly synthesized collagen, elastin, elastin-associated microfilaments, and other distinct structural proteins and fibrils. Based on preliminary immunohistochemical analyses, the collagen associated with this condition appears to be largely type III and VI and typically exhibits a "spiraled", or "frayed" morphology that is often associated with specific hereditary and acquired diseases. This previously undescribed phenomenon, referred to as "choroidal fibrosis", shares many pathological features that are common in arterial wall disruptive disorders.

7) RT-PCR analyses of RPE-choroid complexes derived from a series of control (non-diseased) and affected (AMD/AAA, AMD, AMD/aortic stenosis) donors have revealed distinct patterns of up- and down-regulated gene expression between the two groups. These include "upregulation" of b1 integrin, elastin, collagen VIa2, collagen a3, PI-1 (antitrypsin), PI-2, human metalloelastase (and perhaps fibrillin-2) and "downregulation" of BigH3. No detectable differences in expression levels of collagen IIIa1, collagen Ia2, collagen 6a1, fibulins-1, 2, 3, 4, and 5, HLA-DR, Ig kappa, laminin receptor, or laminin C2 were observed. Because of the limitations of RT-PCR, additional real time quantitative RT-PCR studies are being conducted to assess the precise levels of these genes in the two groups.

8) Autoantibodies directed against two specific RPE-, retina- (approximately 35 kDa and 50 kDa), and drusen-associated (approximately 42 kDa) proteins have been identified in the sera of patients with both AMD and AAA, suggesting additional similarities between the mechanisms of AMD and arterial diseases.

9) Gene array analyses of RPE/choroid tissues derived from human donors with AMD and/or AAA have provided compelling evidence for shared mechanisms of pathogenesis (gene expression profiles) between these disorders.

10) Immunohistochemical analyses have documented that the elastic lamina in the macula of AMD donors is thinner and more fragmented than that in the extramacular regions. These data indicate that degradation of elastin in the macula is more robust than in the periphery. Conversely, since most elastin synthesis occurs during gestation in humans, any postnatal synthesis of elastin that occurs in the macula might be expected to differ significantly in amount and/or content as compared to elastin that is synthesized earlier.

4.4 Diagnostic Assays

In one aspect, the invention provides a method for diagnosing, or determining a predisposition to developing AMD by detecting one or more markers which have been associated with an increased risk for AAA. In a preferred embodiment, the marker for macular degeneration in the eye is drusen formation or the occurrence of a drusen-associated marker such as a drusen-associated molecule (DRAM) or a drusen-associated molecular pathology. Examples of drusen-associated molecular pathologies include: the presence of disciform scars and/or choroidal neovascularization and/or fibrosis (e.g. spiral collagens, elastin fibrils and microfilaments) in the macula, a change in the pigmentation of the macula, the occurrence of cell death in the RPE, the occurrence of certain immune-mediated events in the eye, and the occurrence of dendritic cell proliferation, migration and differentiation in the sub RPE space.

The drusen-associated markers may be detected by one or more ophthalmological procedures, such as fundus fluorescein angiography (FFA), fundus ophthalmoscopy or photography (FP), electroretinogram (ERG), electrooculogram (EOG), visual fields, scanning laser ophthalmoscopy (SLO), visual acuity measurements, dark adaptation measurements or other standard method.

In one method of the invention, the occurrence of a drusen-associated disorder may be detected by conventional ophthalmological methods in which a patient's eye is examined for the presence of drusen. Drusen are subretinal pigment epithelial deposits that are characteristic of but not uniquely associated with age-related macular degeneration (AMD). Age-related macular degeneration is associated with two types of drusen that have different clinical appearances and different prognoses. Hard drusen appear as small, punctate, yellow nodules and can precede the development of atrophic AMD. Areolar atrophy of the retinal pigment epithelium (RPE), choriocapillaris, and outer retina develop as the drusen disappear, but drusen can regress without evidence of atrophy. Soft drusen appear as large (usually larger than 63 microm in diameter), pale yellow or grayish-white, dome-shaped elevations that can resemble localized serous RPE detachments. They tend to precede the development of clinically evident RPE detachments and choroidal neovascularization. Drusen characteristics correlated with progression to exudative maculopathy include drusen number (five or more), drusen size (larger than 63 microm in diameter), and confluence of drusen. Focal hyperpigmentation in the macula and systemic hypertension also are associated with an increased risk of developing choroidal new vessels (CNVs). Large drusen are usually a sign of diffuse thickening of Bruch's membrane with basal linear deposit, a vesicular material that probably arises from the RPE, constitutes a diffusion barrier to water-soluble constituents in the plasma, results in lipidization of Bruch's membrane, and creates a potential cleavage plane between the RPE basement membrane and the inner collagenous layer of Bruch's membrane through which CNVs can grow.

Other drusen-associated molecular pathologies include the occurrence of distinct fundus appearances in the eye such as white to yellow fundus spots (which are distinct from drusen) which accompany a disciform macular degeneration, or yellow deposits which are associated with atrophic macular degeneration. These AMD-associated fundus findings also include geographic atrophy (GA, which is characteristic of the dry form of AMD), and disciform scars and choroidal neovascularization (DS/CNV, which is characteristic of the wet form of AMD). In other instances, the AMD-associated fundus findings do not distinguish between the wet or dry form.

In a preferred embodiment, the marker is molecular marker associated with drusen deposits—i.e. a drusen-associated molecules (DRAM). Drusen may be detected by determining the presence of one or more DRAMs, such as amyloid A protein, amyloid P component, antichymotrypsin, apolipoprotein E, b2 microglobulin, complement 3, complement C5, complement C5b-9 terminal complexes, factor X, fibrinogen, immunoglobulins (kappa and lambda), prothrombin, thrombospondin and vitronectin. In another embodiment, the drusen-associated marker is a molecule whose production is altered in a drusen-associated molecular pathological process. For example, one pathological process associated with drusen is cell death and/or dysfunction in the retinal pigment epithelium (RPE). A number of molecular markers have been associated with such dysfunctional RPE cells including: HLA-DR, CD68, vitronectin, apolipoprotein E, clusterin and S-100. HLA-DR expression is particularly unique for non-immunocompetent cells (although it is frequently expressed by cells early in an immune reaction). Still other molecular markers associated with dysfunctional RPE cells of AMD-affected eyes include gene products associated with cell death such as: death protein, heat shock protein 70, proteasome, Cu/Zn superoxide dismutase, cathepsins, and death adaptor protein RAIDD. Furthermore, drusen biogenesis is facilitated by various immune-mediated events such as the production of autoantibodies in the sera of AMD patients. These autoantibodies are directed against drusen, the RPE and other retinal components. Accordingly, the invention provides for diagnostic assays designed to detect the presence and antigen specificity of such autoantibodies by methods known in the art, including standard immunohistochemical and Western blot techniques. Furthermore a number of immune system-associated molecules, including Ig mu, lambda, J, and kappa chains, are up-regulated in the RPE/choroid in conjunction with the formation of drusen. Accordingly, the these immune-associated molecules provide another target for protein-based (e.g. antibody-based detection methods) and nucleic acid-based (e.g. Northern, and RT-PCR methods) diagnostic assays. Still other drusen-associated molecular markers are those found in conjunction with subpopulation of choroidal cells that possess cellular processes which breach Bruch's membrane and terminate as bulbous, vesicle-filled "cores" withing the centers of drusen. Specific marker molecules associated with these dendritic cells include: CD1a, CD4, CD14, CD68, CD83, CD86 and CD45. Other molecular markers appear to be associated with drusen-associated dendritic cell cores include: PECAM, MMP 14, ubiquitin, and FGF. In yet another aspect of the invention, the drusen-associated marker may be a cytokine which facilitates the development of drusen via a receptor-ligand interaction between a dendritic cell precursor and an injured tissue. Such cytokines include: IL-1, IL-6, IL-12, TNF-alpha, and GM-CSF. Other molecules involved in drusen development include GM-CSF, heat shock proteins, and DNA fragments.

In one embodiment, the sample obtained from the subject is a blood or urine sample, obtained according to standard methods in the art. In another embodiment, a sample is derived from a tissue, which may be obtain by biopsy. Alternatively, the sample may be a DNA or RNA sample, obtained from, for example, blood or other fluid or from a tissue and is purified according to standard molecular biology methods. The markers may be detected by analyzing the presence of protein by standard techniques or by analyzing the RNA of a subject, e.g., by polymerase chain reaction (PCR), thereby determining the RNA expression levels of a DRAM or other drusen-associated marker.

In another embodiment, the invention provides a method for diagnosing, or detecting a predisposition to developing, an arterial wall disruptive disorder in a subject, comprising performing an immunoassay on a sample obtained from the subject using an antibody specific for a gene product indicative of macular degeneration, wherein detection of the presence of bound antibody indicates that the subject has macular degeneration or a predisposition to developing macular degeneration and therefore has an arterial wall disruptive disorder or a predisposition for developing an arterial wall disruptive disorder. The antibody may be obtained by standard methods and may be a monoclonal antibody or a polyclonal antibody.

In another embodiment, a kit for diagnosing arterial wall disruptive disorder is provided, comprising reagents for performing the immunoassay. In another embodiment, the kit for diagnosing arterial wall disruptive disorder comprises specific primers for amplifying a region of a chromosome having a polymorphism indicative of macular degeneration, reagents for performing DNA amplification and reagents for analyzing the amplified nucleic acid. The methods described herein may be performed, for example, by utilizing pre-packaged diagnostic kits comprising at least one probe nucleic acid, primer set; and/or antibody reagent described herein, which may be conveniently used, e.g., in clinical settings to diagnose patients exhibiting symptoms or family history of a disease or illness involving macular degeneration. The kit may detect abnormal levels, form or activity of one or more DRAM proteins, RNAs or a breakdown products of one or more DRAM proteins or RNAs. In an embodiment of the invention, the kit detects autoantibodies specific for DRAM proteins, peptides or nucleic acids. For example, the kit can comprise a labeled compound or agent capable of detecting DRAM proteins or mRNAs in a biological sample; means for determining the amount of DRAM protein in the sample (e.g., a blood, urine or biopsy sample); and means for comparing the amount of DRAM protein in a sample from a macular degeneration-afflicted subject compared to a sample from a normal, healthy subject. The compound or agent can be packaged in a suitable container. The kit can further comprise instructions for using the kit to detect DRAM mRNAs or proteins. Such a kit can comprise, e.g., one or more nucleic acid probes capable of hybridizing specifically to at least a portion of a DRAM gene or allelic variant thereof, or mutated form thereof. Preferably the kit comprises at least one oligonucleotide primer capable of differentiating between a normal DRAM gene and a DRAM gene with one or more nucleotide differences.

Another aspect of the invention pertains to an antibody specifically reactive with a DRAM or other component of drusen. See, e.g., Antibodies: A Laboratory Manual, ed. by Harlow and Lane, Cold Spring Harbor Press, 1988. A mammal, such as a mouse, a hamster or rabbit can be immunized with an immunogenic form of the peptide (e.g., an antigenic fragment which is capable of eliciting an antibody response, or a fusion protein as described above).

Techniques for conferring immunogenicity on a protein or peptide include conjugation to carriers or other techniques well known in the art. The progress of immunization can be monitored by detection of antibody titers in plasma or serum. Standard ELISA or other immunoassays can be used with the immunogen as antigen to assess the levels of antibodies.

The invention provides methods for obtaining antibodies directed at a DRAM, using similar methodologies. Anti-DRAM antibodies are useful for visualization of DRAMs in drusen, inhibiting DRAM function or accumulation or for encouraging DRAM resolution. The procedure for obtaining such antibodies is well known in the art and is provided briefly below.

Following immunization of an animal with an antigenic preparation of a DRAM polypeptide or another drusen-associated molecular marker, specific antisera can be obtained and, if desired, polyclonal antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique, Kohler and Milstein (1975), *Nature* 256: 495–497, the human B cell hybridoma technique, Kozbar et al. (1983), *Immunol. Today* 4: 72, and the EBV-hybridoma technique to produce human monoclonal antibodies. Cole et al. (1985), *Monoclonal Antibodies and Cancer Therapy*, Alan R. Liss, Inc. pp. 77–96. Hybridoma cells can be screened immunochemically for production of antibodies specifically reactive with a dendritic cell, DRAM polypeptide of the present invention and monoclonal antibodies isolated from a culture comprising such hybridoma cells.

The term antibody as used herein is intended to include fragments thereof which are also specifically reactive with one of the subject dendritic cell, DRAM polypeptides. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific, single-chain, and chimeric and humanized molecules having affinity for a dendritic cell, DRAM protein conferred by at least one CDR region of the antibody. In preferred embodiments, the antibody further comprises a label attached thereto and able to be detected, (e.g., the label can be a radioisotope, fluorescent compound, enzyme or enzyme co-factor).

Further, anti-DRAM antibodies can be used, e.g., to monitor DRAM protein levels, respectively, in an individual for determining, e.g., whether a subject has a disease or condition associated with an aberrant DRAM protein level, or allowing determination of the efficacy of a given treatment regimen for an individual afflicted with such a disorder, which is linked to arterial wall disruptive disorder. The level of DRAM polypeptides may be measured from cells in bodily fluid, such as in blood samples. Alterations in DRAM composition or DRAM protein levels are indicia of the efficacy of an agent provided for arterial wall disruptive disorder or macular degeneration.

Another application of DRAM antibodies of the present invention is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 can produce fusion proteins whose amino termini consist of B-galactosidase amino acid sequences and whose carboxy termini consist of a foreign polypeptide. Antigenic epitopes of a DRAM protein, e.g., other orthologs of a particular DRAM protein or other paralogs from the same species, can then be detected with antibodies, as, for example, reacting nitrocellulose filters lifted from infected plates with such antibodies. Positive phage detected by this assay can then be isolated from the infected plate. Thus, the presence of DRAM homologs can be detected and cloned from other animals, as can alternate isoforms (including splice variants) from humans.

The invention provides methods for identifying autoantibodies to DRAMs. For example, naturally occurring autoantibodies may be caused by an autoimmune disease involving antibodies directed at DRAMs or nucleic acids. The DRAM nucleic acids and proteins disclosed herein provide assays (e.g., immunoassays) for the detection, isolation and characterization of specific DRAM antibodies. For example, the characterization of DRAM autoantibodies encompasses the characterization and isolation of the DRAM autoantibody antigen or epitope.

4.4.1. Cell-Free Assays

Cell-free assays can be used to identify compounds which are capable of interacting with a drusen-associated marker gene product or binding partner, to thereby modify the activity of the drusen-associated marker gene protein or binding partner. Such a compound can, e.g., modify the structure of an drusen-associated marker gene protein or binding partner and thereby effect its activity. Cell-free assays can also be used to identify compounds which modulate the interaction between a drusen-associated marker gene protein and an drusen-associated marker gene binding partner, such as a target peptide. In a preferred embodiment, cell-free assays for identifying such compounds consist essentially in a reaction mixture containing an drusen-associated marker gene protein and a test compound or a library of test compounds in the presence or absence of a binding partner. A test compound can be, e.g., a derivative of an drusen-associated marker gene binding partner, e.g., a biologically inactive target peptide, or a small molecule.

Accordingly, one exemplary screening assay of the present invention includes the steps of contacting a drusen-associated marker gene protein or functional fragment thereof or a drusen-associated marker gene binding partner with a test compound or library of test compounds and detecting the formation of complexes. For detection purposes, the molecule can be labeled with a specific marker and the test compound or library of test compounds labeled with a different marker. Interaction of a test compound with a drusen-associated marker gene protein or fragment thereof or a drusen-associated marker gene binding partner can then be detected by determining the level of the two labels after an incubation step and a washing step. The presence of two labels after the washing step is indicative of an interaction.

An interaction between molecules can also be identified by using real-time BIA (Biomolecular Interaction Analysis, Pharmacia Biosensor AB) which detects surface plasmon resonance (SPR), an optical phenomenon. Detection depends on changes in the mass concentration of macromolecules at the biospecific interface, and does not require any labeling of interactants. In one embodiment, a library of test compounds can be immobilized on a sensor surface, e.g., which forms one wall of a micro-flow cell. A solution containing the drusen-associated marker gene protein, functional fragment thereof, drusen-associated marker protein analog or drusen-associated marker gene binding partner is then flown continuously over the sensor surface. A change in the resonance angle as shown on a signal recording, indicates that an interaction has occurred. This technique is further described, e.g., in BIAtechnology Handbook by Pharmacia.

Another exemplary screening assay of the present invention includes the steps of (a) forming a reaction mixture including: (i) a drusen-associated marker gene polypeptide, (ii) a drusen-associated marker gene binding partner, and (iii) a test compound; and (b) detecting interaction of the drusen-associated marker gene and the drusen-associated marker gene binding protein. The drusen-associated marker gene polypeptide and drusen-associated marker gene binding partner can be produced recombinantly, purified from a source, e.g., plasma, or chemically synthesized, as described herein. A statistically significant change (potentiation or inhibition) in the interaction of the drusen-associated marker gene and drusen-associated marker gene binding protein in the presence of the test compound, relative to the interaction in the absence of the test compound, indicates a potential agonist (mimetic or potentiator) or antagonist (inhibitor) of drusen-associated marker gene bioactivity for the test compound. The compounds of this assay can be contacted simultaneously. Alternatively, a drusen-associated marker gene protein can first be contacted with a test compound for an appropriate amount of time, following which the drusen-associated marker gene protein binding partner is added to the reaction mixture. The efficacy of the compound can be assessed by generating dose response curves from data obtained using various concentrations of the test compound. Moreover, a control assay can also be performed to provide a baseline for comparison. In the control assay, isolated and purified MFGF polypeptide or binding partner is added to a composition containing the drusen-associated marker gene protein binding partner or drusen-associated marker gene polypeptide, and the formation of a complex is quantitated in the absence of the test compound.

Complex formation between a drusen-associated marker gene protein and a drusen-associated marker gene binding partner may be detected by a variety of techniques. Modulation of the formation of complexes can be quantitated using, for example, detectably labeled proteins such as radiolabeled, fluorescently labeled, or enzymatically labeled drusen-associated marker gene proteins or drusen-associated marker gene binding partners, by immunoassay, or by chromatographic detection.

Typically, it will be desirable to immobilize either drusen-associated marker gene protein or its binding partner to facilitate separation of complexes from uncomplexed forms of one or both of the proteins, as well as to accommodate automation of the assay. Binding of drusen-associated marker gene protein to a drusen-associated marker gene product binding partner, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase (GST) fusion proteins can be adsorbed onto glutathione sepharose beads (Sigma Chemical, St. Louis, Mo.) or glutathione derivatized microtitre plates, which are then combined with the drusen-associated marker gene product binding partner, e.g., an $^{35}$S-labeled drusen-associated marker gene product binding partner, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintilant), or in the supernatant after the complexes are subsequently dissociated. Alternatively, the complexes can be dissociated from the matrix, separated by SDS-PAGE, and the level of drusen-associated marker gene product protein or associated binding partner found in the bead fraction quantitated from the gel using standard electrophoretic techniques such as described in the appended examples.

Other techniques for immobilizing proteins on matrices are also available for use in the subject assay. For instance, either drusen-associated marker gene product or its cognate binding partner can be immobilized utilizing conjugation of biotin and streptavidin. For instance, biotinylated drusen-associated marker molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with drusen-associated marker gene product can be derivatized to the wells of the plate, and MFGF trapped in the wells by antibody conjugation. As above, preparations of a drusen-associated marker gene binding protein and a test compound are incubated in the presenting wells of the plate, and the amount of complex trapped in the well can be quantitated. Exemplary methods for detecting such complexes, in addition to those described above for the GST-immobilized complexes, include immunodetection of complexes using antibodies reactive with the drusen-associated marker gene product binding partner, or which are reactive with drusen-associated marker gene protein and compete with the binding partner; as well as enzyme-linked assays which rely on detecting an enzymatic activity associated with the binding partner, either intrinsic or extrinsic activity. In the instance of the latter, the enzyme can be chemically conjugated or provided as a fusion protein with the drusen-associated marker gene binding partner. To illustrate, the drusen-associated marker gene product binding partner can be chemically cross-linked or genetically fused with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) J Biol Chem 249:7130).

For processes which rely on immunodetection for quantitating one of the proteins trapped in the complex, antibodies against the protein, such as anti-drusen-associated marker gene product antibodies, can be used. Alternatively, the protein to be detected in the complex can be "epitope tagged" in the form of a fusion protein which includes, in addition to the drusen-associated marker gene sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharmacia, NJ).

Cell-free assays can also be used to identify compounds which interact with an drusen-associated marker gene protein and modulate an activity of an drusen-associated marker gene protein. Accordingly, in one embodiment, a drusen-associated marker gene product protein is contacted with a test compound and the catalytic activity of drusen-associated marker gene is monitored. In one embodiment, the abililty of drusen-associated marker gene product to bind a target molecule is determined. The binding affinity of drusen-associated marker gene to a target molecule can be determined according to methods known in the art. Determination of the enzymatic activity of drusen-associated marker gene can be performed with the aid of the substrate furana-cryloyl-L-phenylalanyl-glycyl-glycine (FAPGG) under conditions described in Holmquist et al. (1979) Anal. Biochem. 95:540 and in U.S. Pat. No. 5,259,045.

4.4.2. Cell Based Assays

In addition to cell-free assays, such as described above, drusen-associated marker gene proteins as provided by the present invention, facilitate the generation of cell-based assays, e.g., for identifying small molecule agonists or antagonists. In one embodiment, a cell expressing a drusen-associated marker gene product receptor protein on the outer surface of its cellular membrane is incubated in the presence of a test compound alone or in the presence of a test compound and a drusen-associated marker gene protein and the interaction between the test compound and the drusen-associated marker gene product receptor protein or between the drusen-associated marker gene protein and the drusen-associated marker gene product receptor is detected, e.g., by using a microphysiometer (McConnell et al. (1992) Science 257:1906). An interaction between the drusen-associated marker gene product receptor protein and either the test compound or the MFGF protein is detected by the microphysiometer as a change in the acidification of the medium. This assay system thus provides a means of identifying molecular antagonists which, for example, function by interfering with drusen-associated marker gene product-receptor interactions, as well as molecular agonist which, for example, function by activating a drusen-associated marker gene receptor.

Cell based assays can also be used to identify compounds which modulate expression of an drusen-associated marker gene, modulate translation of a drusen-associated marker gene mRNA, or which modulate the stability of a drusen-associated marker gene mRNA or protein. Accordingly, in one embodiment, a cell which is capable of producing drusen-associated marker gene, e.g., a retinal epithelial cell, is incubated with a test compound and the amount of drusen-associated marker gene produced in the cell medium is measured and compared to that produced from a cell which has not been contacted with the test compound. The specificity of the compound vis a vis drusen-associated marker gene can be confirmed by various control analysis, e.g., measuring the expression of one or more control genes. Compounds which can be tested include small molecules, proteins, and nucleic acids. In particular, this assay can be used to determine the efficacy of drusen-associated marker gene antisense molecules or ribozymes.

In another embodiment, the effect of a test compound on transcription of an drusen-associated marker gene is determined by transfection experiments using a reporter gene operatively linked to at least a portion of the promoter of an drusen-associated marker gene. A promoter region of a gene can be isolated, e.g., from a genomic library according to methods known in the art. The reporter gene can be any gene encoding a protein which is readily quantifiable, e.g, the luciferase or CAT gene. Such reporter gene are well known in the art.

This invention further pertains to novel agents identified by the above-described screening assays and uses thereof for treatments as described herein.

4.5 Predictive Medicine

The invention further features predictive medicines, which are based, at least in part, on the identity of the novel AAA/AMD-associated genes and alterations in the genes and related pathway genes, which affect the expression level and/or function of the encoded protein in a subject. For example, the invention provides a method for diagnosing, or determining a predisposition to, arterial wall disruptive disorder in a subject, comprising isolating a nucleic acid from a subject and genotyping the nucleic acid wherein at least one allele from a macular degeneration-associated haplotype is predictive of an increased risk of arterial wall disruptive disorder. In another embodiment the invention provides a method for diagnosing, or determining a predisposition to, arterial wall disruptive disorder in a subject having family members diagnosed with macular degeneration, comprising isolating a nucleic acid from a subject, amplifying the nucleic acid with primers which amplify a region of a chromosome corresponding to a polymorphic marker for AMD and analyzing the amplification product, wherein the presence of a polymorphism indicative of an allele type linked to macular degeneration is indicative of an allele type linked to arterial wall disruptive disorder or a predisposition for developing arterial wall disruptive disorder. In yet another embodiment, the invention provides a method for diagnosing, or determining a predisposition to, arterial wall disruptive disorder in a subject having family members diagnosed with macular degeneration, comprising isolating a genomic nucleic acid from a subject amplifying short tandem repeat sequences in the genomic DNA to obtain a genotype, comparing the genotype to the genotype of known DNA sequences to detect nucleotide sequence polymorphisms and determining the presence or absence of a polymorphism in the genomic DNA of the subject, wherein the presence of a polymorphism indicative of an allele type linked to macular degeneration is indicative of an allele type linked to arterial wall disruptive disorder or a predisposition for developing arterial wall disruptive disorder. In a preferred embodiment, the genotype substantially corresponds to a region of the short arm of human chromosome 2 bordered by marker D2S2352 and D2S1364.

In additional preferred embodiments, genotyping of arterial wall disruptive disorder can be performed by detecting a polymorphism in one or more of the following chromosomal regions, which are well known in the art for indicating a predisposition to macular degeneration: 1p21–q13, for recessive Stargardt's disease or fundus flavi maculatus (Allikmets, R. et al. *Science* 277:1805–1807, 1997; Anderson, K. L. et al., *Am. J. Hum. Genet.* 55:1477, 1994; Cremers, F. P. M. et al., *Hum. Mol. Genet.* 7:355–362, 1998; Gerber, S. et al., *Am. J. Hum. Genet.* 56:396–399, 1995; Gerber, S. et al., *Genomics* 48:139–142, 1998; Kaplan, J. et al., *Nat. Genet.* 5:308–311, 1993; Kaplan, J. et al., *Am. J. Hum. Genet.* 55:190, 1994; Martinez-Mir, A. et al., *Genomics* 40:142–146, 1997; Nasonkin, I. et al., *Hum. Genet.* 102: 21–26, 1998; Stone, E. M. et al., *Nat. Genet.* 20:328–329, 1998); 1q25–q31, for recessive age related macular degeneration (Klein, M. L. et al., *Arch. Ophthalmol.* 116:1082–1088, 1988); 2p16, for dominant radial macular drusen, dominant Doyne honeycomb retinal degeneration or Malattia Leventinese (Edwards, A. O. et al., *Am. J. Ophthalmol.* 126:417–424, 1998; Heon, E. et al., *Arch. Ophthalmol.* 114:193–198, 1996; Heon, E. et al.,. *Invest. Ophthalmol Vis. Sci.* 37:1124, 1996; Gregory, C. Y. et al., *Hum. Mol. Genet.* 7:1055–1059, 1996); 6p21.2-cen, for dominant macular degeneration, adult vitelliform (Felbor, U. et al. *Hum. Mutat.* 10:301–309, 1997); 6p21.1 for dominant cone dystrophy (Payne, A. M. et al. *Am. J. Hum. Genet.* 61:A290, 1997; Payne, A. M. et al., *Hum. Mol. Genet.* 7:273–277, 1998; Sokol, I. et al., *Mol. Cell.* 2:129–133, 1998); 6q, for dominant cone-rod dystrophy (Kelsell, R. E. et al. *Am. J. Hum. Genet.* 63:274–279, 1998); 6q11–q15, for dominant macular degeneration, Stargardt's-like (Griesinger, I. B. et al., *Am. J. Hum. Genet.* 63:A30, 1998; Stone, E. M. et al., *Arch. Ophthalmol.* 112:765–772, 1994); 6q14–q16.2, for dominant macular degeneration, North Carolina Type (Kelsell, R. E. et al., *Hum. Mol. Genet.* 4:653–656, 1995; Robb, M. F. et al., *Am. J. Ophthalmol.* 125:502–508, 1998; Sauer, C. G. et al., *J. Med. Genet.* 34:961–966, 1997; Small, K. W. et al., *Genomics* 13:681–685, 1992; Small, K. W. et al., *Mol. Vis.* 3:1, 1997); 6q25–q26, dominant retinal cone dystrophy 1 (Online Mendelian Inheritance in Man (™). Center for Medical Genetics, Johns Hopkins University, and National Center for Biotechnology Information, National Library of Medicine. http://www3.ncbi.nlm.nih.gov/omim (1998); 7p21–p15, for dominant cystoid macular degeneration (Inglehearn, C. F. et al., *Am. J. Hum. Genet.* 55:581–582, 1994; Kremer, H. et al., *Hum. Mol. Genet.* 3:299–302, 1994); 7q31.3–32, for dominant tritanopia, protein: blue cone opsin (Fitzgibbon, J. et al., *Hum. Genet.* 93:79–80, 1994; Nathans, J. et al., *Science* 193:193–232, 1986; Nathans, J. et al., *Ann. Rev. Genet.* 26:403–424, 1992; Nathans, J. et al., *Am. J. Hum. Genet.* 53:987–1000, 1993; Weitz, C. J. et al., *Am. J. Hum. Genet.* 50:498–507, 1992; Weitz, C. J. et al., *Am. J. Hum. Genet.* 51:444–446, 1992); not 8q24, for dominant macular degeneration, atypical vitelliform (Daiger, S. P. et al., In 'Degenerative Retinal Diseases', LaVail, et al., eds. Plenum Press, 1997; Ferrell, R. E. et al., *Am. J. Hum. Genet.* 35:78–84, 1983; Leach, R. J. et al., *Cytogenet. Cell Genet.* 75:71–84, 1996; Sohocki, M. M. et al., *Am. J. Hum. Genet.* 61:239–241, 1997); 11p12–q13, for dominant macular degeneration, Best type (bestrophin) (Forsman, K. et al., *Clin. Genet.* 42:156–159, 1992; Graff, C. et al., *Genomics,* 24:425–434, 1994; Petrukhin, K. et al., *Nat. Genet.* 19:241–247, 1998; Marquardt, A. et al., *Hum. Mol. Genet.* 7:1517–1525, 1998; Nichols, B. E. et al., *Am. J. Hum. Genet.* 54:95–103, 1994; Stone, E. M. et al., *Nat. Genet.* 1:246–250, 1992; Wadeilus, C. et al., *Am. J. Hum. Genet.* 53:1718, 1993; Weber, B. et al., *Am. J. Hum. Genet.* 53:1099, 1993; Weber, B. et al., *Am. J. Hum. Genet.* 55:1182–1187, 1994; Weber, B. H., *Genomics* 20: 267–274, 1994; Zhaung, Z. et al., *Am. J. Hum. Genet.* 53:1112, 1993); 13q34, for dominant macular degeneration, Stargardt type (Zhang, F. et al., *Arch. Ophthalmol.* 112:759–764, 1994); 16p12.1, for recessive Batten disease (ceroid-lipofuscinosis, neuronal 3), juvenile; protein: Batten disease protein (Batten Disease Consortium, *Cell* 82:949–957, 1995; Eiberg, H. et al., *Clin. Genet.* 36:217–218, 1989; Gardiner, M. et al., *Genomics* 8:387–390, 1990; Mitchison, H. M. et al., *Am. J. Hum. Genet.* 57:312–315, 1995, Mitchison, H. M. et al., *Am. J. Hum. Genet.* 56:654–662, 1995; Mitchison, H. M. et al., *Genomics* 40:346–350, 1997; Munroe, P. B. et al., *Am. J. Hum. Genet.* 61:310–316, 1997; 17p, for dominant areolar choroidal dystrophy (Lotery, A. J. et al., *Ophthalmol. Vis. Sci.* 37:1124, 1996); 17p13–p12, for dominant cone dystrophy, progressive (Balciuniene, J. et al., *Genomics* 30:281–286, 1995; Small, K. W. et al., *Am. J. Hum. Genet.* 57:A20, 1995; Small, K. W. et al., *Am. J. Ophthalmol.* 121:13–18, 1996); 17q, for cone rod dystrophy (Klystra, J. A. et al., *Can. J Ophthalmol.* 28:79–80, 1993); 18q21.1–q21.3, for cone-rod dystrophy, de Grouchy syndrome (Manhant, S. et al., *Am. J. Hum. Genet.* 57:A96, 1995; Warburg, M. et al., *Am. J. Med. Genet.* 39:288–293, 1991); 19q13.3, for dominant cone-rod dystrophy; recessive, dominant and 'de novo' Leber congenital amaurosis; dominant RP; cone-rod otx-like photoreceptor homeobox transcription factor (Bellingham, J. et al., In 'Degenerative Retinal Diseases', LaVail, et al., eds. Plenum Press, 1997; Evans, K. et al., *Nat. Genet.* 6:210–213, 1994; Evans, K. et al., *Arch. Ophthalmol.* 113:195–201, 1995; Freund, C. L. et al., *Cell* 91:543–553, 1997; Freund, C. L. et al., *Nat. Genet.* 18:311–312, 1998; Gregory, C. Y. et al., *Am. J. Hum. Genet.* 55:1061–1063, 1994; Li, X. et al., *Proc. Natl. Acad. Sci USA* 95:1876–1881, 1998; Sohocki, M. M. et al., *Am. J. Hum. Genet.* 63:1307–1315, 1998; Swain, P. K. et al., *Neuron* 19:1329–1336, 1987; Swaroop, A. et al., *Hum. Mol. Genet. In press,* 1999); 22q12.1–q13.2, for dominant Sorsby's findus dystrophy (TIMP3) (Felbor, U. et al., *Hum. Mol. Genet.* 4:2415–2416, 1995; Felbor, U. et al., *Am. J. Hum. Genet.* 60:57–62, 1997; Jacobson, S. E. et al., *Nat. Genet.* 11:27–32, 1995; Peters, A. et al., *Retina* 15:480–485, 1995; Stohr, H. et al., *Genome Res.* 5:483–487, 1995; Weber, B. H. F. et al., *Nat. Genet.* 8:352–355, 1994; Weber, B. H. F. et al., *Nat. Genet.* 7:158–161, 1994; Wijesvriya, S. D. et al., *Genome Res.* 6:92–101, 1996); and Xp11.4, for X-linked cone dystrophy (Bartley, J. et al., *Cytogenet. Cell. Genet.* 51:959, 1989; Bergen, A. A. B. et al., *Genomics* 18:463–464, 1993; Dash-Modi, A. et al., *Invest. Ophthalmol. Vis. Sci.* 37:998, 1996; Hong, H.-K., *Am. J. Hum. Genet* 55:1173–1181, 1994; Meire, F. M. et al., *Br. J. Ophthalmol.* 78:103–108, 1994; Seymour, A. B. et al., *Am. J. Hum. Genet.* 62:122–129, 1998); all of which have been identified and characterized as harboring a polymorphism or mutation linked to macular degeneration; the above references are herein incorporated by. Thus, through the existence of polymorphisms in the art and of gene sequences of mutant alleles, the art provides guidance useful for designing appropriate primer pairs for performing PCR for any particular mutant gene that causes or is associated with macular degeneration. By detecting macular degeneration in a subject or a genetic predisposition to macular degeneration, the subject's genetic predisposition to arterial wall disruptive disorder is also determined. In a preferred embodiment, the arterial wall disruptive disorder is AAA or TAAA and the macular degeneration is AMD of the DS/CNV type.

For example, information obtained using the diagnostic assays described herein (alone or in conjunction with information on another genetic defect, which contributes to the same disease) is useful for diagnosing or confirming that a symptomatic subject (e.g. a subject symptomatic for AMD), has a genetic defect (e.g. in an AMD-associated gene or in a gene that regulates the expression of a drusen-associated marker gene), which causes or contributes to the particular disease or disorder. Alternatively, the information (alone or in conjunction with information on another genetic defect, which contributes to the same disease) can be used prognostically for predicting whether a non-symptomatic subject is likely to develop a disease or condition, which is caused by or contributed to by an abnormal activity or protein level in a subject. Based on the prognostic information, a doctor can recommend a regimen (e.g. diet or exercise) or therapeutic protocol, useful for preventing or prolonging onset of the particular disease or condition in the individual.

In addition, knowledge of the particular alteration or alterations, resulting in defective or deficient genes or proteins in an individual (the genetic profile), alone or in conjunction with information on other genetic defects contributing to the same disease (the genetic profile of the particular disease) allows customization of therapy for a particular disease to the individual's genetic profile, the goal of "pharmacogenomics". For example, an individual's genetic profile or the genetic profile of a disease or condition, to which genetic alterations cause or contribute, can enable a doctor to 1) more effectively prescribe a drug that will address the molecular basis of the disease or condition; and 2) better determine the appropriate dosage of a particular drug. For example, the expression level of drusen-associated molecular marker proteins, alone or in conjunction with the expression level of other genes, known to contribute to the same disease, can be measured in many patients at various stages of the disease to generate a transcriptional or expression profile of the disease. Expression patterns of individual patients can then be compared to the expression profile of the disease to determine the appropriate drug and dose to administer to the patient.

The ability to target populations expected to show the highest clinical benefit, based on the AAA/AMD genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling (e.g. since the use of a drusen-associated molecular marker gene as a marker is useful for optimizing effective dose).

4.6 Transgenic Animals

The invention further provides for transgenic animals, which can be used for a variety of purposes, e.g., to identify genetic loci involved in the common etiology of AAA and AMD, and, further, to create animal models for the treatment of AMD and AAA.

The transgenic animals can be animals containing a transgene, such as reporter gene, under the control of a drusen-associated marker gene promoter or fragment thereof. These animals are useful, e.g., for identifying drugs that modulate production of the drusen-associated molecular, such as by modulating vitronectin, Factor X, HLA-DR, IL-6 or elastin gene expression. A target gene promoter can be isolated, e.g., by screening of a genomic library with an appropriate cDNA fragment and characterized according to methods known in the art. In a preferred embodiment of the present invention, the transgenic animal containing a reporter gene is used to screen a class of bioactive molecules for their ability to modulate expression of a drusen-associated molecular marker such as a DRAM. Yet other non-human animals within the scope of the invention include those in which the expression of the endogenous target gene has been mutated or "knocked out". A "knock out" animal is one carrying a homozygous or heterozygous deletion of a particular gene or genes. These animals could be useful to determine whether the absence of the target will result in a specific phenotype, in particular whether these mice have or are likely to develop a specific disease, such as high susceptibility to AAA and/or AMD. Furthermore these animals are useful in screens for drugs which alleviate or attenuate the disease condition resulting from the mutation of the AAA/AMD-associated polymorphic gene as outlined below. These animals are also useful for determining the effect of a specific amino acid difference, or allelic variation, in a target gene. That is, the target knock out animals can be crossed with transgenic animals expressing, e.g., a mutated form or allelic variant of the target gene containing an AAA/AMD-associated polymorphic marker, thereby resulting in an animal which expresses only the mutated protein and not the wild-type target gene product.

Methods for obtaining transgenic and knockout non-human animals are well known in the art. Knock out mice are generated by homologous integration of a "knock out" construct into a mouse embryonic stem cell chromosome which encodes the gene to be knocked out. In one embodiment, gene targeting, which is a method of using homologous recombination to modify an animal's genome, can be used to introduce changes into cultured embryonic stem cells. By targeting a specific gene of interest in ES cells, these changes can be introduced into the germlines of animals to generate chimeras. The gene targeting procedure is accomplished by introducing into tissue culture cells a DNA targeting construct that includes a segment homologous to a target locus, and which also includes an intended sequence modification to the genomic sequence (e.g., insertion, deletion, point mutation). The treated cells are then screened for accurate targeting to identify and isolate those which have been properly targeted.

Gene targeting in embryonic stem cells is in fact a scheme contemplated by the present invention as a means for disrupting a target gene function through the use of a targeting transgene construct designed to undergo homologous recombination with one or more Target genomic sequences. The targeting construct can be arranged so that, upon recombination with an element of a Target gene, a positive selection marker is inserted into (or replaces) coding sequences of the gene. The inserted sequence functionally disrupts the Target gene, while also providing a positive selection trait. Exemplary targeting constructs are described in more detail below.

Generally, the embryonic stem cells (ES cells) used to produce the knockout animals will be of the same species as the knockout animal to be generated. Thus for example, mouse embryonic stem cells will usually be used for generation of knockout mice.

Embryonic stem cells are generated and maintained using methods well known to the skilled artisan such as those described by Doetschman et al. (1985) *J. Embryol. Exp. MoMFGFhol.* 87:27–45). Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. One mouse strain that is typically used for production of ES cells, is the 129J strain. Another ES cell line is murine cell line D3 (American Type Culture Collection, catalog no. CKL 1934) Still another preferred ES cell line is the WW6 cell line (Ioffe et al. (1995) *PNAS* 92:7357–7361). The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) *Current Topics in Devel. Biol.* 20:357–371); and by Hogan et al. (Manipulating the Mouse Embryo: A Laboratory Manual, Cold Spring Harbor Laboratory Press, Cold Spring Harbor, N.Y. [1986].

A knock out construct refers to a uniquely configured fragment of nucleic acid which is introduced into a stem cell line and allowed to recombine with the genome at the chromosomal locus of the gene of interest to be mutated. Thus a given knock out construct is specific for a given gene to be targeted for disruption. Nonetheless, many common elements exist among these constructs and these elements are well known in the art. A typical knock out construct contains nucleic acid fragments of not less than about 0.5 kb nor more than about 10.0 kb from both the 5' and the 3' ends of the genomic locus which encodes the gene to be mutated. These two fragments are separated by an intervening fragment of nucleic acid which encodes a positive selectable marker, such as the neomycin resistance gene (neo$^R$). The resulting nucleic acid fragment, consisting of a nucleic acid from the extreme 5' end of the genomic locus linked to a nucleic acid encoding a positive selectable marker which is in turn linked to a nucleic acid from the extreme 3' end of the genomic locus of interest, omits most of the coding sequence for the gene of interest to be knocked out. When the resulting construct recombines homologously with the chromosome at this locus, it results in the loss of the omitted coding sequence, otherwise known as the structural gene, from the genomic locus. A stem cell in which such a rare homologous recombination event has taken place can be selected for by virtue of the stable integration into the genome of the nucleic acid of the gene encoding the positive selectable marker and subsequent selection for cells expressing this marker gene in the presence of an appropriate drug (neomycin in this example).

Variations on this basic technique also exist and are well known in the art. For example, a "knock-in" construct refers to the same basic arrangement of a nucleic acid encoding a 5' genomic locus fragment linked to nucleic acid encoding a positive selectable marker which in turn is linked to a nucleic acid encoding a 3' genomic locus fragment, but which differs in that none of the coding sequence is omitted and thus the 5' and the 3' genomic fragments used were initially contiguous before being disrupted by the introduction of the nucleic acid encoding the positive selectable marker gene. This "knock-in" type of construct is thus very useful for the construction of mutant transgenic animals when only a limited region of the genomic locus of the gene to be mutated, such as a single exon, is available for cloning and genetic manipulation. Alternatively, the "knock-in" construct can be used to specifically eliminate a single functional domain of the targetted gene, resulting in a transgenic animal which expresses a polypeptide of the targetted gene which is defective in one function, while retaining the function of other domains of the encoded polypeptide. This type of "knock-in" mutant frequently has the characteristic of a so-called "dominant negative" mutant because, especially in the case of proteins which homomultimerize, it can specifically block the action of (or "poison") the polypeptide product of the wild-type gene from which it was derived. In a variation of the knock-in technique, a marker gene is integrated at the genomic locus of interest such that expression of the marker gene comes under the control of the transcriptional regulatory elements of the targeted gene. A marker gene is one that encodes an enzyme whose activity can be detected (e.g., β-galactosidase), the enzyme substrate can be added to the cells under suitable conditions, and the enzymatic activity can be analyzed. One skilled in the art will be familiar with other useful markers and the means for detecting their presence in a given cell. All such markers are contemplated as being included within the scope of the teaching of this invention.

As mentioned above, the homologous recombination of the above described "knock out" and "knock in" constructs is very rare and frequently such a construct inserts nonhomologously into a random region of the genome where it has no effect on the gene which has been targeted for deletion, and where it can potentially recombine so as to disrupt another gene which was otherwise not intended to be altered. Such nonhomologous recombination events can be selected against by modifying the abovementioned knock out and knock in constructs so that they are flanked by negative selectable markers at either end (particularly through the use of two allelic variants of the thymidine kinase gene, the polypeptide product of which can be selected against in expressing cell lines in an appropriate tissue culture medium well known in the art—i.e. one containing a drug such as 5-bromodeoxyuridine). Thus a preferred embodiment of such a knock out or knock in construct of the invention consist of a nucleic acid encoding a negative selectable marker linked to a nucleic acid encoding a 5' end of a genomic locus linked to a nucleic acid of a posit ive selectable marker which in turn is linked to a nucleic acid encoding a 3' end of the same genomic locus which in turn is linked to a second nucleic acid encoding a negative selectable marker Nonhomologous recombination between the resulting knock out construct and the genome will usually result in the stable integration of one or both of these negative selectable marker genes and hence cells which have undergone nonhomologous recombination can be selected against by growth in the appropriate selective media (e.g. media containing a drug such as 5-bromodeoxyuridine for example). Simultaneous selection for the positive selectable marker and against the negative selectable marker will result in a vast enrichment for clones in which the knock out construct has recombined homologously at the locus of the gene intended to be mutated. The presence of the predicted chromosomal alteration at the targeted gene locus in the resulting knock out stem cell line can be confirmed by means of Southern blot analytical techniques which are well known to those familiar in the art. Alternatively, PCR can be used.

Each knockout construct to be inserted into the cell must first be in the linear form. Therefore, if the knockout construct has been inserted into a vector (described infra), linearization is accomplished by digesting the DNA with a suitable restriction endonuclease selected to cut only within the vector sequence and not within the knockout construct sequence.

For insertion, the knockout construct is added to the ES cells under appropriate conditions for the insertion method chosen, as is known to the skilled artisan. For example, if the ES cells are to be electroporated, the ES cells and knockout construct DNA are exposed to an electric pulse using an electroporation machine and following the manufacturer's guidelines for use. After electroporation, the ES cells are typically allowed to recover under suitable incubation conditions. The cells are then screened for the presence of the knock out construct as explained above. Where more than one construct is to be introduced into the ES cell, each knockout construct can be introduced simultaneously or one at a time.

After suitable ES cells containing the knockout construct in the proper location have been identified by the selection techniques outlined above, the cells can be inserted into an embryo. Insertion may be accomplished in a variety of ways known to the skilled artisan, however a preferred method is by microinjection. For microinjection, about 10–30 cells are collected into a micropipet and injected into embryos that are at the proper stage of development to permit integration of the foreign ES cell containing the knockout construct into the developing embryo. For instance, the transformed ES cells can be microinjected into blastocytes. The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan, and are set forth by, e.g., Bradley et al. (supra).

While any embryo of the right stage of development is suitable for use, preferred embryos are male. In mice, the preferred embryos also have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2–3 days pseudopregnant.

Offspring that are born to the foster mother may be screened initially for mosaic coat color where the coat color selection strategy (as described above, and in the appended examples) has been employed. In addition, or as an alternative, DNA from tail tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from mice that are the product of this cross, as well as mice that are known heterozygotes and wild type mice.

Other means of identifying and characterizing the knockout offspring are available. For example, Northern blots can be used to probe the mRNA for the presence or absence of transcripts encoding either the gene knocked out, the marker gene, or both. In addition, Western blots can be used to assess the level of expression of the Target gene knocked out in various tissues of the offspring by probing the Western blot with an antibody against the particular Target protein, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Yet other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of a Target-gene can be controlled by recombinase sequences (described infra).

Animals containing more than one knockout construct and/or more than one transgene expression construct are prepared in any of several ways. The preferred manner of preparation is to generate a series of mammals, each containing one of the desired transgenic phenotypes. Such animals are bred together through a series of crosses, back-crosses and selections, to ultimately generate a single animal containing all desired knockout constructs and/or expression constructs, where the animal is otherwise congenic (genetically identical) to the wild type except for the presence of the knockout construct(s) and/or transgene(s).

A Target transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of a Target protein can be essential for many forms of lineage analysis and can additionally provide a means to assess the effects of, for example, lack of Target expression which might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques, which allow for the expression of transgenes can be regulated via site-specific genetic manipulation in vivo, are known to those skilled in the art. For instance, genetic systems are available which allow for the regulated expression of a recombinase that catalyzes the genetic recombination of a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject Target proteins. For example, excision of a target sequence which interferes with the expression of a recombinant Target gene, such as one which encodes an antagonistic homolog or an antisense transcript, can be designed to activate expression of that gene. This interference with expression of the protein can result from a variety of mechanisms, such as spatial separation of the Target gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

The transgenic animals of the present invention all include within a plurality of their cells a transgene of the present invention, which transgene alters the phenotype of the "host cell" with respect to regulation of cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In an illustrative embodiment, either the cre/loxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251: 1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant Target protein can be regulated via control of recombinase expression.

Use of the cre/loxP recombinase system to regulate expression of a recombinant Target protein requires the construction of a transgenic animal containing transgenes encoding both the Cre recombinase and the subject protein. Animals containing both the Cre recombinase and a recombinant Target gene can be provided through the construction of "double" transgenic animals. A convenient method for providing such animals is to mate two transgenic animals each containing a transgene, e.g., a Target gene and recombinase gene.

One advantage derived from initially constructing transgenic animals containing a Target transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic Target transgene is silent will allow the study of progeny from that founder in which disruption of Target mediated induction in a particular tissue or at certain developmental stages would result in, for example, a lethal phenotype.

Similar conditional transgenes can be provided using prokaryotic promoter sequences which require prokaryotic proteins to be simultaneous expressed in order to facilitate expression of the Target transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, a TargetA transgene could remain silent into adulthood until "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with $H-2^b$, $H-2^d$ or $H-2^q$ haplotypes such as C57BL/6 or DBA/1. The line(s) used to practice this invention may themselves be transgenics, and/or may be knock-outs (i.e., obtained from animals which have one or more genes partially or completely suppressed).

In one embodiment, the transgene construct is introduced into a single stage embryo. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. As set out above, the exogenous genetic material will, in certain embodiments, be a DNA sequence which results in the production of a Target protein (either agonistic or antagonistic), and antisense transcript, or a Target mutant. Further, in such embodiments the sequence will be attached to a transcriptional control element, e.g., a promoter, which preferably allows the expression of the transgene product in a specific type of cell.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J*. 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

4.7 Therapeutics

In another aspect, the invention provides methods for treating or preventing the development of arterial wall disruptive disorder in a subject by administering a pharmaceutically effective amount of a macular degeneration therapeutic. The macular degeneration therapeutic may be an anti-inflammatory agent, preferably an antagonists of TNF-a, IL-1, GM-CSF, IL-4 or IL-13. The therapeutic may also be IL-10, M-CSF, IL-6 and IL-4 or an agonist thereof. Any therapeutic that helps to decrease drusen formation or DS/CNV may be used, as it may also treat the concurrent arterial wall disruptive disorder. In a preferred embodiment, the agent is selected from the group consisting of cytokines, chemokines and agonists and antagonists thereof. Useful therapeutics include agents that inhibit inflammation.

In another embodiment, the macular degeneration therapeutic is an inhibitor of the expression of one or more DRAMs, such as, for example, amyloid A protein, amyloid P component, antichymotrypsin, apolipoprotein E, b2 microglobulin, complement 3, complement C5, complement C5b-9 terminal complexes, factor X, fibrinogen, immunoglobulins (kappa and lambda), prothrombin, thrombospondin or vitronectin. In an another embodiment, the invention provides method for treating a drusen associated disease by modulating the production of DRAMs, e.g., inhibiting or antagonizing their gene expression or activity. The accumulation of amyloid P and $\alpha_1$-antichymotrypsin (an inhibitor of serine proteases) in drusen may act to counterbalance attempts by RPE or choroidal cells to clear drusen proteolytically. For example, amyloid P is also found in non-amyloid deposits associated with atherosclerosis (Niculescu, et al., 1987), keratin intermediate filament aggregates (Hintner, et al., 1988), and dense deposits associated with glomerulonephropathy (Yang, et al., 1992). It associates with elastic fibers and may function as an protease inhibitor in vivo (Li and McAdam, 1984; Vachino, et al., 1988). It is also a normal component of Bruch's membrane, where it might protect the elastic lamina against enzymatic degradation (Kivela, et al., 1994). The downregulation of the biosynthesis of these proteins is therefore important for inhibiting drusen formation or facilitating drusen clearance or resolution. Inhibiting of drusen formation or facilitating drusen clearance or resolution may be accomplished by a number of regimes, such as (1) inhibition of RNA synthesis for one or more DRAMs, (2) enhancement of RNA turnover or degradation of one or more DRAMs, (3) inhibition of translation of RNA for one or more DRAMs into protein, (4) inhibition of protein processing or transport of one or more DRAMs; (5) inhibition of drusen formation by blocking particular protein binding sites on one or more factors which participate in inter- and intra-molecular binding necessary for the association of DRAMs which results in a drusen deposit; (6) digestion or perturbation of protein deposits (e.g., using enzymes); (7) targeting and destroying DRAMs in situ (e.g., using enzyme-antibody techniques). DRAMs may be targeted by using photoreactive laser therapy, for example, or other means for targeting and destroying a protein in situ which are well known in the art. Such means may include antibodies conjugated to a reactive group such as a protease or chemical substance which, when activated, cleaves or denatures the individual components or interferes with the interaction of two or more components.

In another embodiment, therapeutics for drusen-associated diseases include agents which alter the gene expression of factors that regulate the expression of one or more DRAMs. Such agents may be "antagonists" which inhibit, either directly or indirectly, DRAM biosynthesis. The agent may specifically inhibit the transcription or translation of a DRAM, for example. Alternatively, it may be preferable to upregulate either directly or indirectly a gene or genes which will increase the synthesis of a naturally occurring therapeutic agent. For example, the increased gene expression of a proteolytic enzyme that degrades one or more DRAMS or a cytokine or drug that modulates immune responses may be desired.

The invention is therefore also useful for monitoring the efficacy of a drusen therapeutic or preventative treatment, the absence of core formation, the disappearance of drusen or of a drusen core providing evidence of efficacy of the therapeutic or treatment.

In one aspect, the therapeutics of the invention relate to antisense therapy. As used herein, "antisense" therapy refers to administration or in situ generation of oligonucleotide molecules or their derivatives which specifically hybridize (e.g., bind) under cellular conditions, with the cellular mRNA and/or genomic DNA encoding one or more DRAMs so as to inhibit expression of that protein, e.g., by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a DRAM protein. Alternatively, the antisense construct can be an oligonucleotide probe which is generated ex vivo and which, when introduced into the cell causes inhibition of expression by hybridizing with the mRNA and/or genomic sequences of a DRAM gene. Such oligonucleotide probes are preferably modified oligonucleotides which are resistant to endogenous nucleases, e.g., exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996, 5,264,564 and 5,256,775). Approaches to constructing oligomers useful in antisense therapy are well known in the art. With respect to antisense DNA, oligodeoxyribonucleotides derived from the translation initiation site, e.g., between the −10 and +10 regions of the drusen-associated component nucleotide sequence of interest, are preferred.

Antisense approaches involve the design of oligonucleotides (either DNA or RNA) that are complementary to a DRAM mRNA, or their agonists or antagonists. The antisense oligonucleotides bind to the subject mRNA transcripts and prevent translation or promote degradation of the transcript. Absolute complementarity, although preferred, is not required. In the case of double-stranded antisense nucleic acids, a single strand of the duplex DNA may thus be tested, or triplex formation may be assayed. The ability to hybridize depends on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Other features, strategies and methods of preparing and using antisense or ribozymes are found in U.S. Ser. No. 09/183,972, the teachings of which are incorporated herein by reference.

In another embodiment, the invention provides pharmaceutical compositions useful for treating or preventing arterial wall disruptive disorder, comprising an effective amount of a macular degeneration therapeutic and a therapeutically acceptable carrier. Such carriers and methods for preparing pharmaceutical preparations are found in U.S. Ser. No. 09/183,972, and are incorporated herein by reference.

In another aspect, the invention provides a method for identifying an agent for, or determining the efficacy of, an agent for treating or preventing arterial wall disruptive disorder in a subject by administering to a subject an agent at a non-toxic dosage and determining whether drusen formation or neovascularization is inhibited or has resolved. In another embodiment, the invention provides a method for identifying an agent for treating or preventing arterial wall disruptive disorder in a subject by contacting a non-human model for macular degeneration with an agent and monitoring one or more markers of macular degeneration, wherein the absence or disappearance of one or more said markers is indicative of the inhibition of arterial wall disruptive disorder. As stated above, the marker may be monitored by any of a number of art known methods for detecting proteins or nucleic acids. The marker used to detect the macular degeneration can be the presence of drusen in the sub RPE space or one or more DRAMs, such as, for example, amyloid A protein, amyloid P component, antichymotrypsin, apolipoprotein E, b2 microglobulin, complement 3, complement C5, complement C5b-9 terminal complexes, factor X, fibrinogen, immunoglobulins (kappa and lambda), prothrombin, thrombospondin and vitronectin.

In yet another aspect, the invention provides animal models for AAA that may be used to diagnose AAA or test drugs directed at treating AAA but which also will treat AMD. Animal models for AMD provide therapies for regulating the clinical progression (or regression) of small AAAs. Example 4 provides a monkey model for AMD and therefor provides an animal model for AAA. Example 5 provides a rat model for AMD and therefor provides an animal model for AAA. Preferably any animal with a macula may be used to create an animal model.

The practice of the present invention will employ, unless otherwise indicated, conventional techniques of cell biology, cell culture, genetics, molecular biology, transgenic biology, microbiology, recombinant DNA, and immunology, which are within the skill of the art. Such techniques are described in the literature. See, for example, *Molecular Cloning A Laboratory Manual*, 2nd Ed., Sambrook, Fritsch and Maniatis (eds.) (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins, eds., 1984); *Transcription And Translation* (B. D. Hames & S. J. Higgins, eds., 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos, eds., 1987, Cold Spring Harbor Laboratory); *Methods In Enzymology*, Vols. 154 and 155 (Wu et al., eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986); Rossner, B., *Fundamentals of Biostatistics*, Duxbury Press, Belmont, Calif., 370–377, 199; Lewin, B., ed. *Genes VI*, Oxford University Press, UK, 1998.

EXEMPLIFICATION

Example 1

Abdominal Aortic Aneurysm/AMD Correlation: 1998 Database

A human repository consisting of more than 2000 pairs of human donor eyes (ranging in age from one day to 106 years), which have been processed within an average postmortem time of 3.2 hours, was used to analyse the eyes for AMD. Medical and ocular histories, a family questionnaire, and blood and sera, were also obtained from most donors to determine the existence of AAA and AMD. Every eye was subjected to gross examination by a retinal specialist and processed for light (4% paraformaldehyde) and electron (2.0% formaldehyde and 2.5% glutaraldehyde) microscopy, immunohistochemistry, and various biochemical and molecular biological analyses, known in the art. Thus, DNA, RNA, fixed and frozen tissues were available for every eye in the repository. In addition, RPE cell lines were established and frozen from selected donors of all ages and races, with and without AMD. Approximately 18% of the eyes in the collection exhibit distinguishing signs of AMD (disciform scars, submacular neovascular membranes, abnormal pigmentation, and/or geographic atrophy) and/or a clinically documented history of AMD. Other ocular and systemic diseases including glaucoma, diabetes, other retinal and macular degenerations, Alzheimer's disease, Parkinson's disease, and a variety of developmental anomalies are also represented in the repository. The donor eye repository is useful for the study of specific biological processes involved in the etiology of AMD, genotype-phenotype correlations, and "candidate" molecules and genes associated with the etiology of AMD and other macular dystrophies.

Eyes from the 1998 repository will serve as an example. This database was selected because medical records of the donors was the most comprehensive. Of 207 total donors obtained in the year 1998 ("The 1998 Database"), 33 had AMD (15.9% of total) and 12 donors had AAA (5.8% of total). Of the 33 AMD donors 4 had geographic atrophy (GA, which is characteristic of the dry form of AMD) (1.9% of total), 11 had disciform scars and choroidal neovascularization (DS/CNV, which is characteristic of the wet form of AMD) (5.3% of total), and 18 others had AMD in which the diagnosis did not distinguish between the wet or dry form (8.7% of total) (Table 2).

Of the 207 total donors 12 donors had AAA. Of those 12 AAA donors 8 also had AMD (66.7% of AAA donors). Of the 8 donors with AMD 6 had the DS/CNV form (50% of AAA donors) and 2 had the GA form (16.7%). (Table 2). Tables 3 and 4 present an analysis of the studies and provide expected and observed occurrences and co-occurrences of AAA and AMD that prove that the two diseases are at a 10-fold greater frequency than would be expected of the total population:

TABLE 2

Summary of Data of
Eye Donors having AAA and/or AMD and/or DS/CNV.

207 Total Donors
33 Donors had AMD =
4 Geographic Atrophy (GA)
11 Disciform scar and choroidal neovascularization (DS/CNV)
18 Other/unknown
12 Donors had AAA:
8 AMD (= 6 DS/CNV and 2 GA)
% of 1998 database w/AMD: 15.9%
% of 1998 database w/DS/CNV: 5.3%
% of 1998 database w/AAA: 5.8%
% of AAA donors w/AMD: 66.7%
% of AAA donors w/DS/CNV: 50%

TABLE 3

Prevalence of AAA and/or AMD

|  | AMD− | AMD+ | Total: |
|---|---|---|---|
| AAA+ | 4 | 8 | 12 |
| AAA− | 170 | 25 | 195 |
| Totals: | 174 | 33 | 207 | a) For donors with clinically diagnosed AMD, what are chances of also having AAA?
AAA in entire repository: 12/207 (5.8%)
AAA in donors w/o AMD: 4/174 (2.3%)
AAA in donors with AMD: 8/33 (24%)

|  | DS/CNV− | DS/CNV+ | Total: |
|---|---|---|---|
| AAA+ | 6 | 6 | 12 |
| AAA− | 190 | 5 | 195 |
| Totals: | 196 | 11 | 207 |

TABLE 3-continued

Prevalence of AAA and/or AMD b) For AMD donors with DS/CNV, what are chances of also having AAA?
AAA in entire repository: 12/207 (5.8%)
AAA in donors w/o DS/CNV: 6/196 (3.1%)
AAA in donors with DS/CNV: 6/11 (54.5%)

TABLE 4

Observed and Expected AMD, CNV/DS and AAA

|      | Obs. AMD+ | Exp. AMD+ | Obs. AMD− | Exp. AMD− |
|------|-----------|-----------|-----------|-----------|
| AAA+ | 8 | 1.91[a] | 4 | 10.09[c] |

|      | Obs. AAA+ | Exp. AAA+ | Obs. AAA− | Exp. AAA− |
|------|-----------|-----------|-----------|-----------|
| AMD+ | 8 | 1.91[a] | 25 | 31.09[d] |

|      | Obs. DS/CNV+ | Exp. DS/CNV+ | Obs. DS/CNV− | Exp. DS/CNV− |
|------|--------------|--------------|--------------|--------------|
| AAA+ | 6 | 0.64[b] | 6 | 11.36[e] |

Wherein: Obs. = Observed; Exp. = Expected;
[a]Exp. AMD+/AAA+ = (% AMD+ in total)(% AAA+ in total)(total donors) = (15.9%)(5.8%)(207) = 1.91
[b]Exp. DS/CNV+/AAA+ = (% CNV+ in total)(% AAA+ in total)(total donors) = (5.3%)(5.8%)(207) = 0.64
[c]Exp. AMD−/AAA+ = total AAA(+) − Exp. AMD+/AAA+ = 12 − 1.91 = 10.09
[d]Exp. AAA−/AMD+ = total AMD(+) − Exp. AAA+/AMD+ = 33 − 1.91 = 31.09
[e]Exp. DS/CNV−/AAA+ = total AAA(+) − Exp. DS/CNV+/AAA+ = 12 − 0.64 = 11.36

Results:

Table 4 demonstrates that the co-occurrence of DS/CNV with AAA is 9.4 fold higher than that expected from the above population of 207 human donors. The co-occurrence of AMD with AAA is 4.2 fold higher than that expected from the above population of 207 human donor eyes. A statistical analysis of the co-occurrence of two variables was determined by the Fisher's exact test (Rossner, B., *Fundamentals of Biostatistics*, Duxbury Press, Belmont, Calif., 370–377, 1995). For Fisher's exact test of co-occurrence of AAA and DS/CNV, $p<0.00001$. This is a statistically significant correlation of the incidence of AMD with that of AAA, suggesting that the diseases share etiology or the same genetic locus.

Example 2

Incidence of AMD in Thoracic Aortic Aneurysm

Of 207 human donors obtained according to Example 1, 8 donor eyes had thoracic aortic aneurysm (TAA), all of which had AMD-associated fundus findings. One TAA donor also had AAA with DS/CNV.

Example 3

Pathologies Associated with AMD

A database is provided describing the medical conditions identified in a database appended hereto as Table 5. A human repository consisting of donor eyes has been collected

| DONOR | AAA | AMD | AO STENOSIS | GLAUCOMA | CAUSE OF DEATH | MEDICAL HISTORY |
|-------|-----|-----|-------------|----------|----------------|-----------------|
| 004-97 |   | X |   |   | pneumonia | CVA, MI, GI bleed, CHF, COPD |
| 19-97 | X |   |   |   | 1-resp. failure 2-COPD | abdominal aneurysm |
| 26-97 |   | X |   |   | 1-cardiac arr. 2-rup. TAA | RF, AVR |
| 31-97 |   | X |   |   | 1-CPA 2-CHD | congenital heart valve defects |
| 34-97 |   | X |   |   | CHF | CHF, COPD |
| 38-97 |   | X |   |   | MSF | HTN, CHF |
| 39-97 |   | X |   |   | 1 R/A 2-COPD | RF, COPD |
| 43-97 |   | X? |   |   | end stage COPD | CHF, pneumonia |
| 60-97 | TAA |   |   |   | ruptured thoracic aneurysm | pre-systemic CA |
| 62-97 |   | X? |   |   | COPD | COPD, mild dementia, aspiratiOn |
| 87-97 | X |   |   |   | ICB | CHF, CAD, HTN, heart disease |
| 96-97 |   | X |   |   | MI | CHF, IDDM, RNF |
| 100-97 | X |   |   |   | MI | CPA |
| 102-97 |   |   |   | X | ICB | TIA's, siezure disorders |
| 109-97 | X |   |   | X | CHF | ? |
| 110-97 | X? |   |   |   | ? | ? |
| 111-97 | X |   |   | X | CVA | HTN, CAD |
| 113-97 | X |   |   |   | probable MI | CPA |
| 125-97 | X |   |   |   | cardiomyopathy, sepsis | CHF, cardiomyopathy, glomerulonephritis |
| 132-97 | X |   |   |   | GI bleed | HTN, GI bleed, bilat hip fx |
| 117-97 | X |   |   |   | CPA | COPD, dementia |
| 136-97 | X |   |   |   | MI | ? |
| 145-97 |   | X? |   |   | cardiac arrest | IDDM, diabetes |
| 150-97 |   | X? |   |   | sepsis, pneumonia | ? |
| 152-97 |   | X? |   |   | pulmonary fibrosis | prostatic HTN, pulm. HTN, interstital pulm. infilltrates |
| 161-97 |   | X? |   |   | MI | CHF, cellulitis in legs |
| 154-97 |   | X F |   |   | CHF, HM | ? |
| 160-97 |   |   |   | X F/D | ICB | HTN, Alzheimer's |
| 162-97 | X |   |   |   | COPD | CHF, COPD, MI |
| 172-97 | X |   |   |   | MI | AAA repair |
| 173-97 |   |   |   | X | ruptured AAA | a-fib, hypothyrodism |
| 174-97 | X | X |   | X | ruptured AAA | CAD, peripherial vascular disease |

-continued

| DONOR | AAA | AMD | AO STENOSIS | GLAUCOMA | CAUSE OF DEATH | MEDICAL HISTORY |
|---|---|---|---|---|---|---|
| 181-97 | | | X | | Promyelocytic leukemia | FABM3, CVA, ARDS, HTN |
| 182-97 | | X F | | | MI | HTN, CHF, TypeII diabetes |
| 189-97 | X? | X | | | CHF, stroke | CHF, CAD, HTN, heart disease | according to the parameters specified in Example 1. Medical and ocular histories, a family questionnaire, and blood and sera, were also obtained from most donors to determine the existence of AAA and AMD. Every eye was subjected to gross examination by a retinal specialist and processed for light (4% paraformaldehyde) and electron (2.0% formaldehyde and 2.5% glutaraldehyde) microscopy, immunohistochemistry, and various biochemical and molecular biological analyses, known in the art. Thus, DNA, RNA, fixed and frozen tissues were available for every eye in the repository. In addition, RPE cell lines were established and frozen from selected donors of all ages and races, with and without AMD. Eyes were analyzed for the presence of AMD by direct examination (disciform scars, submacular neovascular membranes, abnormal pigmentation, and/or geographic atrophy) or by obtaining a clinically documented history of the condition. Other ocular and systemic diseases including glaucoma, diabetes, other retinal and macular degenerations, Alzheimer's disease, Parkinson's disease, and a variety of developmental anomalies are also represented in the repository. The donor eye repository is useful for the study of specific biological processes involved in the etiology of AMD, genotype-phenotype correlations, and "candidate" molecules and genes associated with the etiology of AMD and other macular dystrophies.

Example 4

Monkey Model of AAA

A preferred animal model is an animal with a macula, such a monkey. For example a cynomolgus monkey was anesthetized according to methods well known in the art. The choroidal circulation was blocked and a 360° peritomy was made and traction sutures were used to rotate the eye as far as possible supernasally to gain access to the posterior globe. A blunt cannula was used to separate the choroid from the edge of the sclera and 100 μl of sterile balanced salt solution (BSS) containing 60 units of protease-free chondroitinase ABC (American Cyanimide) was injected into the choroidal stroma. The sclerotomy was closed with 7-0 vicryl sutures. Indirect ophthalmoscopy demonstrated a normal choroid and retina without hemorrhage or depigmentation. The conjunctiva was closed with 7-0 vicryl suture and 3 mg celestone was injected subconjunctivally. The animal was monitored non-invasively with an opthalmoscope to monitor fundus changes, including neovascularization, for 7 days. The animal was then euthanized with barbiturate overdose ("Sleepaway") and the eyes prepared for histological observation according to art known methods. Distinct disruptions of Bruch's membrane were observed in the experimental eye, demonstrating that the enzyme reached Bruch's membrane.

The above example can be modified to inject 1–100 U/ml elastase in 0.05 to 0.50 ml BSS. Alternatively, the method described above can be modified to replace the injection of enzyme for the insertion of enzyme in the form of a slow release pellet, such slow release pellet technology being well known in the art. Alternatively, the aorta may be perfused with elastase or chondroitinase, without the need for surgery, and the animal monitored as above.

Example 5

Rat Model for AAA

An Anidjar/Dobrin rat is created by the infusion of the abdominal aorta with pancreatic elastase. (Anidjar, S., et al., Circulation, 82:973–981, 1990, the teachings of which are incorporated herein by reference and described briefly below). In short, a 1 cm segment of the abdominal aorta of a male Wistar rat is isolated and perfused. The animals are anesthetized with 6% sodium pentobarbital (0.1 ml/100 g body weight) and a PE10 polyethylene catheter is inserted into the femoral artery under a binocular surgical microscope until the tip reaches the infrarenal abdominal aorta. The vena cava is dissected free from the aorta by laparotomy, collateral arteries ligated and the position of the catheter tip verified. The abdominal aorta is clamped at the level of the left renal vein and ligated around the catheter 1 cm downstream. This isolated segment of abdominal aorta is then perfused with 2 ml of the appropriate test solution (rate, 1 ml/hr), such as 15 units pancreatic elastase (Type I; 1 unit=1 mg elastin hydrolysed for 20 minutes at pH8.8, 37° C., Sigma Chemical Co., St. Louis, Mo.) in 2 mls normal saline from the lumen to the adventitia through the media. Control rats are perfused with 2 ml saline alone. At the end of the perfusion, the aorta is unclamped, the ligature and the catheter removed, the femoral artery ligated and the aortic permeability verified. The wounds are closed and the rats are returned to their cages and monitored for the presence of AMD (e.g., drusen, disciform scars or choroidal neovascularization) and for AAA.

Alternatively, the rat may be perfused with other proteases such as collagenase, papain, trypsin, chymotrypsin, chondroitinase, plasmin, plasminogen activator or any other protease that has "elastase activity" (i.e., it can solubilize mature cross-linked elastin) or elastinolytic protease (e.g., macrophage or neutrophil derived proteases). The perfusion of thioglycollate or other inflammatory stimulus would also induce an inflammatory response in the aorta, thereby exacerbating the AAA or AMD effect.

The Anidjar/Dobrin rat may alternatively be infused with elastin degradation products (EDPs) which have been shown to weaken the aorta and to be chemotactic for dendritic cells and macrophages. For example, the peptide Val-Gly-Val-Ala-Pro-Gly (SEQ ID NO:1) can be injected into the aorta and the dilation of the aorta monitored. (Senior, R. M. et al., J. Cell Biol., 99:870–874, 1984). This rat may be used to monitor the effects of agents that inhibit the infiltration of immune cells to damaged aortas (e.g., caused by EDPs), for example, antibodies directed at CD18, a pan-leukocyte antigen, which block the migration of macrophages which contribute to dissection. (Ricci, M. A. et al., J. Vasc. Surg., 23:301–307, 1996).

Example 6

Drusen Associated with Aging and Age-Related Macular Degeneration Contain Proteins Common to Extracellular Deposits Associated with Atherosclerosis, Elastosis Amyloidosis, and Dense Deposit Disease Recent studies in this laboratory revealed that vitronectin is a major component of drusen. Because vitronectin is also a constituent of abnormal deposits associated with a variety of diseases, drusen from human donor eyes were examined for compositional similarities with other extracellular disease deposits. The sixty-three human donor eyes employed in this study were obtained from The University of Iowa Lions Eye Bank (Iowa City, Iowa) within four hours of death; donor ages ranged from 45 to 96 years. Drusen were categorized as hard or soft. Tissues from a minimum of five donors were assayed with each antibody employed, at least two of whom had clinically-documented AMD, and each drusen phenotype was examined in at least two donors. Institutional Review Board committee approval for the use of human donor tissues was obtained from the Human Subjects Committee at The University of Iowa. Thirty-four antibodies to twenty-nine different proteins or protein complexes were tested for immunoreactivity with hard and soft drusen phenotypes. These analyses provide a partial profile of the molecular composition of drusen (see Table A below). Serum amyloid P component, apolipoprotein E, immunoglobulin light chains, Factor X, and complement proteins (C5 and C5b-9 complex) were identified in all drusen phenotypes. Transcripts encoding a number of these molecules were also found to be synthesized by the retina, retinal pigmented epithelium and/or choroid (see Table B below). The compositional similarity between drusen and other disease deposits may be significant in view of the correlation between AMD and arterial wall disruptive disorders, including atherosclerosis (see Table C below). These data suggest that similar pathways may be involved in the etiologies of AMD and other arterial wall disruptive disorders.

TABLE A

Immunoreactivity of Drusen

| Antigen | Supplier | Conc. | No. | Drusen |
|---|---|---|---|---|
| Albumin | Accurate | 1:50 | 5 | − |
| Amyloid A | Dako | 1:50 | 8 | +/−; vesicles |
| Amyloid β | Dako | 1:10 | 7 | − |
| Amyloid Precursor Protein | Boehringer Mannheim | 1:20 | 5 | − |
| Amyloid P component | Dako | 1:50 | 6 | ++ |
|  | Calbiochem | 1:50 | 5 | ++ |
| α1-antichymotrypsin | Dako | 1:50 | 6 | +/− (var.) |
|  | Calbiochem | 1:50 | 5 | +/− (var.) |
| α1 anti-trypsin | ICN | 1:50 | 5 | −, rare +/− |
| Apolipoprotein A1 | Calbiochem | 1:50 | 6 | − |
| Apolipoprotein B | Chemicon | 1:20 | 6 | − |
|  | Dako | 1:50 | 5 | − to +/− |
| Apolipoprotein E | Calbiochem | 1:50 | 9 | + |
| Atrial natriuretic factor | Chemicon | 1:50 | 5 | − |
| C-reactive protein | Dako | 1:50 | 5 | − to +/−, (var.) |
| Calcitonin | Dako | 1:50 | 5 | − |
| Complement C1q | Calbiochem | 1:50 | 5 | − |
| Complement C3 | Dako | 1:50 | 5 | − to +, (var.) |
| Complement C5 | Dako | 1:50 | 5 | ++ |
| Complement C5b-9 | Dako | 1:50 | 5 | ++ |
| Cystatin C | Accurate | 1:50 | 5 | −, (var.) |
| Factor X | Dako | 1:50 | 9 | + |
| Fibrinogen | Dako | 1:50 | 5 | − to +/−, var. |
| Gelsolin | Chemicon | 1:50 | 5 | − |
| HLA-DR | Accurate | 1:25 | 10 | + |
|  | Dako | 1:200 | 10 | + |
| Immunoglobulin kappa | Boehringer Mannheim | 1:50 | 8 | − to +/− |
| Immunoglobulin lambda | Dako | 1:50–1:2000 | 9 | +/− to + |
| β2 microglobulin | Boehringer Mannheim | 1:50 | 5 | − to +/− |
| Prothrombin | Dako | 1:50 | 5 | + (vesicles) |
| Tau | Dako | 1:50 | 5 | − |
| Transthyretin | Boehringer Mannheim | 1:50 | 9 | +/− (var.) |
| Ubiquitin | Chemicon | 1:50 | 5 | − |
|  | StressGen | 1:100 | 5 | −, rare +/− |

Key:
++ = intense, invariant labeling;
+ = strong labeling in most donors;
+/− = weak labeling;
− = no labeling detected;
(var.) = donor to donor or drusen to drusen variation;
vesicles = labeling of spherical profiles within drusen

TABLE B

RT-PCR results from retina, RPE/choroid, and liver.

| Gene Name | Primer Sequence (SEQ ID NOS: 2–25) | Ret | R/Ch | RPE | Gen | Liver |
|---|---|---|---|---|---|---|
| Albumin | SN 5' GTCGAGATGCACACAAGAGTG 3'<br>AS 5' TCCTTCAGTTTACTGGAGATCG 3' | + | + | + | − | + |
| Amyloid P | SN 5' GCCAGGAATATGAACAAGCCG 3'<br>AS 5' CAAATCCCCAATCTCTCCCAC 3' | − | − | − | −* | + |
| Apo B | SN 5' TGAACACCAACTTCTTCCACG 3'<br>AS 5' GGCGACCTCAGTAATTTTCTTG 3' | + | + | − | − | + |
| Apo E | SN 5' GGTCGCTTTTGGGATTACC 3'<br>AS 5' CTCCAGTTCCGATTTGTAGGC 3' | + | + | + | − | + |

TABLE B-continued

RT-PCR results from retina, RPE/choroid, and liver.

| Gene Name | Primer Sequence (SEQ ID NOS: 2–25) | Ret | R/Ch | RPE | Gen | Liver |
|---|---|---|---|---|---|---|
| Complement 3 | SN 5' GTTCAAGTCAGAAAAGGGGC 3'<br>AS 5' GTGTCTTGGTGAAGTGGATCTG 3' | + | + | + | – | + |
| Complement 5 | SN 5' ATGGTATGTGGACGATCAAGGC 3'<br>AS 5' TATTGCTCGGTAACCTTCCCTG 3' | + | + | + | – | + |
| Complement 9 | SN 5' AATGAGCCCCTGGAGTGAATG 3'<br>AS 5' ATGTCAGAGTGTTTCCATCCCG 3' | + | + | – | – | + |
| Factor X | SN 5' GAGCGAGTTCTACATCCTAACG 3'<br>AS 5' CACGAAGTAGGTGTCCTTGAAG 3' | + | + | – | – | + |
| Fibrinogen | SN 5' AGACTGGAACTACAAATGCCC 3'<br>AS 5' AGATTCAGAGTGCCATTGTCC 3' | – | + | – | – | + |
| Ig kappa | SN 5' ACGTTTGATITCCASYTTGGTCCC 3'<br>AS 5' GAMATYSWGIATGACICAGTCTCC 3' | – | + | – | – | + |
| Ig lambda | SN 5' ACCTARACGGTSASCTKGGTCCC 3'<br>AS 5' TCYTMTGWGCTGACTCAGSMCC 3' | + | + | – | – | + |
| Prothrombin | SN 5' GGGCTGGATGAGGACTCAG 3'<br>AS 5' AAGGCAACAGGCTTCTTCAG 3' | – | – | – | – | + |

Ret = retina;
R/Ch = RPE/choroid;
Gen = amplification of genomic DNA by the primer pair;
*= higher molecular weight genomic band detected with primer pair.

TABLE C

Compositional comparison of extracellular disease deposits

| | VN | Amyloid P | Apo E | Complement | Elastin Involved | PGs | Lipids | Calcium |
|---|---|---|---|---|---|---|---|---|
| Drusen | + | + | + | + | ? | – | + | + |
| Elastosis | + | + | ? | + | + | ? | –* | ?† |
| Amyloids | + | + | + | + | + | + | – | + |
| Dense Deposits | + | + | ? | + | ? | + | + | ? |
| Athero plaques | + | + | + | +<br>(C5b-9) | + | | + | + |

*Sudanophilia has been described with actinic elastosis.
†Calcification of elastic fibers occurs in pseudoxanthoma elasticum.

Example 7

Dendritic Cells and Proteins Involved in Immune-Mediated Processes are Associated with Drusen and Play a Central Role in Drusen Biogenesis Drusen are a significant risk factor for the development of age-related macular degeneration (AMD). Relatively little is known, however, about their origin(s). We recently described the presence of centralized domains comprised of distinct saccharides within drusen (J Histochem Cytochem 47;1533–9, 1999). Electron microscopic analyses have revealed that cell processes, derived from choroidal cells, breach Bruch's membrane and terminate in bulbous cores within drusen.

Studies were conducted to immunophenotype the choroidal cells from which these core terminations arise and to evaluate their potential relationship to drusen biogenesis. Human donor eyes employed in this study were obtained from The University of Iowa Lions Eye Bank (Iowa City, Iowa) within four hours of death. Institutional Review Board committee approval for the use of human donor tissues was obtained from the Human Subjects Committee at The University of Iowa. Posterior poles, or wedges of posterior poles spanning between the ora serrata and macula, were processed from 30 donors, embedded in OCT, snap frozen in liquid nitrogen, and stored at –80° C. Tissues were sectioned to a thickness of 6–8 um on a cryostat. Confocal laser scanning microscopy and immunohistochemistry were employed to examine drusen-associated cores in human donor eyes. Immunolabeling of sections was performed using a battery of antibodies directed against various cell populations including endothelial cells, lymphocytes, granulocytes, monocytes/macrophages and dendritic cells.

Anti-CD45 antibodies colocalize with PNA-binding cores in smaller drusen. Drusen cores, and the cells from which they are derived, are strongly reactive with CD45, CD1a, CD83, CD86, and HLA-DR antibodies. Quantitative studies indicate that these drusen-associated cores are present in approximately 40% of drusen. Drusen cores appear to be more prevalent in smaller drusen, and are also detected as putative drusen precursors, solitary cores within Bruch's membrane that are not surrounded by additional drusenoid accretions.

The immunophenotyping data, when combined with ultrastructural analyses, provide strong evidence that drusen cores are derived from choroidal dendritic cells. The identification of dendritic cell-derived cores in smaller drusen and putative drusen precursors, when combined with our previous studies that demonstrate the presence of HLA-DR, immunoglobulin light chains, vitronectin, and terminal complement complexes in all drusen phenotypes, suggest a role for dendritic cells and immune-mediated processes in drusen biogenesis and early AMD.

Example 8

Morphological Characterization of "Choroidal Fibrosis"

Human donor eyes—with and without clinically-documented AMD and/or arterial wall disruptive disorders (AAA, TAA, aortic stenosis, and atheroscleosis) and with distinct drusen morphologies—were employed for simultaneous transmission electron microscopical and immunohistochemical observation. Eyes used in this study were selected from a repository of over 2,000 pairs of human donor eyes (between 0 and 102 years of age) obtained from MidAmerica Transplant Services (St. Louis, Mo.), the Iowa Lions Eye Bank (Iowa City, Iowa), the Heartland Eye Bank (Columbia, Mo.) and the Virginia Eye Bank (Norfolk, Va.) and were processed within four hours of death. The gross pathologic features of all eyes, as well as the corresponding ophthalmic histories, fundus photographs and angiograms, when available, were read by a retina surgeon. Approximately 18% of the donors had some form of clinically diagnosed AMD; these included eyes with macular pigment changes, macular drusen, geographic atrophy, choroidal neovascularization, and/or disciform scars. Eyes with and without clinically documented AMD, were employed in this study.

The RPE-choroid-sclera complex from 151 of these donors were processed for transmission electron microscopical examination. Tissues were fixed in one-half strength Kamovsky's fixative within four hours of death for a minimum of 24 hours, and transferred to 100 mM sodium cacodylate buffer, pH 7.4, prior to dehydration, embedding, sectioning, and photomicrography.

Tissues from the same eyes processed for electron microscopy were processed for light histological (Elastachrome stain; H&E) and immunohistochemical studies. Anti-vitronectin antibody was obtained from Telios (San Diego, Calif.); collagens I, III, V, and VI from Chemicon and Southern Biotech; elastin from Elastin Products; fibrillin-1 from Chemicon; and fibulins 3 and 4 from Rupert Timpl. Selected specimens of human donor RPE-choroid were fixed by immersion in 4% (para)formaldehyde in 0.1M sodium cacodylate buffer and processed for laser scanning confocal microscopy. Images were captured and displayed using a BioRad 1024 laser scanning confocal microscope equipped with a Nikon inverted microscope.

The choroidal stromas of 30 of these individuals are filled with newly synthesized collagen, elastin, elastin-associated microfilaments, and other distinct structural proteins and fibrils as viewed by electron microscopy. Based on preliminary immunohistochemical analyses, the collagen associated with this condition appears to be largely type III and VI and typically exhibits a "spiraled", or "frayed" morphology that is often associated with specific hereditary and acquired diseases. This previously undescribed phenomenon, referred to as "choroidal fibrosis", shares many pathological features that are common in arterial wall disruptive disorders.

TEM Choroidal Fibrosis Database Table 1

| Donor # | age | sex | Cause of death | Past medical history | part of the Ey | Choroidal fibrils Little/medium/lots in chor | in sclera | Need add. EM/Re | AMD, AAA |
|---|---|---|---|---|---|---|---|---|---|
| 84-97 | 6 h | wM | chromosomal anom. | | AM | 1- | | | |
| | | | | | Al-1 | 1 c/e | | EM | |
| | | | | | Al-2 | 1 c/e | | | |
| 124-98 | 21 y | wM | Suicid, GSW-hea | Smoker | BM | 1 c | | EM | |
| | | | | | Bl-2 | 1 c | | | |
| 140-98 | 25 y | cF | Blood clot, pulmonary emboi | Kidney stone, No smoker | AM | 1 c/e | | | |
| | | | | | Al-2 | 1 c | | | |
| 163-98 | 25 y | wM | Suicid, GSW | No smoker | Al-2 | 2 c/e | | | |
| 183-97 | 32 y | wF | Brain tumor | mental. retard. | Al-1 | ? | 2 c/e | EM | |
| | | | | | Bl-1 | ? | | EM | |
| 125-97 | 49 y | wM | Cardiomyopathy | CHF, glomerulonepl | AM | ? | | EM | |
| | | | | | Al-1 | 1 c | | | |
| 64-98 | 44 y | wM | Head trauma, mo vehicle acc. | No smoker. No eye | BM | 1 c | | EM | |
| | | | | | AM | ? | | EM | |
| 152-98 | 48 y | wM | Mal. melanoma w met. | No smoker | BM | 2 c/e | | | |
| | | | | | Bl-2 | 2 c/e | | | |
| 93-98 | 55 y | wM | MI | CAD, CAAG-89, EtC Tabac/cannab smok | BM | ? | | EM | |
| | | | | | Bl-2 | | 1 | EM | |
| 112-98 | 55 y | wM | MI, heart failure | renal insuff. (dialys) Diab w diab. retinopa Smoker | BM | | 1 | | |
| | | | | | Bl-2 | 2–3 c/e | | | |
| 147-98 | 52 y | wM | MI | Cardiomyopathy Smoker | AM | | 0 | EM | |
| | | | | | Al-2 | | 2 | 2 EM | |
| 165-98 | 57 y | wM | AVM | NIDDM, Hpyothyr. | AT-3 | 1 c/e | | | |
| | | | | | Al-2 | 2 c/e | | | |
| | | | | | BT-3 | 1 c/e | | | |
| | | | | | Bl-2 | 2 c/e | 2 c/e | | |
| 204-98 | 58 y | wM | Pulmonary HTN | Lung ca. IDDM, PV PE, COPD, PVT Smoker | AT-3 | 1 c | | EM | |
| | | | | | BT-3 | 1 c/e | | EM | |
| | | | | | Al-1 | 3 c/e | | | |
| #5-98 | 63 y | cF | Uterine ca w met. | HTN, AO valve malfunction | Al-2 | 1 e | 1 c | | |
| | | | | | Bl-1 | 2 c/e | 3 c/e | EM | |
| | | | | | Bl-2 | 1 c | | EM | |
| 94-98 | 65 y | wF | Renal failure | ASHD, PVD, CVA, Former smoker | BM | 1 c/e | | | AMD |
| | | | | | Bl-2 | 1 c/e | | | |

-continued

TEM Choroidal Fibrosis Database Table 1

| Donor # | age | sex | Cause of death | Past medical history | part of the Ey | Choroidal fibrils Little/medium/lots in chor | in sclera | Need add. EM/Re | AMD, AAA |
|---|---|---|---|---|---|---|---|---|---|
| 39-98 | 67 y | cM | MI | CAD, pvd, Diab, st Smoker | AM | 1 e | | EM | |
| | | | | | Al-2 | 2+ c/e | | | |
| 56-98 | 64 y | wM | Intracerebral blee sepsis | EtOH, HTN Former smoker | BM | ? | | EM | |
| | | | | | Bl-2 | 2 c/e | 2 c | | |
| 71-98 | 68 y | wM | Multiple myeloma | COPD, CHF, renal failure. Smoker | BT-3 | 2 c/e | | | |
| 73-98 | 63 y | wM | Intraventricular bleed | HTN, Smoker | AT-3 | 2 c/e | | EM | |
| 42-98 | 72 y | wM | MI | Cardiomyopathy, HT Diab., AMD No smoker | AM | 1 c/e | | EM | AMD/NVM |
| | | | | | Al-2 | 1 c | | EM | |
| 59-98 | 70 y | wM | aspiration pneum | cardiac dysrhytm., atherioscl. Diab, AMD | AM | 1 c | | EM | AMD |
| 61-98 | 76 y | wM | MI | pneumonia, atherios prost. ca., AMD | Bl-1 | 2 c/e | | EM | AMD |
| | | | | | Bl-2 | 2 c/e | | EM | |
| 63-98 | 76 y | wM | gangrenous bowe | No smoker | BM | ? | | EM | AMD |
| | | | | | Bl-1 | ? | | EM | |
| | | | | | Bl-3 | ? | | EM | |
| 90-98 | 77 y | wM | MI | COD, aortic stenosi mitral valve prolaps HTN, AMD, No smoker | BT-3 | 3 c/e | | | AMD |
| | | | | | Al-2 | 3 c/e | | | Aortic stenosis |
| 186-98 | 78 y | wM | MI | MI-90, CAD, CABG vessel surg. Smoke AMD, AAA | BT-3 | 2 c/e | | EM | AMD, AAA |
| | | | | | Bl-2 | 3 c/e | | | |
| 194-98 | 78 y | wM | COPD | IDDM, HTN, chron. renal failure, COPD vessel surg., AMD, AAA No smoker | BM | 2 c/e | | EM | AMD, AAA |
| | | | | | Bl-2 | 3 c/e | | EM | |
| 56-95 | 70 y | wM | not given | HTN, AAA rep., pros ca | Bl-2 | ? | | EM | AAA |
| | | | | | Al-2 | ? | | EM | |
| 172-97 | 78 y | wM | MI | AAA repair | Al-2 | ? c, 3 e | | EM | AAA |
| 52-98 | 77 y | wM | renal failure | IDDM, Fam. hx AM No smoker | BM | ? | | EM | |
| 57-98 | 75 y | wM | cardiac event | COPD, MI x2, HTN Smoker | BM | 2+ c/e | | EM | |
| | | | | | AT-3 | 3 c/e | | EM | |
| 76-98 | 73 y | wM | ICB | Aortic by-pass Former smoker | BT-3 | 3 c/e | | EM | |
| | | | | | Bl-2 | 2 c | 3 c/e | EM | |
| | | | | | Al-2 | 3 c/e | 3 c/e | EM | |
| 159-98 | 71 y | wM | Pontine bleed | Aortic valve replace HTN, AMD, AAA Former smoker | Al-2 | 1 ? | | EM | |
| 20-98 | 76 y | wF | Resp. failure Pneumonia | ASVD, DJD heart arrhytm. lung | Al-2 | 2 c/e | | EM | |
| | | | | | Bl-2 | 2 c/e | | | |
| 47-98 | 78 y | wM | Pneumonia, activ TBC, lung ca | IDDM, MI, prost, ca | | | | | |
| 48-98 | 76 y | wM | Multisystem failur | CAD, rec. pneumon prost. ca Former smoker | Bl-2 | 2 c/e | | | |
| 207-98 | 74 y | wM | AAA | MI, RNF. Smoker | AT-3 | 3 c/e | | | |
| | | | | | Al-2 | 3 c/e | | | |
| 238-98 | 76 y | wF | MI, spinal infarct. | MI, AAA, stroke, spinal iinf. Smoker | BM | 1 c/e | | EM | |
| | | | | | Bl-2 | 3 c/e | | | |
| 34-97 | 83 y | wF | CHF | CHF, COPD | Al-2 | 3 c/e | 3 c/e | | |
| 174-97 | 84 y | wF | Rupt. AAA | AMD, Glaucoma, pe vasc. disease, CAD | AM | 2 c/e | | EM | AMD, AAA |
| | | | | | BT-3 | ? | | EM | Glaucoma |
| | | | | | Bl-2 | ? | | EM | |
| | | | | | Bl-3 | ? | | EM | |
| | | | | | Al-2 | 3 c/e | | EM | |
| | | | | | Al-3 | ? | | EM | |
| 189-97 | 81 y | wF | CHF, stroke | CABG x2, MI, CHF, AMD | AM | 2 c/e | | | AMD |
| | | | | | Bl-1 | 3 c/e | 3 c/e | EM | |
| | | | | | Bl-2 | 3 c/e | | EM | |
| 5598 | 83 y | wM | Lung ca, sepsis | Diab., COPD. Smok | BT-2 | 3 c/e | | EM | AMD |
| 85-98 | 86 y | wM | Congestive heart failure | Stroke, HTN | AM | 2 c/e | | EM | AMD |
| | | | | | Al-1 | 2 c/e | | EM | |
| 60-97 | 87 y | wF | Ruptured TAA | pre-systemic CA | Al-1 | 3 c/e | 3 c/e | | AAA |
| | | | | | Al-2 | 3 c/e | | R | |
| | | | | | Bl-1 | 3 c/e | | R | |
| | | | | | Bl-2 | 3 c/e | 3 c/e | | |
| 117-97 | 81 y | wM | CPA | AAA, Dementia, CO | AM | 3 c/e | | EM | AAA |

-continued

TEM Choroidal Fibrosis Database Table 1

| Donor # | age | sex | Cause of death | Past medical history | part of the Ey | Choroidal fibrils Little/medium/lots in chor | in sclera | Need add. EM/Re | AMD, AAA |
|---|---|---|---|---|---|---|---|---|---|
| #9-98 | 80 y | wF | Sepsis | HTN, pneumonia | BM | 2 c/e | | EM | |
| | | | | | Bl-2 | 2 c/e | 2 c/e | EM | |
| 14-98 | 82 y | wF | MI | not given | Bl-2 | 3 c/e | 3 c/e | | |
| 21-98 | 87 y | wM | Intracerebral blee | No smoker | Bl-2 | 3 c/e | | | |
| 29-98 | 81 y | wM | Multisystem orga failure | No smoker | Bl-2 | ? | | EM | |
| 38-98 | 82 y | wM | MI | Glaucoma, Smoker | Al-2 | ? | | EM | Glaucoma |
| 239-98 | 83 y | wF | CHF | HTN, breast ca, AA TAA, Smoker | BM | ? | | EM | AAA, TAA |
| | | | | | Bl-2 | 3 c/e | | EM | |
| 278-98 | 80 y | wF | Dissect. AA | CVA, MI, Smoker | Bl-2 | 3 c/e | | EM | TAA |
| 100-97 | 92 y | wM | MI | Not given, AMD | BT-3 | 2 c/e | | EM | AMD |
| | | | | | Al | 2 c/e | | EM | |
| 46-98 | 93 y | wF | Septic shock | CVA, CHF, IDDM, breast ca, AMD | Bl-2 | ? | | EM | AMD |
| 51-98 | 93 y | wF | Resp. failure pneumonia | HTN, HOH, CH7 No smoker | AM | 3 c/e | | | |
| | | | | | BM | 3 c/e | | | |
| 58-98 | 94 y | wF | Colon ca | HTN, AMD, POAG | AM | 3 c/e | | EM | AMD, POAG |
| | | | | No smoker | Bl-2 | 2 c/e | 2 c/e | EM | |
| 68-98 | 91 y | wF | CVA/CHF | Aortic stenosis + valv heart disease, HTN, AMD, Glaucoma | BM | 2 c/e | | EM | AMD, Glaucoma |
| 100-98 | 90 y | wF | Intracranial bleed | No smoker | AT-3 | ? | | EM | |
| 107-97 | 101 y | wF | Pneumonia | Not given | BT-3 | 2 c/e | | EM | |
| | | | | | AT-a | 2+ c/e | | EM | |
| | | | | | Bl-1 | ? | | EM | |
| | | | | | Bl-2 | 3 c/e | | EM | |
| | | | | | Al-1 | 3 c/e | | EM | |
| 161-98 | 76 y | wM | Sepsis, CHF | HTN, PVD, CHF, re failure, AMD-GA Former smoker | Bl-2 | 2+ c/e | | | AMD-GA |
| 27-98 | 77 y | wM | Resp. failure, pneumonia | Pulm. fibrosis, HTN TIA, CAD, Aortic by-pass. Former smoker | BM | 3 c/e | | | Pulm fibrosis |
| | | | | | Bl-2 | 3 c/e | | | |
| 152-97 | 57 y | wM | Pulm fibrosis | Pneumonia, NIDDM pulm hypertension AMD | BM | 2 c/e | 2 c/e | | AMD, pulm fibrosis |
| 256-98 | 77 y | wM | Post CABG/CVA | HTN, COPD, pulm bolus x2, prost. ca Aortic dissect. Former smoker | Bl-2 | 3 c/e | 3 c/e | | AAA, dissect |
| | | | | | BM | ? | | EM | |
| 27-98 | 77 | wM | Resp. failure sec. pulmonary fibrosi | Aortic by-pass, HTN TIA, CAD, Smoker | Al-2 | 27 c/3 e | 2 e | | |
| 38-97 | 94 | wF | multisystem failur | AMD, HTN, congest heart failure | Al-2 | 3 c/e | 3 c/2 e | | AMD |
| 24-98 | 81 | wM | MI/CHF | No smoker | Bl-2 | 3 c/2 e | 2 c/e | | |
| 91-98 | 81 | wM | pneumonia, seps lung ca | lobectomy, PVD, C HTN. No smoker | BT3 | ? | ? | EM | |
| 94-98 | 65 | wF | renal failure | AMD, ASHD, PUD, dengen. arthritis Former smoker | BM | ? | ? | EM | |
| | | | | | Bl-2 | 2 c/e | 2 c/e | EM | |
| 114-98 | 76 | wF | CHF | ischemic cardiomyo CAD, smp MI, HTN, CHF renal insuff No smoker | BT3 | ? | ? | EM | |
| 159-98 | 71 | wM | ponline bleed | AAA, AMD?, aortic valve replacement, HTN, CABG Former smoker | Al-2 | ? | | EM | |
| 180-99 | 82 | cM | pneumonia | multisystem organ failure, cardiac history CHF, acute renal failure altherosclerosis of descend, thoracic aorta Former smoker | Bl-2 | ? | | EM | |

TEM Choroidal Fibrosis Database Table 1 -continued

| Donor # | age | sex | Cause of death | Past medical history | part of the Ey | Choroidal fibrils Little/medium/lots in chor | in sclera | Need add. EM/Re | AMD, AAA |
|---|---|---|---|---|---|---|---|---|---|
| 31-99 | 69 | wF | failed AAA | diffuse athereoscler disease + through-out aorta. HTN, coronary-arthery by-pass-90. fam hx for vasc. disease Smoker | BM | ? | | EM | |

TEM Choroid Fibrosis Database Table 2

| Donor # | age | sex | Cause of death | Past medical history | part of the Eye | Choroidal fibrils little/medium/lots in chor. | in sclera | Need add. EM/Rep | AMD, AAA |
|---|---|---|---|---|---|---|---|---|---|
| 1-92 | 71 | wM | cerebellar hema-toma | | BM | 1 | | | |
| | | | | | BTb | 2 | | | |
| 10-92 | 53 | M | MI | | BM | 1 | | | |
| | | | | | ATb | 1 | | | |
| 20-92 | 63 | cM | acut renal failure | | AM | 2 | | | |
| | | | | | ATb | 2 | | | |
| 28-92 | 61 | cF | resp. arrest | lung ca, high dosis of steroids –> leukocytos | AM | 1 | | | |
| | | | | | BTb | 2 | | | |
| 44-92 | 79 | wM | liver ca | | AM | 1 | | | |
| | | | | | ATb | 1 | | | |
| 45-92 | 48 | bM | cardiac-pulm arrest, r/o MT VS PE | | AM | 2 | | | |
| | | | | | ATb | 1 | | | |
| 49-92 | 18 | bM | suicid, GSW to the head | | AM | 1 | | | |
| 58-92 | 17 | wM | head injury due to MVA | | AM | 1 | | | |
| 81-92 | 50 | bF | not given | CPA, schizophrenia | BM | ? | | | |
| 89-92 | 38 | bF | subarachnoidal hemorrhage | | AM | 1 | | | |
| 91-92 | 54 | wM | subarachnoidal hemorrhage | | BM | 2 | | | |
| 93-92 | 62 | wF | cardiac arrest/ congest. heart failure | | AM | 1 | | | |
| 95-92 | 72 | wF | cerebral bleed | | BTb | 2 | | | |
| 96-92 | 71 | wM | met. ca with cardiovasc. occlus and CHF | | AM | 2 | | | |
| 97-92 | 59 | wF | spinal ca | | AM | 2 | | | |
| 98-92 | 22 | wM | head injury | | AM | 1 | | | |
| | | | | | ATb | 1 | | | |
| 99-92 | 69 | wF | resp. failure | lung ca | BM | 1 | | | |
| 100-92 | 36 | wF | lung ca w. met. | Homers syndrome, HT | AM | 2 | | | |
| 101-92 | 58 | wF | cancer | | BM | 2 | | | |
| 102-92 | 65 | wM | cardiac arrest | | AM | 1 | | | |
| 104-92 | 53 | wF | r/o invasive candiasls | | AM | 2 | | | |
| 109-92 | 22 | wM | heat stroke | | BM | 1 | | | |
| 110-92 | 30 | bM | GSW to head | prob. TB or histoplasm | AM | 2 | | | |
| | | | | | ATb | 1 | | | |
| 111-92 | 62 | wM | lung ca | | BM | 2 | | | |
| 113-92 | 42 | wF | brain tumor | | AM | 1 | | | |
| 114-92 | 58 | wM | ischemic cardio-myopathy | | AM | 2 | | | |
| 115-92 | 13 | wM | head injury | | AM | 1 | | | |
| 116-92 | 76 | wF | MI, cardiac arrest | | AM | 1 | | | |
| 117-92 | 69 | bF | prob. MI due to renal metabolic acidosis | renal disease, hemodl MI, atheroscl, heart disease, degen. heart dis. | BM | ? | | | |

-continued

TEM Choroid Fibrosis Database Table 2

| Donor # | age | sex | Cause of death | Past medical history | part of the Eye | Choroidal fibrils little/medium/lots in chor. | Need in sclera | add. EM/Rep | AMD, AAA |
|---|---|---|---|---|---|---|---|---|---|
| 119-92 | 61 | wM | CVA-stroke | CVA (right), left caroti disease, HTN, diab type II | BM | 1 | | | |
| 120-92 | 56 | wM | MI | HTN, coronary artery disease, alcoholic liver disease | AM | 2 | | | |
| 121-92 | 57 | wM | O-26, poles-TB | resp. failure, atypical t CHF, ASHD, COPD, N pulmonary fibrosis | BM BTb | 3+ 2+ | | | pulm fibrosis |
| 123-92 | 47 | wF | multisystem organ failure | | AM | 1 | | | |
| 124-92 | 70 | wF | MI, cardiac-pulm arrest | | BM | 2 | | | |
| 125-92 | 78 | wM | resp failure | | AM | 2 | | | |
| 126-92 | 79 | wM | MI, cardiac arrest | bradycardia, pacemak | AM ATb ATc | ? 3 2 | | | |
| 130-92 | 61 | wM | CPA sec to pulm edema | | AM | 2 | | | |
| 133-92 | 60 | wF | pacemaker failure | sarcoidosis, astma, hyperthyr. | BM BTb | 2 3 | | | |
| 134-92 | 69 | wF | anoxia | CVA, HTN | ATb | 1 | | | |
| 135-92 | 51 | wM | rectal ca w. pul met. | Cushing syndrome, steroid myopathy, diab. | AM | 2 | | | |
| 138-92 | 42 | wM | cardiac-pulm arrest | | BM | ? | | | |
| 139-92 | 27 | bM | GSW to heart | | BM BTb | 2 2 | | | |
| 140-92 | 34 | wF | not given | astma | AM | ? | | | |
| 141-92 | 50 | wM | massive head injury | diab | AM | 2 | | | |
| 142-92 | 15 | wF | head injury sec to MVA | spleenectomy | AM | 2 | | | |
| 143-92 | 82 | wF | resp failure | CHF, COPD, pneumo | BM BTb | 2+ 2 | | | |
| 149-92 | 75 | wM | resp failure, MI | recent MI, atheroscl. heart disease, mild CH chronic A-fib | BM BTb BTd | 1 2 2 | | | |
| 150-92 | 91 | wM | stroke | emphysema, chron re insuff, athereoscleroti heart disease | BM BTb | 2 2 | | | |
| 151-92 | 80 | wM | CHF | | BM | 1+ | | | |
| 152-92 | 81 | wF | CHF | | AM | 2 | | | |
| 153-92 | 18 | wF | cerebral edema | | AM | 1+ | | | |
| 154-92 | 61 | wF | gallbladder ca w met | | BM BTb | 2 2 | | | |
| 155-92 | 75 | wF | COPD | cerebellar degen, pulm embolism, possible A | AM ATb | scar tissue 2 | | | |
| 156-92 | 36 | wM | aneurysm + major head trauma/MVA subdural hematom subarachn hemorr | | AM | 2 | | | |
| 158-92 | 68 | wF | breast ca w me | HTN | AM | 1+ | | | |
| 162-92 | 45 | wM | head injury | | AM | 2 | | | |
| 163-92 | 52 | wF | subarachn hemorrhage | HTN, migraine, CHF, cardiomyopathy breast ca w met | ATa | ? | | | |
| 166-92 | 96 | wF | CHF | | ATb | 2 | | | |
| 168-92 | 60 | wM | full arrest, c/p | lung ca w met | AM | 2 | | | |
| 169-92 | 59 | wF | CHI-intracere- bral hemorrhage | HTN | AM ATb | 2 1 | | | |
| 171-92 | 38 | wM | PE | | AM ATc | ? 1 | | | |
| 175-92 | 55 | bM | colon ca w met | | BM | 2 | | | |
| 176-92 | 66 | wF | endomethrial ca w met | | AM | 2 | | | |
| 179-92 | 37 | wF | PE | livercirrhos sec to EtO portal HTN | AM | 2 | | | |
| 180-92 | 62 | bM | resp arrest larynx ca | | BM | ? | | | |

-continued

TEM Choroid Fibrosis Database Table 2

| Donor # | age | sex | Cause of death | Past medical history | part of the Eye | Choroidal fibrils little/medium/lots in chor. | in sclera | Need add. EM/Rep | AMD, AAA |
|---|---|---|---|---|---|---|---|---|---|
| 181-92 | 85 | wF | ? | TIA | BM | 2 | | | |
| 182-92 | 47 | wM | brain tumor | | AM | 1+ | | | |
| | | | | | ATb | 2 | | | |
| 183-92 | 72 | wM | MI | GI bleed | BM | 1 | | | |
| 185-92 | 96 | wM | pneumonia sec to CHF | | BTa | 3 | | | |
| | | | | | BTb | 3 | | | |
| | | | | | BTc | 2 | | | |
| | | | | | BTd | 2 | | | |
| | | | | | BTe | 2 | | | |
| | | | | | BI | 2 | | | |
| 186-92 | 66 | wF | CVA | | AM | 1+ | | | |
| | | | | | ATb | 1 | | | |
| 187-92 | 79 | wM | anoxia sec to carotid artery occlusion | | AM | 2 | | | |
| | | | | | ATb | 1+ | | | |
| 188-92 | 14 | wM | cardiomyopathy sec to muscular dystrophy | | AM | 1+ | | | |
| 189-92 | 64 | wM | prob. dysrhytm | CVD,, diab | AM | 1+ | | | |
| 192-92 | 86 | wF | cardiac-pulm arrest | | BM | 2 | | | |
| 193-92 | 68 | bF | sepsis | | AM | 2 | | | |
| | | | | | ATb | 2 | | | |
| 194-92 | 78 | wM | cardiac-pulm arrest | cardiomyopathy, CHF, alcoholismus | AM | 1 | | | |
| | | | | | ATb | 1 | | | |
| 195-92 | 75 | wM | cardiac arrest sec to athereos CV disease | athereosclerosis, CV-disease | AM | 1 | | | |
| 198-92 | 82 | wM | caardiac-pulm arrest | | BM | 2 | | | |
| 199-92 | 60 | wM | cancer | | AM | 1 | | | |
| 200-92 | 53 | wM | multisystem failure | HTN, sclerotic cardio-myopathy w CHF | BM | 1 | | | |

Example 9

Gene Expression of Fibrotic Molecules in Choroids of Control, AMD, and Arterial Wall Disruptive Disorders Total RNA was isolated from adult human liver and the RPE/choroid complexes from five control human donors (aged 18 to 58 years), one AMD/AAA donor, one AMD/aortic stenosis donor, and one AMD donor with a family history of AMD. The resulting pellets was stored at −80° C. The quality/integrity of RNA obtained was assessed on both agarose gels and Northern blots. cDNA was synthesized with reverse transcriptase using oligo(dT)16 as a primer. The enzyme was omitted from control reactions.

RT-PCR analyses of RPE-choroid complexes derived from this series of control (non-diseased) and affected (AMD/AAA, AMD, AMD/aortic stenosis) donors reveal distinct patterns of up- and down-regulated gene expression between the two groups (see Table D below). These include "upregulation" of b1 integrin, elastin, collagen VIa2, collagen a3, PI-1 (antitrypsin), PI-2, human metalloelastase (and perhaps fibrillin-2) and "downregulation" of BigH3. No detectable differences in expression levels of collagen IIIa1, collagen Ia2, collagen 6a1, fibulins-1, 2, 3, 4, and 5, HLA-DR, Ig kappa, laminin receptor, or laminin C2 were observed. Because of the limitations of RT-PCR, additional real time quantitative RT-PCR studies are being conducted to assess the precise levels of these genes in the two groups.

Example 10

Autoantibodies Associated with AMD/Arterial Wall Disruptive Diseases

In order to address the role of autoantibodies in AMD and arterial wall disruptive disorder pathogenesis, including drusen biogenesis, we performed a series of preliminary experiments using enriched drusen preparations in order to identify anti-drusen/Bruch's membrane/RPE autoantibodies that might be present in the sera of donors with AMD and AAA.

Protein extracts from an enriched drusen preparation (DR+) obtained by debridement of Bruch's membrane with a #69 Beaver blade and from a control (DR−) preparation were prepared using PBS with proteinase inhibitor cocktail and mild detergent. Proteins were separated by molecular weight using 10–20% gradient mini SDS gels (Amresco) and transferred to PVDF membranes for Western blot analysis. PVDF strips with human retinal proteins from 50 normal human retinas were also used for detection of any anti-retinal autoantibodies in the donor sera.

Sera from the same eight donors described above were screened. Serum from one AMD donor (#90-98) positively labeled a band in the RPE (both DR+ and DR−) and RPE/choroid preparations of approximately 35 kDa. A second band of approximately 60 kDa was labeled

TABLE D

Gene Expression in AMD and Arterial Wall Disruptive Disorders

| Molecule | Expression in Fibrosis vs Controls |
|---|---|
| BIG H3 | Decreased |
| b1-integrin | Increased |
| Collagen 3 a1 | Unchanged |
| Collagen 1 a1 | Unchanged |
| Collagen 1 a2 | Unchanged |
| Collagen 6 a1 | Unchanged |
| Collagen 6 a2 | Increased |
| Collagen 6 a3 | Increased |
| Elastin | Increased |
| Emilin | |
| Fibulin-1 | Unchanged |
| Fibulin-2 | Unchanged |
| Fibulin-3 | Unchanged |
| Fibulin-4 | Unchanged |
| Fibulin-5 | Unchanged |
| FBN-1 | ? |
| FBN-2 | ? |
| Ficolin | ? |
| HLA-DR b | Unchanged |
| HME | Increased |
| IgK | Unchanged |
| Laminin Receptor | Unchanged |
| Lam C1 | ? |
| Lam C2 | Unchanged |
| Lam C3 | ? |
| LO2 | Unchanged |
| LO4 | Unchanged |
| LTBP-1 | ? |
| LTBP-3 | ? |
| LTBP-4 | Decreased |
| MFAP-1 | Decreased |
| MFAP-2 | Decreased |
| MFAP-3 | Unchanged |
| MFAP-4 | Unchanged |
| MMP-2 | Unchanged |
| MMP-7 | ? |
| MMP-9 | ? |
| MMP-12 | Unchanged |
| PI-1 | Decreased |
| PI-2 | Decreased |
| PI-3 | ? |
| PLOD2 | Unchanged |
| PM5 | Unchanged |
| RPE-65 | Unchanged |
| TIMP-1 | Unchanged |
| TIMP-2 | Unchanged |
| TIMP-3 | Unchanged |
| Vitronectin | Increased? | weakly only in the DR+ protein extract. Sera from an AAA donor (#189-97) reacted with a protein(s) of approximately 53 kDa. This band labeled in all three protein extracts. There was one band of approximately 64 kDa that this serum sample labeled only in the DR+sample.

The presence of serum anti-drusen/RPE autoantibodies in donors with AMD/AAA suggests a possible role for shared immune-mediated processes in these disorders.

Example 11

Differential Gene Expression Analyses in AMD and Arterial Wall Disruptive Disorders Differential gene expression of RPE/choroid complexes derived from four paired donors, of selected AMD and AAA phenotypes and age-matched controls has been analyzed using gene array analysis. The arrays utilized in this study contained 18,380 non-redundant cDNAs derived from the I.M.A.G.E. consortium. Each cDNA clone was robotically spotted, in duplicate, onto a nylon membrane in a precise pattern, allowing easy identification. These analyses are typically performed using first strand cDNA which has been radiolabeled during reverse transcription of the probe mRNA. However, due to the small amounts of mRNA that can be isolated from the RPE layer of individual human donor eyes, we have modified this standard protocol. The cDNAs were radiolabeled with 33-P in a random-primed reaction, purified, and hybridized to the gene arrays. The arrays were phosphoimaged, the signals were normalized, and the data analyzed using the Genome Discovery Software package (Genome Systems).

Analysis of the data reveals distinct patterns of clones that are significantly up- and/or down-regulated in the RPE/choroid of individuals with specific AMD and AMD/AAA phenotypes as compared to controls. At this point, these differentially-expressed mRNAs can be grouped into three distinct "pathways": extracellular matrix-, membrane transport-, and gene regulation-associated pathways. In addition, a significant number of uncharacterized expressed sequence tags (ESTs) are differentially expressed in the RPE-choroid of donors with specific AMD and AAA phenotypes as compared to the RPE from donors without the disease.

Database 1

| Field | Pos | Pat | File A Int | File B Int | Score | Ratio | Int. Diff | ClonID | Cluster | GB Acc | Unigene | FL |
|---|---|---|---|---|---|---|---|---|---|---|---|---|
| 1 | k07 | 2 | 1176.28 | 5834.56 | 23105.99 | 4.96 | 4658.29 | 129473 | Cluster | R11336 | Hs. 137763 | |
| 1 | l16 | 8 | 56.97 | 1797.19 | 17400.51 | 9.999 | 1740.22 | 382701 | Cluster | AA069532 | Hs. 5729 | |
| 1 | b20 | 4 | 1822.77 | 6556.43 | 17026.8 | 3.597 | 4733.66 | 52489 | Cluster | H24274 | Hs. 111 | HT2447 |
| 1 | j21 | 1 | 212.69 | 2005.38 | 16902.68 | 9.429 | 1792.69 | 24032 | Cluster | T78285 | Hs. 90863 | |
| 6 | j16 | 4 | 163.58 | 1598.01 | 14013.13 | 9.769 | 1434.43 | 209303 | Cluster | H63368 | Hs. 114004 | |
| 4 | o20 | 5 | 157.71 | 1546.53 | 13619.05 | 9.806 | 1388.83 | 245873 | Cluster | N72922 | Hs. 22341 | |
| 3 | e23 | 7 | 302.16 | 2050.34 | 11862.4 | 6.786 | 1748.18 | 60874 | Cluster | T39572 | Hs. 760 | HT125 |
| 4 | k14 | 3 | 103.78 | 1272.09 | 11681.88 | 9.999 | 1168.3 | 154571 | Cluster | R54764 | Hs. 26204 | |
| 6 | k09 | 4 | 175.41 | 1488.99 | 11150.73 | 8.489 | 1313.58 | 204705 | Cluster | H57226 | Hs. 75641 | HT1045 |
| 2 | d21 | 5 | 854.08 | 3399.24 | 10129.68 | 3.98 | 2545.15 | 230370 | Cluster | H75530 | Hs. 16 | HT1675 |
| 2 | h01 | 7 | 502.82 | 2403.48 | 9085.11 | 4.78 | 1900.66 | 325821 | Cluster | AA037110 | Hs. 75970 | |
| 2 | c10 | 5 | 1363.71 | 4238.44 | 8934.73 | 3.108 | 2874.73 | 223293 | Cluster | H86270 | Hs. 75219 | HT1234 |
| 4 | a17 | 7 | 1222 | 3963.27 | 8890.6 | 3.243 | 2741.26 | 346854 | Cluster | W78125 | Hs. 47584 | |
| 6 | j12 | 4 | 667.51 | 2740.32 | 8509.41 | 4.105 | 2072.8 | 209281 | Cluster | H65578 | Hs. 114188 | |
| 1 | k05 | 5 | 384.91 | 1928.92 | 7737.58 | 5.011 | 1544.01 | 211857 | Cluster | H68430 | Hs. 109450 | |
| 1 | j03 | 6 | 691.74 | 2668.3 | 7624.31 | 3.857 | 1976.56 | 271256 | Cluster | N44562 | Hs. 44613 | |

-continued

Database 1

| | | | | | | | | | | | | |
|---|---|---|---|---|---|---|---|---|---|---|---|---|
| 5 | f23 | 5 | 82.28 | 812.89 | 7217.65 | 9.879 | 730.61 | 255777 | Cluster | N27758 | Hs. 43993 | |
| 6 | j08 | 4 | 673.92 | 2548.31 | 7087.75 | 3.781 | 1874.4 | 209276 | Cluster | H63352 | Hs. 38194 | |
| 1 | j18 | 2 | 791.1 | 2789.36 | 7045.66 | 3.526 | 1998.25 | 27689 | Cluster | R13106 | Hs. 139029 | |
| 5 | m19 | 4 | 645.56 | 2436.57 | 6759.91 | 3.774 | 1791.01 | 198896 | Cluster | H83192 | Hs. 62402 | |
| 6 | i21 | 5 | 466.27 | 2015.03 | 6693.1 | 4.322 | 1548.76 | 260214 | Cluster | N45406 | Hs. 141460 | |
| 2 | e16 | 5 | 591.78 | 2252.83 | 6323.28 | 3.807 | 1661.04 | 223625 | Cluster | H86968 | | |
| 2 | c01 | 6 | 435.12 | 1888.04 | 6304.44 | 4.339 | 1452.92 | 273917 | Cluster | N46505 | | |
| 1 | i17 | 1 | 2724.39 | 5641.93 | 6041.94 | 2.071 | 2917.54 | 22140 | Cluster | T64807 | | HT2245 |
| 1 | i12 | 3 | 16064 | 1061.74 | 5955.53 | 6.609 | 901.09 | 69940 | Cluster | T48696 | Hs. 100132 | |
| 1 | i02 | 5 | 963.71 | 2920.39 | 5929.48 | 3.03 | 1956.68 | 213484 | Cluster | H71668 | Hs. 110286 | |
| 2 | g11 | 5 | 1565.45 | 3881.45 | 5742.45 | 2.479 | 2316.01 | 222246 | Cluster | H86008 | | |
| 6 | j06 | 2 | 1004.89 | 2937.73 | 5650.48 | 2.923 | 1932.83 | 135085 | Cluster | R33918 | Hs. 72824 | |
| 3 | p20 | 2 | 312.73 | 1485.66 | 5572.18 | 4.751 | 1172.93 | 36189 | Cluster | R21373 | Hs. 76335 | |
| 5 | n16 | 4 | 787.46 | 2520.84 | 5548.92 | 3.201 | 1733.38 | 203557 | Cluster | H56112 | | |
| 4 | b05 | 1 | 883.66 | 2597.03 | 5035.47 | 2.939 | 1713.37 | 118792 | Cluster | T92527 | Hs. 111916 | |
| 1 | d19 | 8 | 1077.33 | 2922.77 | 5006.66 | 2.713 | 1845.45 | 380535 | Cluster | AA053898 | Hs. 114818 | |
| 1 | i06 | 3 | 502.37 | 1851.41 | 4971.72 | 3.685 | 1349.05 | 137710 | Cluster | R37989 | | |
| 6 | f08 | 6 | 754.48 | 2326.29 | 4846.36 | 3.083 | 1571.81 | 306146 | Cluster | W20101 | | |
| 4 | a15 | 7 | 1283.96 | 3206.94 | 4803.01 | 2.498 | 1922.98 | 344774 | Cluster | W74705 | Hs. 1550 | HT3851 |
| 1 | e24 | 1 | 378.8 | 1543.61 | 4746.59 | 4.075 | 1164.81 | 22897 | Cluster | T75253 | Hs. 12333 | |
| 6 | n09 | 4 | 1369.32 | 3321.23 | 4734.26 | 2.425 | 1951.9 | 208059 | Cluster | H62639 | Hs. 103424 | |
| 6 | j24 | 6 | 1311.86 | 3223.23 | 4696.21 | 2.457 | 1911.37 | 306759 | Cluster | W23986 | Hs. 31880 | |
| 6 | i17 | 4 | 577.51 | 1955.77 | 4667.48 | 3.387 | 1378.25 | 204656 | Cluster | H57192 | Hs. 141602 | |
| 1 | j11 | 8 | 182.5 | 1011.75 | 4597.17 | 5.544 | 829.25 | 380978 | Cluster | AA057398 | | |
| 6 | j12 | 2 | 325.65 | 1394.27 | 4575.27 | 4.281 | 1068.62 | 135107 | Cluster | R33933 | Hs. 106200 | |
| 2 | d22 | 4 | 1090.95 | 2826.91 | 4498.36 | 2.591 | 1735.97 | 176889 | Cluster | H45241 | Hs. 108124 | |
| 2 | c01 | 5 | 492.25 | 1751 | 4477.6 | 3.557 | 1258.75 | 222032 | Cluster | H85307 | Hs. 78150 | HT3629 |
| 1 | j17 | 8 | 182.25 | 991.11 | 4398.7 | 5.438 | 808.86 | 380987 | Cluster | AA057468 | | |
| 6 | k20 | 5 | 215.73 | 1044.01 | 4008.33 | 4.839 | 828.28 | 263914 | Cluster | N28535 | Hs. 75428 | HT3218 |
| 1 | j15 | 8 | 477.77 | 1632.59 | 3946.08 | 3.417 | 1154.81 | 380986 | Cluster | AA057467 | Hs. 47068 | |
| 1 | c23 | 6 | 432.87 | 1530.32 | 3879.81 | 3.555 | 1097.45 | 267778 | Cluster | N34196 | | |
| 5 | h08 | 7 | 1148.27 | 2754.46 | 3852.93 | 2.399 | 1606.19 | 562186 | Cluster | AA211593 | Hs. 92129 | HT3659 |
| 1 | h24 | 8 | 787.53 | 2147.49 | 3708.42 | 2.727 | 1359.96 | 382457 | Cluster | AA069746 | Hs. 84244 | HT383 |
| 6 | i15 | 2 | 373.91 | 1371.78 | 3660.87 | 3.669 | 997.87 | 130980 | Cluster | R23027 | Hs. 138216 | |
| 6 | h13 | 2 | 395.69 | 1415.11 | 3645.8 | 3.576 | 1019.42 | 133702 | Cluster | R28577 | | |
| 2 | c01 | 2 | 230.66 | 1035.87 | 3615.96 | 4.491 | 805.2 | 28229 | Cluster | R13333 | Hs. 21305 | |
| 6 | h22 | 6 | 535.45 | 1665.93 | 3517.31 | 3.111 | 1130.49 | 306412 | Cluster | W20275 | | |
| 6 | g10 | 2 | 1079.98 | 2551.97 | 3478.28 | 2.363 | 1471.99 | 132237 | Cluster | R25219 | Hs. 23817 | |
| 3 | g14 | 7 | 654.63 | 1843.77 | 3349.17 | 2.816 | 1289.14 | 85533 | Cluster | T72189 | | HT1289 |
| 3 | o20 | 1 | 3273.06 | 5327.27 | 3343.46 | 1.628 | 2054.21 | 114073 | Cluster | T79540 | Hs. 111782 | |
| 2 | e13 | 2 | 599.62 | 1742.2 | 3318.07 | 2.905 | 1142.38 | 28466 | Cluster | R13379 | Hs. 64135 | |
| 1 | b24 | 3 | 136.08 | 741.53 | 3299.14 | 5.449 | 605.45 | 139990 | Cluster | R64675 | Hs. 24167 | |
| 5 | p23 | 6 | 331.56 | 1218.26 | 3258.05 | 3.674 | 886.7 | 297963 | Cluster | N98325 | Hs. 137909 | |
| 4 | g18 | 2 | 1254.85 | 2725.78 | 3195.13 | 2.172 | 1470.93 | 37482 | Cluster | R33062 | | |
| 1 | k23 | 4 | 188.47 | 875.74 | 3193.53 | 4.647 | 687.28 | 50141 | Cluster | H17788 | Hs. 31066 | |
| 4 | k23 | 2 | 371.59 | 1288.77 | 3181 | 3.468 | 917.18 | 37109 | Cluster | R34443 | | |
| 2 | j13 | 4 | 863.3 | 2132.08 | 3134.63 | 2.47 | 1269.07 | 174664 | Cluster | H40649 | | |
| 6 | d22 | 1 | 977.26 | 2299.56 | 3111.47 | 2.353 | 1322.3 | 128161 | Cluster | R09793 | Hs. 27931 | |
| 2 | l07 | 5 | 583.06 | 1667.72 | 3102.44 | 2.86 | 1084.66 | 230996 | Cluster | R96161 | Hs. 138512 | |
| 3 | m23 | 4 | 835.38 | 2074.03 | 3075.28 | 2.483 | 1238.66 | 179905 | Cluster | H50920 | | |
| 1 | j10 | 4 | 539.16 | 1583.6 | 3067.65 | 2.937 | 1044.43 | 52618 | Cluster | H29394 | | |
| 6 | f11 | 5 | 739.02 | 1916.38 | 3053.03 | 2.593 | 1177.36 | 264848 | Cluster | N29101 | Hs. 75503 | HT3684 |
| 2 | i20 | 4 | 184.88 | 848.95 | 3049.52 | 4.592 | 664.08 | 172473 | Cluster | H20257 | | |
| 6 | o02 | 2 | 1234.95 | 2637.47 | 2995.38 | 2.136 | 1402.53 | 133002 | Cluster | R24476 | | |
| 1 | i05 | 1 | 752.32 | 1920.24 | 2981.04 | 2.552 | 1167.92 | 21917 | Cluster | T66051 | | |
| 2 | e12 | 3 | 419.6 | 1345.01 | 2966.42 | 3.205 | 925.42 | 142882 | Cluster | R71543 | Hs. 141964 | |
| 1 | j01 | 6 | 731.53 | 1882 | 2959.8 | 2.573 | 1150.47 | 271252 | Cluster | N34571 | Hs. 41663 | |
| 6 | g10 | 5 | 496.23 | 1483.88 | 2953.47 | 2.99 | 987.66 | 262754 | Cluster | N28295 | Hs. 141435 | |
| 2 | h01 | 1 | 117.94 | 651.36 | 2946.02 | 5.523 | 533.42 | 110759 | Cluster | T83266 | Hs. 100090 | |
| 4 | k20 | 7 | 94.4 | 574.28 | 2919.33 | 6.083 | 479.88 | 530260 | Cluster | AA111987 | | |
| 5 | k02 | 1 | 1426.28 | 2874.44 | 2918.56 | 2.015 | 1448.17 | — | Cluster | #NAME? | | |
| 2 | l05 | 1 | 365.5 | 1230.09 | 2909.82 | 3.366 | 864.59 | 110893 | Cluster | T82879 | Hs. 13756 | |
| 1 | j05 | 8 | 151.81 | 744.28 | 2904.96 | 4.903 | 592.48 | 380914 | Cluster | AA057495 | Hs. 76224 | HT3350 |
| 1 | i14 | 6 | 465.37 | 1417.51 | 2900.22 | 3.046 | 952.14 | 270035 | Cluster | N40606 | Hs. 141444 | |
| 6 | k05 | 1 | 467.94 | 1417.75 | 2877.74 | 3.03 | 949.81 | 125636 | Cluster | R07461 | | |
| 5 | a02 | 6 | 1029.9 | 2307.86 | 2863.74 | 2.241 | 1277.96 | 295400 | Cluster | W04464 | Hs. 138522 | |
| 6 | h10 | 4 | 482.43 | 1435.72 | 2837.01 | 2.976 | 953.29 | 209204 | Cluster | H62020 | | |
| 6 | k16 | 6 | 336.18 | 1159.02 | 2836.78 | 3.448 | 822.84 | 302070 | Cluster | W17034 | Hs. 363 | |
| 2 | i11 | 5 | 1752.63 | 3263.61 | 2813.62 | 1.862 | 1510.98 | 22409 | Cluster | H86161 | Hs. 141367 | |
| 6 | n03 | 7 | 2336.16 | 3983.14 | 2808.07 | 1.705 | 1646.97 | 626746 | Cluster | AA216447 | Hs. 89608 | HT115 |
| 1 | k03 | 2 | 422.22 | 1316.61 | 2789.02 | 3.118 | 894.39 | 129413 | Cluster | R11257 | | |
| 2 | i09 | 2 | 1458.79 | 2867.56 | 2769.22 | 1.966 | 1408.89 | 28657 | Cluster | R14286 | | |
| 1 | i14 | 3 | 387.9 | 1244.45 | 2747.85 | 3.208 | 856.54 | 137744 | Cluster | R68503 | Hs. 1382321 | |
| 6 | h21 | 3 | 549.28 | 1532.33 | 2742.42 | 2.79 | 983.05 | 47817 | Cluster | H11685 | | |
| 1 | i03 | 4 | 364.21 | 1192.63 | 2712.67 | 3.275 | 828.42 | 49961 | Cluster | H29383 | | |
| 4 | k23 | 3 | 242.97 | 934.16 | 2657.46 | 3.845 | 691.19 | 153354 | Cluster | R47887 | Hs. 71388 | |
| 4 | d17 | 1 | 398.91 | 1246.35 | 2647.64 | 3.124 | 847.43 | 119302 | Cluster | T98238 | | |

-continued

Database 1

| 1 | e19 | 5 | 561.86  | 1532.3  | 2646.57 | 2.727 | 970.44  | 211202 | Cluster | H67987   | Hs. 38654  | HT889 |
|---|-----|---|---------|---------|---------|-------|---------|--------|---------|----------|------------|-------|
| 1 | j06 | 5 | 448.71  | 1335.34 | 2638.51 | 2.976 | 886.62  | 220470 | Cluster | H87319   | Hs. 1432   |       |
| 6 | c19 | 5 | 1624.7  | 3030.57 | 2622.38 | 1.865 | 1405.87 | 259279 | Cluster | N41802   |            |       |
| 1 | j23 | 8 | 537.38  | 1484.57 | 2616.8  | 2.763 | 947.2   | 381024 | Cluster | AA054639 | Hs. 36658  |       |
| 2 | h04 | 4 | 1134.32 | 2370.98 | 2584.88 | 2.09  | 1236.65 | 177300 | Cluster | H40720   | Hs. 31775  |       |
| 4 | l09 | 7 | 286.02  | 1013.81 | 2579.66 | 3.545 | 727.79  | 511972 | Cluster | AA102358 |            |       |
| 1 | a12 | 4 | 778.27  | 1845.08 | 2529.15 | 2.371 | 1066.81 | 20075  | Cluster | H17348   | Hs. 117688 |       |

Field Identity

| | |
|---|---|
| 1 | Soares fetal liver spleen 1NFLS (ESTs) |
| 1 | Soares pineal gland N3HPG (ESTs) |
| 1 | Soares infant brain 1NIB/similar to glia-activating precursor (fibroblast growth factor 9) |
| 1 | Soares infant brain 1NIB/human death domain containing protein CRADD mRNA |
| 6 | Soares fetal liver spleen 1NFLS/highly similar to heat shock cognate 71 kd protein-human protein mRNA |
| 4 | Soares fetal liver spleen 1NFLS/similar to carboxypeptidase M precursor (*Homo sapien* LIM protein mRNA-pinch protein) |
| 3 | Stratagene placenta #937225/similar to transcriptin factor GATA-2 (GATA-binding protein 2) |
| 4 | Soares breast 2NbHBst (ESTs) |
| 6 | Soares fetal liver spleen 1NFLS/similar to galactose-1-phosphate uridyl transferase |
| 2 | Soares fetal liver spleen 1NFLS (V-crk avian sarcoma virus CT10 oncogene homolog) |
| 2 | Soares senescent fibroblast NbHSF/similar to contains Alu repetitive element (*Homo sapien* mRNA for KIAA0632 protein, partial cds) |
| 2 | Soares retina N2b5HR/similar to tyrosinase-related protein 1 precursor (5,6-diihydoxyindole-2-carboxylic acid oxidase precursor) |
| 4 | Soares fetal heart NbHH19W (*Homo sapien* Shab-related delayed-rectifier K+ channel alpha subunit mRNA, complete cds) |
| 6 | Soares fetal liver spleen 1NFLS (ESTs) |
| 1 | Soares fetal liver spleen 1NFLS (human Rho-assoc., coiled-coil containing protein kinase p16ROCK mRNA, complete cds) |
| 1 | Soares melanocyte 2NbHM (highly similar to *Homo sapien* ATP receptor) |
| 5 | *Homo sapien* cDNA clone 255777/similar to contains Alu repetitive element (ESTs) |
| 6 | Soares fetal liver spleen 1NFLS/similar t contains MEr 6 repetitive element (ESTs) |
| 1 | Soares infant brain 1NIB (ESTs) |
| 5 | Soares fetal liver spleen 1NFLS/similar to serine/threonine-protein kinase pak (*Homo sapien* p21 activated kinase PAK 1B mRNA) |
| 6 | Soares placenta 8–9 weeks 2NbHP8to0W (ESTs) |
| 2 | Soares retina N2b5HR |
| 2 | Soares melanocyte 2NbHM |
| 1 | Soares infant brain 1NIB/similar to myosin heavy chain, nonmuscle type B-human |
| 1 | Stratagene placenta #937225 (ESTs) |
| 1 | Soares fetal liver spleen 1NFLS (ESTs) |
| 2 | Soares retina N2b5HR |
| 6 | Soares placenta Nb2HP (*Homo sapien* mRNA for sigma 3B protein) |
| 3 | Soares infant brain 1NIB (human 54 kDa protein mRNA, complete cds-PTB-assoc. splicing factor) |
| 5 | Soares fetal liver spleen 1NFLS |
| 4 | Stratagene lung #937210 (ESTs) |
| 1 | Soares retina N2b4HR (ESTs) |
| 1 | Soares placenta Nb2HP |
| 6 | Soares parathyroid tumor NbHPA/similar to methionyl-tRNA formyltransferase |
| 4 | Soares fetal heart NbHH19W/similar to proteasome component C13-human (proteasome component C13 precursor) |
| 1 | Soares infant brain 1NIB (ESTs) |
| 6 | Soares fetal liver spleen 1NFLS/similar to heat shock cognate 71 KD protein-human |
| 6 | Soares fetal lung NbHL19W (ESTs, weakly similar to CMP-N-Acetyneuraminate-Beta-1,4-Galactosi alpha-2,3-sialyltransferase) |
| 6 | Soares fetal liver spleen 1NFLS/similar to contains Alu repetitive element, contains MIR repetitive element (ESTs) |
| 1 | Soares retina N2b4HR/similar to contains DBR repetitive element |
| 6 | Soares placenta Nb2HP/similar to contains Alu repetitive element (ESTs) |
| 2 | Soares adult brain N2b5HB55Y (60S ribosomal protein L41) |
| 2 | Soares retina N2b5HR (human K-ras oncogene protein mRNA, complete cds-transorming protein P21/H-RAS-1) |
| 1 | Soares retina N2b4HR |
| 6 | Soares melanocyte 2NbHM/similar to superoxide dismulase-human (superoxide dismutase 1-Cu/Zn) |
| 2 | Soares retina N2b4HR/similar to contains Alu repetitive element (ESTs) |
| 1 | Soares melanocyte 2NbHM/similar to contains Alu repetitive element |
| 5 | Stratagene muscle #937209 (carbonic anhydrase III-human) |
| 1 | Soares pineal gland N3HPG (*Homo sapien* potassium channel Kv2.1 mRNA, complete cds) |
| 6 | Soares placenta Nb2HP (ESTs) |
| 6 | Soares placenta Nb2HP |
| 2 | Soares infant brain 1NIB/similar to contains Alu repetitive element, contains TAR 1 repetitive element (ESTs) |
| 6 | Soares fetal lunch NbHL19W/similar to mouse brain protein H5 |
| 6 | Soares placenta Nb2HP (ESTs) |
| 3 | Stratagene liver #937224/similar to liver carboxyesterase precursor-human |
| 3 | Soares fetal liver spleen 1NFLS/similar to contains Alu repetitive element, contains MER22 repetitive element (ESTs-highly similar to myc-assoc. zinc finger protein-human) |
| 2 | Soares infant brain 1NIB (ESTs, weakly similar to Alu subfamily J-human) |
| 1 | Soares placenta Nb2HP (*Homo sapien* mRNA for novel gene in Xq28 region-synaptobrevin-related protein) |
| 5 | Soares fetal lung NbHL19W/similar to tumor necrosis factor receptor 2 precursor-human, contains Alu repetitive element (ESTs) |
| 4 | Soares infant brain 1NIB |
| 1 | Soares infant brain 1NIB (ESTs) |
| 4 | Soares infant brain 1NIB |
| 2 | Soares adult brain N2b5HB55Y |
| 6 | Soares fetal liver spleen 1NFLS (ESTs) |
| 2 | Soares pineal gland N3HPG/similar to contains Alu repetitive element (ESTs) |
| 3 | Soares adult brain N2b3HB55Y |

-continued

Database 1

| | |
|---|---|
| 1 | Soares infant brain 1NIB |
| 6 | Soares melanocyte 2NbHM (*Homo sapien* TFE3 gene, exons 1,2,3-and joined cds/transcription factor E3-human) |
| 2 | Soares adult brain N2b5HB55Y |
| 6 | Soares plancenta Nb2HP |
| 1 | Soares infant brain 1NIB |
| 2 | Soares placenta Nb2HP/similar to contains Alu repetitive element (ESTs) |
| 1 | Soares melanocyte 2NbHM/similar to human carcinoma cell-derived Alu RNA transcript (rRNA), activator 1 40 KD subunit-human (ESTs) |
| 6 | Soares melanocyte 2NbHM/similar to contains Alu repetitive element (ESTs) |
| 2 | Soares fetal liver spleen 1NFLS (human globin gene) |
| 4 | Stratagene fibroblast #937212/similar to 60S acidic ribosomsal protein P1-human |
| 5 | |
| 2 | Soare fetal liver spleen 1NFLS (ESTs) |
| 1 | Soares retina N2b4HR (human extracellular protein [S1-5] mRNA, complete cds-fibulin-1, isoform V precursor-human) |
| 1 | Soares melanocyte 2NbHM (ESTs) |
| 6 | Soares fetal liver spleen 1NFLS/similar to heterogeneous nuclear ribonucleoprotein A1-human |
| 5 | Soares fetal liver spleen 1NFLS/similar to contains Alu repetitive element (ESTs) |
| 6 | Soares fetal liver spleen 1NFLS/similar to contains Alu repetitive element |
| 6 | Soares fetal lung NbHL19W (zinc finger protein 139-clone pHZ-37) |
| 2 | Soares retina N2b5HR (ESTs) |
| 6 | Stratagene HeLa cell s3 #937216/similar to protein phosphatase PP2A, 65 KD regulatory subunit, beta-human (protein phosphatase 2, regulatory subunit A [PR65], beta isoform) |
| 1 | Soares fetal liver spleen 1NFLS |
| 2 | Soares infant brain 1NIB |
| 1 | Soares placenta Nb2HP/similar to contains Alu repetitive element (ESTs) |
| 6 | Soares infant brain 1NIB |
| 1 | Soares infant brain 1NIB |
| 4 | Soares breast 2NbHBst/similar to bovin cathepsin (*Homo sapien* cathepsin Z precursoe [CTsZ] mRNA, complete cds) |
| 4 | *not found on GB |
| 1 | Soares fetal liver spleen 1NFLS/similar to contains Alu repetitive element, contains PTR5 repetitive element (ESTs, highly similar to ribosomal protein S6 kinase II alpha 2-*Mus musculus*) |
| 1 | Soares retina N2b4HR/similar to contains Alu repetitive element (protein kinase C substrate 80K-H) |
| 6 | Soares placenta 8–9 weeks 2NbHP8to9W/similar to human carcinoma cell-derived Alu RNA transcript, cytochrome P450 IA2-human |
| 1 | Soares retina N2b4HR/similar to contains Alu repetitive element (ESTs) |
| 2 | Soares adult brain N2b5HB55Y/similar to contains L1 repetitive element (ESTs) |
| 4 | Stratagene colon #937204 |
| 1 | Soares infant brain 1NIB/similar to contains Alu repetitive element (ESTs, highly similar to Alu subfamily SB2-human) |

| | | | File A Intensity | File B Intensity | Score | Ratio | Int Diff | ClonID | Genbank Acc# | FL | Protein Name |
|---|---|---|---|---|---|---|---|---|---|---|---|
| 3 | a19 | 7 | 9184.94 | 1506.99 | 46796.341 | 6.095 | 7677.96 | 73163 | T56622 | HT1291 | TRANSTHYRETIN PRECURSOR |
| 3 | i16 | 7 | 6765.23 | 858.77 | 46529.972 | 7.878 | 5906.46 | 77938 | T53808 | HT4362 | BIOTINIDASE |
| 3 | h17 | 8 | 4427.8 | 457.73 | 38404.236 | 9.673 | 3970.07 | 429711 | AA011711 | NA | TRANSTHYRETIN PRECURSOR |
| 4 | l23 | 4 | 13634 | 4261.84 | 29982.467 | 3.199 | 9372.17 | 195352 | R89536 | NA | TRANSTHYRETIN PRECURSOR |
| 3 | a17 | 7 | 8575.48 | 1960.49 | 28934.93 | 4.374 | 6614.99 | 67221 | T52674 | HT1501 | VASCULAR ENDOTHELIAL GROWTH FACTOR RECEPTOR 1 |
| 3 | a07 | 7 | 3329.61 | 360.95 | 27384.499 | 9.225 | 2968.66 | 60267 | T40473 | HT3094 | HYPOTHETICAL PROTEIN 458 |
| 3 | a20 | 7 | 2863.76 | 159.94 | 27035.506 | 9.999 | 2703.82 | 78438 | T61381 | HT4199 | None |
| 3 | g14 | 3 | 1366.74 | 113.46 | 12531.495 | 9.999 | 1253.27 | 148991 | R82287 | NA | None |
| 3 | h24 | 5 | 2251.24 | 397.39 | 10502.04 | 5.665 | 1853.85 | 241622 | H98923 | NA | None |
| 2 | h15 | 3 | 1926.8 | 315.85 | 9827.459 | 6.1 | 1610.95 | 144221 | R76995 | HT3952 | HEMOGLOBIN BETA CHAIN |
| 1 | e09 | 5 | 2850.47 | 670.44 | 9268.68 | 4.252 | 2180.03 | 211024 | H65775 | NA | None |
| 3 | k24 | 7 | 1125.37 | 135.09 | 8249.176 | 8.33 | 990.27 | 321075 | W56898 | NA | None |
| 6 | i18 | 8 | 1436.78 | 239.81 | 7171.337 | 5.991 | 1196.97 | 503812 | AA13170 | NA | APOLIPOPROTEIN D PRECURSOR |
| 3 | o19 | 3 | 1797.96 | 387.38 | 6546.89 | 4.641 | 1410.58 | 148425 | H12367 | HT1428 | HEMOGLOBIN BETA CHAIN |
| 2 | p14 | 4 | 694.63 | 68.66 | 6259.164 | 9.999 | 625.98 | 178599 | H49130 | NA | None |
| 3 | d16 | 1 | 1219.74 | 211.03 | 5830.262 | 5.78 | 1008.71 | 114926 | T86234 | NA | None |
| 5 | e12 | 8 | 1551.17 | 327.42 | 5797.674 | 4.738 | 1223.75 | 489404 | AA045613 | NA | DHII_HUMAN P28845 CORTICOSTEROID 11-BETA-DEHYDROGENASE |
| 3 | d12 | 1 | 605.36 | 26.64 | 5786.524 | 9.999 | 578.71 | 114906 | T86313 | NA | AMINE OXIDASE |
| 5 | h22 | 7 | 893.55 | 127.18 | 5384.899 | 7.026 | 766.38 | 562243 | AA211746 | HT364 | TROPONIN I, SLOW SKELETAL MUSCLE |
| 1 | h24 | 8 | 656.07 | 91.17 | 4065.086 | 7.196 | 564.9 | 382457 | AA069746 | HT383 | None |
| 6 | a05 | 4 | 1665.65 | 491.39 | 3980.278 | 3.39 | 1174.26 | 203939 | H56754 | NA | None |
| 1 | g03 | 3 | 1546.44 | 432.72 | 3980.199 | 3.574 | 1113.72 | 136255 | R33768 | HT3651 | HEMOGLOBIN BETA CHAIN |
| 3 | k15 | 3 | 1228.63 | 291.89 | 3942.82 | 4.209 | 936.73 | 147862 | R81846 | NA | FERRITIN LIGHT CHAIN |
| 3 | c07 | 1 | 455.31 | 49.42 | 3739.587 | 9.213 | 405.89 | 112471 | T85895 | NA | PROLIFERATION-ASSOCIATED PROTEIN PAG |
| 3 | b04 | 4 | 385.33 | 38.79 | 3442.657 | 9.934 | 346.54 | 186852 | R88127 | NA | None |

-continued

Database 1

| Field | Pos | Pat | File A | File B | Score | Ratio | Intensity | Clone ID | GBACC | Unigene | Identity |
|---|---|---|---|---|---|---|---|---|---|---|---|
| 3 | g13 | 7 | 339.05 | 12.77 | 3262.47 | 9.999 | 326.28 | 66599 | T67128 | HT2167 | ARYLAMINE N-ACETYL-TRANSFERASE, MONOMORPHIC |
| 1 | g10 | 5 | 537.75 | 82.91 | 2950.05 | 6.486 | 454.84 | 213151 | H70584 | NA | None |
| 3 | h12 | 3 | 373.26 | 42.41 | 2912.46 | 8.803 | 330.86 | 151792 | H03041 | NA | None |
| 3 | i04 | 2 | 1628.21 | 597.02 | 2812.278 | 2.727 | 1031.19 | 33453 | R19586 | HT3628 | MYELIN PROTEOLIPID PROTEIN |
| 2 | g15 | 4 | 4294.23 | 2602.04 | 2792.672 | 1.65 | 1692.19 | 166445 | R88586 | NA | None |
| 6 | b12 | 6 | 460.03 | 65.19 | 2785.896 | 7.056 | 394.84 | 23783 | T77328 | NA | None |
| 5 | l14 | 3 | 488.38 | 75.53 | 2669.285 | 6.466 | 412.84 | 44756 | H06950 | NA | CE00977 CHROMOSOME SEGREGATION PROTEIN |
| 3 | k10 | 5 | 2017.51 | 883.08 | 2591.77 | 2.285 | 1134.44 | 239053 | H68587 | NA | None |
| 5 | p11 | 4 | 1789.44 | 733.95 | 2573.41 | 2.438 | 1055.5 | 202302 | H52973 | NA | None |
| 3 | h06 | 5 | 507.47 | 84.77 | 2530.475 | 5.987 | 422.69 | 241545 | H90605 | NA | None |
| 3 | e01 | 5 | 1521.92 | 573.12 | 2519.566 | 2.656 | 948.8 | 233993 | H66198 | NA | None |
| 5 | d18 | 6 | 316.53 | 35.38 | 2515.081 | 8.946 | 281.15 | 298508 | W0482 | HT2858 | HEMOGLOBIN ALPHA CHAIN |
| 5 | g16 | 3 | 468.65 | 75.17 | 2452.79 | 6.234 | 393.47 | 162918 | H26802 | NA | None |
| 3 | o20 | 1 | 926.68 | 266.35 | 2297.484 | 3.479 | 660.34 | 114073 | T79540 | NA | None |
| 4 | a07 | 2 | 3007.71 | 1711.9 | 2276.655 | 1.757 | 1295.81 | 36318 | R21064 | NA | None |
| 3 | b14 | 7 | 623.27 | 136.11 | 2230.936 | 4.579 | 487.17 | 328920 | W45464 | NA | None |
| 3 | n06 | 5 | 357.25 | 50.7 | 2159.945 | 7.046 | 306.54 | 241976 | H93930 | HT2857 | HEMOGLOBIN ALPHA CHAIN |
| 4 | l23 | 1 | 1003.93 | 326.22 | 2085.655 | 3.077 | 677.71 | 120173 | T95693 | NA | None |
| 5 | k16 | 6 | 435.12 | 75.65 | 2067.536 | 5.752 | 359.47 | 296258 | W03125 | NA | None |
| 1 | e10 | 8 | 397.18 | 64.08 | 2064.729 | 6.198 | 333.11 | 376888 | AA046832 | HT2833 | HUMAN P04271 S-100 PROTEIN, BETA CHAIN |
| 3 | e02 | 5 | 1285.12 | 499.24 | 2022.967 | 2.574 | 785.88 | 238413 | H64769 | NA | None |
| 5 | l03 | 4 | 1188.58 | 445.69 | 1981.149 | 2.667 | 742.89 | 201839 | R99977 | NA | None |
| 3 | a23 | 4 | 475.12 | 92.02 | 1978.202 | 5.164 | 383.1 | 178867 | H49853 | NA | INTERFERON-INDUCIBLE PROTEIN 9-27 |
| 6 | n01 | 4 | 1682.83 | 784.43 | 1927.326 | 2.145 | 898.4 | 208017 | H62616 | NA | A49098 N-HYDROXY-ARYLAMINE SULFO-TRANSFERASE, HAST-I |
| 6 | j20 | 8 | 707.27 | 192.25 | 1894.728 | 3.679 | 515.02 | 68791 | T53417 | NA | None |

| Field | Pos | Pat | File A | File B | Score | Ratio | Intensity | Clone ID | GBACC | Unigene | Identity |
|---|---|---|---|---|---|---|---|---|---|---|---|
| 3 | a077 |  | 29787.66 | 6274.97 | 111616.33 | 4.747 | 23512.7 | 60267 | T40473 | H111572 | Human rearranged immunoglobulin lambda light chain mRNA |
| 2 | a184 |  | 10238.67 | 1206.6 | 76642.77 | 8.486 | 9032.08 | 171864 | H19169 | None | Soares adult brain N2b5HB55Y; EST |
| 4 | f065 |  | 12214.14 | 3268.24 | 33432.73 | 30737 |  | 8945.89 | 248425 | N78171 | 108896 | EST; highly similar to LAMBDA-CRYSTALLIN |
| 3 | a197 |  | 33237.82 | 17809.8 | 28792.62 | 1.886 | 15427.97 | 73163 | T56622 | 22024 | Transthyretin (prealbumin, amyloidosis type I) |
| 3 | h178 |  | 17668.78 | 7056.16 | 26574.23 | 2.504 | 10612.62 | 429711 | AA011711 | 22024 | Transthyretin (prealbumin, amyloidosis type I) |
| 2 | a172 |  | 7979.7 | 2113.99 | 22141.41 | 3.775 | 5865.72 | 28218 | R13309 | 7195 | Gamma-aminobutyric acid A receptor, gamma 2 |
| 3 | h167 |  | 10411.45 | 3452.6 | 20984.75 | 3.016 | 6958.86 | 328377 | W38364 | 107402 | EST; pancreatic islet Homo sapiens cDNA clone |
| 3 | a177 |  | 21456.68 | 10998.5 | 20402.52 | 1.951 | 10458.16 | 67221 | T52674 | 235 | Fms-related tyrosine kinase1; vascular endothelial growth factor |
| 4 | l234 |  | 38879.97 | 26384.3 | 18413.45 | 1.474 | 12495.58 | 195352 | R89536 | 22024 | Transthyretin (prealbumin, amyloidosis type I) |
| 3 | a213 |  | 8576.9 | 2876.75 | 16994.74 | 2.981 | 5700.15 | 146832 | R80470 | 75929 | Cadherin 11 |
| 3 | d107 |  | 3279.98 | 576.87 | 15369.43 | 5.686 | 2703.11 | 324801 | W47197 | 34359 | Soares senescent fibroblasts; EST |
| 4 | a072 |  | 17808.39 | 10904.3 | 11275.39 | 1.633 | 6904.07 | 36318 | R21064 | 29860 | Soares infant brain; EST |
| 4 | n044 |  | 6204.53 | 2269.68 | 10756.54 | 2.734 | 3934.85 | 197281 | R86898 | 124837 | Soares fetal liver spleen; EST |
| 2 | h153 |  | 8546.1 | 3807.22 | 10637.41 | 2.245 | 4738.88 | 144221 | R76995 | 119909 | Hemoglobin, beta |
| 4 | i154 |  | 11278.61 | 5949.95 | 10100.93 | 1.896 | 5328.67 | 191938 | H38896 | 20084 | Homo sapiens clone 23792 mRNA sequence |
| 1 | g033 |  | 6269.59 | 2554.69 | 9116.87 | 2.454 | 3714.89 | 136255 | R33768 | 64797 | Amyloid beta (A4) precursor-like protein 2 |
| 5 | h216 |  | 4063.07 | 1255.16 | 9089.46 | 3.237 | 2807.91 | 297148 | W03961 | None | Soares fetal liver spleen; EST |
| 2 | g154 |  | 12005.53 | 6860.26 | 9004.28 | 1.75 | 5145.27 | 166445 | R88586 | None | Soares adult brain; EST |
| 1 | n213 |  | 4323.6 | 1447.68 | 8589.07 | 2.987 | 2875.91 | 139543 | R62231 | 78224 | Ribonuclease, RNase A family 1 (pancreatic) |
| 2 | p144 |  | 9978.43 | 5421.15 | 8388.35 | 1.841 | 4557.28 | 178599 | H49130 | None | Soares adult brain; EST |
| 3 | i042 |  | 7244.96 | 3398.89 | 8198.13 | 2.132 | 3846.07 | 33453 | R19586 | 1787 | Myelin proteolipid protein |
| 3 | c155 |  | 6746.22 | 3297.81 | 7054.27 | 2.046 | 3448.4 | 233938 | H66535 | 75573 | Centromere protein E |
| 5 | l167 |  | 709.48 | 30.37 | 6790.47 | 9.999 | 679.11 | 567007 | AA152409 | 1034 | FK506-Binding protein precursor |
| 6 | a054 |  | 6128.69 | 3005.33 | 6369.39 | 2.039 | 3123.36 | 203939 | H56754 | None | Soares fetal liver spleen; EST |
| 3 | c156 |  | 1042.88 | 148.25 | 6293.1 | 7.034 | 894.63 | 279519 | N45619 | None | Soares multiple sclerosis 2NbHMSP vector |
| 5 | l165 |  | 7495.31 | 4222.39 | 5809.88 | 1.775 | 3272.92 | 258673 | N57334 | None | Soares placant 8 to 9 weeks; EST |
| 2 | g153 |  | 1441.09 | 289.81 | 5724.69 | 4.972 | 1151.28 | 141700 | R69677 |  |  |

-continued

| | | | | | | | | Database 1 | | |
|---|---|---|---|---|---|---|---|---|---|---|
| 6 | o242 | 2972.07 | 1017.3 | 5710.89 | 2.922 | 1954.76 | 133065 | R26331 | 74470 | Annexin II (lipocortin II) |
| 4 | e114 | 5444.64 | 2683.03 | 5604.1 | 2.029 | 2761.61 | 191516 | H38147 | None | Soares fetal liver spleen; EST |
| 2 | b157 | 1431.7 | 307.31 | 5238.49 | 4.659 | 1124.4 | 325121 | W49891 | 1940 | Crystallin, alpha B |
| 5 | l038 | 656.88 | 77.33 | 4922.82 | 8.494 | 579.55 | 490976 | AA136785 | None | Soares pregnant uterus NbHPU *Homo sapiens* cDNA clone |
| 5 | e063 | 4562.62 | 2217.18 | 4826.59 | 2.058 | 2345.45 | 162526 | H28534 | 74602 | Aquaporin-Chip |
| 3 | e015 | 2697.04 | 973.47 | 4775.22 | 2.771 | 1723.57 | 233993 | H66198 | None | Soares fetal liver spleen; EST |
| 3 | a218 | 1190.06 | 240.79 | 4691.46 | 4.942 | 949.26 | 418242 | W90242 | 15106 | EST; similar to hypothetical 17.1 kD protein in Sah1-Mei4 intergenic region |
| 4 | k111 | 4785.04 | 2447.09 | 4571.64 | 1.955 | 2337.95 | 116427 | T91421 | 12749 | Soares fetal liver spleen; EST |
| 3 | h245 | 5884.03 | 3425.95 | 4221.7 | 1.717 | 2458.07 | 241622 | H89823 | 14912 | *Homo sapiens* mRNA for KIAA0286 gene; Soares fetal liver spleen; EST |
| 4 | a081 | 6827.39 | 4229.02 | 4194.84 | 1.614 | 2598.37 | 116797 | T89571 | 106134 | Soares fetal liver spleen; EST |
| 4 | l232 | 1775.94 | 530.7 | 4167.06 | 3.346 | 1245.24 | 39167 | R54351 | 12773 | *Homo sapiens* mRNA for pristanoyl-CoA oxidase |
| 5 | p118 | 1303.92 | 315.21 | 4089.97 | 4.137 | 988.71 | 491209 | AA150295 | 17882 | Soares pregnant uterus NbHPU *Homo sapiens* cDNA clone |
| 1 | o017 | 1960.87 | 637.89 | 4066.8 | 3.074 | 1322.98 | 308548 | W24939 | 1477 | Insuline-like growth factor binding protein 6 |
| 3 | e025 | 1946.39 | 631.88 | 4049.14 | 3.08 | 1314.52 | 238413 | H64769 | None | *Homo sapiens* clone; library of Weizmann olfactory epithelium |
| 2 | j124 | 6077.39 | 3655.5 | 4026.47 | 1.663 | 2421.89 | 177794 | H46054 | 133528 | Soares adult brain; EST |
| 3 | l205 | 4733.41 | 2574.49 | 3969.33 | 1.839 | 2158.91 | 241953 | H93923 | 6940 | *Homo sapiens* mRNA for retro-transposon |
| 3 | a191 | 1337.1 | 340.69 | 3910.6 | 3.925 | 996.41 | 112442 | T85875 | None | Soares fetal liver spleen; EST |
| 1 | e093 | 1295.1 | 325.33 | 3860.47 | 3.981 | 969.76 | 136049 | R35560 | None | Soares placenta; EST |
| 5 | e128 | 5881.32 | 3556.59 | 3844.26 | 1.654 | 2324.73 | 489404 | AA045613 | 37012 | Corticosteroid 11-beta-dehydrogenase, isozyme 1 |
| 5 | i033 | 2489.39 | 984.88 | 3802.86 | 2.528 | 1504.52 | 161077 | H26360 | None | Soares breast; EST; possible GTP-binding protein HSR1 (human) |
| 3 | p074 | 1277.7 | 323.61 | 3767.08 | 3.948 | 954.1 | 186766 | H50621 | 134156 | Soares breast; EST |
| 5 | h217 | 40072 | 28.86 | 3718.18 | 9.999 | 371.86 | 545626 | AA078832 | 108102 | Cytochrome B561 |
| 4 | k132 | 1465.95 | 426.1 | 3577.53 | 3.44 | 1039.86 | 36786 | R33416 | 21035 | Soares infant brain; EST |
| 3 | e107 | 1075.28 | 250.54 | 3539.58 | 4.292 | 824.73 | 78546 | T60417 | None | from Stratagene liver library; similar to apolipoprotein A-1 precursor |
| 3 | k162 | 3329.65 | 1641 | 3426.33 | 2.029 | 1688.65 | 34165 | R20019 | None | Soares infant brain; EST |
| 6 | a057 | 351.93 | 31.04 | 3208.51 | 9.999 | 320.88 | 590421 | AA147990 | 76194 | Ribosomal protein S5 |
| 6 | a058 | 831.42 | 172.09 | 3185.36 | 4.831 | 659.33 | 502299 | AA156840 | 248 | Proto-oncogene c-cot (protein-serine/threonine kinase) |
| 5 | b233 | 4693.32 | 2811.7 | 3140.84 | 1.669 | 1881.63 | 43337 | H13009 | 21466 | Soares infant brain; EST; Human Aac11 mRNA, complete cds |
| 4 | g117 | 2723.6 | 1271.45 | 3110.67 | 2.142 | 1452.15 | 345607 | W72046 | 54886 | Soares fetal heart; EST |
| 3 | a214 | 923.74 | 213.66 | 3069.92 | 4.323 | 710.08 | 178860 | H49751 | None | Soares adult brain; EST; 5' end is similar to MSR1 repetitive element |
| 2 | a192 | 5126.25 | 3208.52 | 3063.97 | 1.598 | 1917.74 | 28221 | R13404 | None | Soares infant brain; EST |
| 2 | b205 | 2089.01 | 861.17 | 2978.49 | 2.426 | 1227.84 | 232461 | H95908 | None | Soares pineal gland; EST |
| 5 | a224 | 1394.97 | 447.25 | 2955.97 | 3.119 | 947.12 | 199370 | R97323 | 85927 | Tissue inhibitor of metallo-proteinase 3 |
| 2 | i087 | 2501.93 | 1157.32 | 2906.85 | 2.162 | 1344.62 | 324356 | W47664 | 80706 | NAD(P)H: menadione oxidoreductase |
| 3 | c071 | 1332.36 | 420.53 | 2888.88 | 3.168 | 911.82 | 112471 | T85895 | 1163 | Proliferation-associated gene A |
| 5 | e124 | 840.88 | 190.35 | 2873.71 | 4.417 | 650.53 | 200031 | R97154 | None | Soares fetal liver spleen; EST |
| 1 | e098 | 1219 | 365.31 | 2848.71 | 3.337 | 853.69 | 366903 | AA026304 | 20943 | Soares fetal heart; EST |
| 5 | b236 | 745.1 | 154.8 | 2841.26 | 4.813 | 590.3 | 296664 | W02194 | None | Soares fetal liver spleen; EST |
| 3 | o074 | 1148.1 | 335.2 | 2784.28 | 3.425 | 812.9 | 179922 | H51007 | 89655 | *Homo sapiens* tyrosine phosphatase (IA-2/PTP) mRNA |
| 2 | a186 | 915.06 | 226.55 | 2780.91 | 4.039 | 688.51 | 275942 | R93869 | 66378 | Soares retina; EST |
| 1 | b201 | 1064.65 | 297.27 | 2748.33 | 3.581 | 767.38 | 24608 | T80490 | 13512 | Human protein ZW10 homolog (HZW10) mRNA |
| 3 | b126 | 4674.26 | 2950.22 | 2731.54 | 1.584 | 1724.05 | 286050 | N64281 | 48742 | Morton fetal cochlea; EST |
| 5 | l162 | 983.41 | 264.12 | 2678.26 | 3.723 | 719.3 | 37720 | R59435 | None | Soares infant brain; EST |
| 3 | o193 | 4601.61 | 2916.69 | 2658.27 | 1.578 | 1684.92 | 14825 | H12367 | 119499 | Hemoglobin, beta |
| 1 | o087 | 764.02 | 171.17 | 2646.33 | 4.464 | 592.86 | 310622 | W31182 | 109819 | Soares senescent fibroblasts; EST |
| 3 | h171 | 846.52 | 206.41 | 2625.1 | 4.101 | 640.1 | 114411 | T78159 | 76536 | Hs mRNA for transducin-like protein; similar to guanine nucleotide binding protein |
| 2 | b146 | 1370.01 | 478.86 | 2551.2 | 2.826 | 891.35 | 278269 | N94916 | 118779 | 60S ribosomal protein L24 |
| 2 | m184 | 824.37 | 201.38 | 2550.24 | 4.094 | 622.99 | 172893 | H20448 | 31748 | Hs mRNA for TRE5 |
| 2 | a212 | 9833.36 | 7814.74 | 2540.05 | 1.258 | 2018.62 | 28225 | R13406 | None | Soares infant brain; EST |
| 1 | g037 | 869.37 | 222.08 | 2533.81 | 3.915 | 647.28 | 308013 | W24494 | 19399 | Soares fetal lung; EST |
| 6 | j188 | 5578.44 | 3851.84 | 2500.54 | 1.448 | 1726.59 | 22478 | T74342 | None | Soares infant brain; EST |
| 2 | g156 | 1349.09 | 476.61 | 2469.62 | 2.831 | 872.48 | 274375 | H49806 | 35750 | Human chromosome 16 BAC clone CIT987SK-A-962B4 |
| 1 | n088 | 1230.4 | 419.22 | 2380.86 | 2.935 | 811.19 | 382989 | AA084560 | 76152 | Decorin; similar to bone proteoglycan II precursor |
| 6 | a056 | 559.62 | 106.62 | 2377.64 | 5.249 | 453 | 299666 | W05763 | 77208 | Soares fetal lung; EST |
| 3 | d161 | 4618.76 | 3053.64 | 2367.33 | 1.513 | 1565.13 | 114926 | T86234 | None | Soares fetal liver spleen; EST |

-continued

Database 1

| | | | | | | | | | |
|---|---|---|---|---|---|---|---|---|---|
| 3 | c061 | 575.21 | 112.59 | 2363.34 | 5.109 | 462.62 | 113547 | T79234 | None | Soares fetal liver spleen; EST |
| 3 | a195 | 1148.21 | 390.65 | 2226.64 | 2.939 | 757.56 | 233826 | H64619 | 138557 | Soares fetal liver spleen; EST |
| 3 | p077 | 768.87 | 197.47 | 2224.76 | 3.894 | 571.4 | 324213 | W47502 | 76847 | Human mRNA for KIAA0088 gene |
| 4 | k131 | 7404.01 | 5699.52 | 2214.23 | 1.299 | 1704.49 | 116431 | T91423 | 16804 | Soares fetal liver spleen; EST |
| 5 | c124 | 2689.03 | 1513.31 | 2089.15 | 1.777 | 1175.72 | 199641 | R96571 | 33433 | Soares fetal liver spleen; EST |
| 3 | a064 | 570.23 | 122.91 | 2075.13 | 4.639 | 447.31 | 180285 | R85333 | None | Similar to cytochron C oxidase polypeptide IV precursor |
| 3 | d187 | 1400.26 | 568.43 | 2049.1 | 2.463 | 831.83 | 328947 | W45482 | 30925 | Pancreatic islet Hs cDNA clone; EST |
| 2 | i076 | 1040.39 | 354.13 | 2016.18 | 2.938 | 686.27 | 274408 | H49897 | 93814 | Soares fetal liver spleen; EST; weakly similar to M01F1.6 |
| 6 | m243 | 9144.65 | 7517.06 | 1979.98 | 1.217 | 1627.58 | 47171 | H10763 | 21448 | Soares infant brain; EST |
| 5 | k175 | 738.48 | 201.02 | 1974.49 | 3.674 | 537.46 | 251637 | H96724 | 81988 | Human mitogen-responsive phosphoprotein (DOC-2) mRNA |
| 3 | c096 | 1998.95 | 1008.36 | 1963.7 | 1.982 | 990.58 | 279481 | N45602 | None | Soares multiple sclerosis; EST |
| 5 | l034 | 3385.63 | 2153.51 | 1937.07 | 1.572 | 1232.12 | 201839 | R99977 | 108048 | Soares fetal liver spleen; EST; weakly similary to line-1 protein ORF2 (Hs) |
| 2 | o135 | 2000.18 | 1022.05 | 1914.2 | 1.957 | 978.12 | 223092 | H86650 | 33687 | Soares retina; EST; contains LTR5 repetitive element; similar to Alu repetitive element |
| 2 | n232 | 2028.18 | 1044.69 | 1909.35 | 1.941 | 983.48 | 31546 | R20842 | 23075 | Soares infant brian; EST; similar to Alu repetitive element |
| 1 | p037 | 1521.81 | 676.29 | 1902.59 | 2.25 | 845.51 | 321259 | W55913 | 76317 | Ribosomal protein L31 |
| 5 | b237 | 366.83 | 59.86 | 1880.87 | 6.127 | 306.96 | 531514 | AA074032 | 83848 | Triosephosphate isomerase 1 |
| 3 | a216 | 623.41 | 155.24 | 1880.14 | 4.016 | 488.18 | 279374 | N45540 | 138692 | Soares multiple sclerosis; EST; similar to retrovirus-related envelope protein |
| 6 | l246 | 1661.35 | 779.4 | 1879.94 | 2.132 | 881.95 | 306904 | W21392 | None | Soares fetal lung; EST; contains Alu repetitive element |

Example 12

Analyses of Elastin Distribution in the Macula with Age and AMD

We examined the reactivity of rabbit polyclonal anti-aortic elastin antibodies with the elastic layer of Bruch's membrane in a small series of young (<5 years), middle-aged (20–40 years), and AMD (>50 years) donors. The sixty-three human donor eyes employed in this study were obtained from The University of Iowa Lions Eye Bank (Iowa City, Iowa) within four hours of death. Institutional Review Board committee approval for the use of human donor tissues was obtained from the Human Subjects Committee at The University of Iowa. Posterior poles, or wedges of posterior poles spanning between the ora serrata and macula, were fixed in 4% (para)formaldehyde in 100 mM sodium cacodylate, pH 7.4. After 2–4 hours of fixation, eyes were transferred to 100 mM sodium cacodylate and were rinsed (3×10 min), infiltrated, and embedded in acrylamide. These tissues were subsequently embedded in OCT, snap frozen in liquid nitrogen, and stored at −80° C. Unfixed posterior poles, or wedges thereof, were embedded directly in OCT, without acrylamide infiltration or embedment. Both fixed and unfixed tissues were sectioned to a thickness of 6–8?m on a cryostat. The presence and type(s) of drusen were documented on adjacent sections stained with hematoxylin/eosin, periodic acid Schiff reagent, and Sudan Black B (1% in 70% ethanol).

Immunolabeling was performed as described previously (32). Adjacent sections were incubated with secondary antibody alone, to serve as negative controls. Some immunolabeled specimens were viewed by confocal laser scanning microscopy, as described previously (42). The elastic layer in the macula differed significantly from that in extramacular regions in all three groups. Immunoreactive elastin was thin and highly fragmented in the macula of AMD donors, as compared to the peripheral region where it was contiguous and thick. Immunoreactive elastin was absent in the maculas of the two young donors examined. We suggest that these observations provide a significant clue as to why the macula may be particularly susceptible to degeneration.

Example 13

Assessment of Serum Autoantibodies in AMD

The rationale for conducting this subaim is based upon the hypothesis that dendritic cells may be activated by local tissue injury and that this might result in the initiation of an autoimmune response to retinal and/or RPE antigens that are uncovered during tissue damage or chronic inflammation. This event could occur as a consequence of an aberrant delayed-type hypersensitivity response, explaining previous observations of serum autoantibodies in some AMD patients. As such, this aim will be directed toward determining whether patients with AMD and ocular drusen have increased levels of specific autoantibodies when compared to controls without drusen. Particular attention will be paid to a potential relationship with AMD phenotypes, drusen status, and the "stage" of the disease. The identification of autoantibodies or mediators of chronic inflammation may serve as a means for the development of diagnostic assays for the identification of AMD.

Study Design: Visual acuity measurements, stereo macula photos, and peripheral photos will be taken at the beginning of the study and every six months thereafter. Blood and sera will be drawn when subjects enter the study and every 6–12 months thereafter. DNA will be prepared from a portion of each blood sample for future genetic studies. The presence of serum autoantibodies and immune complexes will be determined using standard protocols. In addition, sera will be reacted with tissue sections derived from donors with and without AMD, followed by a secondary antibody that has been adsorbed against human immunoglobulins. Western blots of retina/RPE/choroid from AMD and non-AMD donors will also be incubated with serum samples to identify specific bands against which autoantibodies react.

In addition, levels of the following proteins, additional indicators of autoantibody responses, chronic inflammation and/or acute phase responses, will be assayed by a clinical diagnostic laboratory. These will include Bence Jones protein, serum amyloid A, M components, C-reactive protein, mannan binding protein, serum amyloid A, C3a, C5a, other complement proteins, coagulation proteins, fibrinogen, vitronectin, CD25, interleukin 1, interleukin 6, and apolipoprotein E. Serum protein electrophoresis, lymphocyte transformation, sedimentation rate, and spontaneous, whole blood, white cell count will also be measured.

The presence of antibodies directed against the following proteins (many observed in other age-related conditions and/or MPGN) will also be determined: type IV collagen, glomerular basement membrane, neutrophils, cytoplasm (c-ANCA, p-ANCA), C3 convertase (C3 nephritic factor), alpha-1 anti-trypsin levels (decreased in MPGN), epsilon 4 allele, apolipoprotien E, GFAP, ANA, serum senescent cell antigen, S-100, type 2 plasminogen activator, alpha-1-antichymotrypsin, SP-40,40, endothelial cell, parietal cell, mitochondria, Jo-1, islet cell, inner ear antigen, epidermolysis Bullosa Acquista, endomysial IgA, cancer antigen 15-3, phospholipid, neuronal nucleus, cardiolipin, and ganglioside.

TABLE 6

Serological Tests for Immune-Mediated Processes

Autoimmune and Chronic Inflammation Cells:

Whole blood cell count, hemogram plus differential
CBC, hemogram.
Immunoglobulins:

Imunoglobulin A, G, M, D, E quatification
IgG subclass quantification
Kappa/lambda light chains- quantification and ratios
Miscellaneous Proteins:

Serum protein electrophoresis
Complement, total classical and alternative
Compement: C3, C4, C5 quantitative
Bence Jones proteins
M component
C reactive protein
Serum amyloid A
Coagulation proteins
Fibrinogen (and/or ESR)
Elastase inhibitors
Elastin and collagen peptide fragments
Serum beta-2-microglobulin
Serum carotine
Creatine kinase
Rheumatoid factor
C-reactive protein
Immunocompetent cells:

Lymphocyte immunophenotyping and absolute CD4 cell count.
Anti-OKT3, IgG antibodies.
CD34 Stem cell count.
CD3 cell count.
CD4 cell count.
Lymphocyte mitogen and antigen profile screen (LPA).
Lymphocyte antibody screen.
NK cells.
T and B-cell markers.
CD4/CD8 - absolute count and ratio.
HLA phenotyping, both class I and II. HLAB-27.

TABLE 6-continued

Serological Tests for Immune-Mediated Processes

Cytokines:

Interleukins
Fibroblast growth factor
Vasoactive intestinal peptide (VIP)
Autoantibodies:

Anti-nuclear antibody (ANA)
Anti-neutrophil cytoplasmic antibody (ANCA)
Double stranded DNA antibody
Anti-ribonuclear protein antibody
Scl-70 antibody
SM antibody
SS-A antibody (anti-RO) and SS-B (anti-LA) antibody
Anti-neuronal nuclear antibodies
Antineuronal nuclear antibody (Purkinje cells).
Jo-1 antibody
Paraneoplasctic antibody A
Anti-cardiolipin antibody
Anti-glomerular basement membrane antibodies
Mitochondrial antibody
Anti-ganglioside assay
Anti-Streptolysin-O screen
Anti-sulfatide antibody
Anti-Thyrocellular antibody
Antibody to inner ear antigen
Bullos pemphigoid antibodies
PM-1 antibody
Adrenal cortical antibody.
Liver-kidney microsomal antibody
Mitochondrial antibody
Parathyroid antibody
Parietal cell antibody
Pemphigus antibodies
Smooth muscle antibodies and striated muscle antibodies.
Islet cell antibodies
Lupus anticoagulant
Anti-viral and anti-bacterial antibodies:

CMV antibody
Group B strep antigen
Hepatitis B, E, C, A antibodies
Helicobacter Pylon antibodies
Antibodies to CMV, EB virus, Herpes Simplex, Measles, mycoplasma, Rubella, Varicella-Zoster
Others:

Cancer antigen 125
Cancer antigen 15-3
Carcinoembrionic antigen
Small fiber axonal profile
CNS serology battery
Sensorimotor neuropathy profile

We claim:

1. A method for assessing a subject's risk for age-related macular degeneration, comprising:
   (a) providing a blood sample from a subject to be tested for age-related macular degeneration; and
   (b) determining whether the sample has protein markers for abdominal aortic aneurysm (AAA), wherein
   a difference in the level of the protein markers relative to the level of the same marker in a control population comprising individuals that do not have AAA and/or age-related macular degeneration is an indication that the subject is at risk for age-related macular degeneration, wherein the protein markers for AAA are EDPs (elastin degradation products) and wherein the level of EDPs is elevated compared to the control population.

2. The method of claim 1, further comprising performing an ophthalmological procedure on the subject to detect a one or more characteristic(s) of macular degeneration, and wherein the characteristic is selected from a group consisting of drusen, choroidal neovascularization, a disciform scar, geographic atrophy, and abnormal pigmentation in the subject's eye; and detection of the characteristic is a further indication that the subject is at risk for macular degeneration.

3. The method of claim 1, wherein the protein marker for abdominal aortic aneurysm is detected by an immunological method.

4. The method of claim 1, wherein said macular degeneration is the exudative or neovascular (wet) form, which is characterized by disciform scars and/or choroidal neovascularization (DS/CNV) or an exudative precursor phenotype.

5. The method of claim 3, wherein determining comprises detecting said one or more protein markers by Western blot or ELISA.

6. The method of claim 1, wherein said subject is a mammal.

7. The method of claim 6, wherein said mammal is a human.

* * * * *

UNITED STATES PATENT AND TRADEMARK OFFICE
CERTIFICATE OF CORRECTION

| | | |
|---|---|---|
| PATENT NO. | : 7,108,982 B2 | Page 1 of 1 |
| APPLICATION NO. | : 09/511416 | |
| DATED | : September 19, 2006 | |
| INVENTOR(S) | : Gregory S. Hageman | |

It is certified that error appears in the above-identified patent and that said Letters Patent is hereby corrected as shown below:

Claim 2, column 113, line 40, replace "detect a one" with --detect one--.

Signed and Sealed this

Tenth Day of April, 2007

JON W. DUDAS
*Director of the United States Patent and Trademark Office*

SEQUENCE LISTING

<160> NUMBER OF SEQ ID NOS: 25

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:elastin
    degradation product (EDP)

<400> SEQUENCE: 1

Val Gly Val Ala Pro Gly
 1               5

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:RT-PCR
    primer

<400> SEQUENCE: 2
gtcgagatgc acacaagagt g                                               21

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:RT-PCR
    primer

<400> SEQUENCE: 3
tccttcagtt tactggagat cg                                              22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:RT-PCR
    primer

<400> SEQUENCE: 4
gccaggaata tgaacaagcc g                                               21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:RT-PCR
    primer

<400> SEQUENCE: 5
caaatcccca atctctccca c                                               21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:RT-PCR
    primer -continued

```
<400> SEQUENCE: 6
tgaacaccaa cttcttccac g                                              21

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:RT-PCR
      primer

<400> SEQUENCE: 7
ggcgacctca gtaattttct tg                                             22

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence:RT-PCR
      primer

<400> SEQUENCE: 8
ggtcgctttt gggattacc                                                 19

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:RT-PCR
      primer

<400> SEQUENCE: 9
ctccagttcc gatttgtagg c                                              21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:RT-PCR
      primer

<400> SEQUENCE: 10
gttcaagtca gaaaaggggc                                                20

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:RT-PCR
      primer

<400> SEQUENCE: 11
gtgtcttggt gaagtggatc tg                                             22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:RT-PCR
      primer

<400> SEQUENCE: 12
```

```
atggtatgtg gacgatcaag gc                                              22
```

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence:RT-PCR
      primer

<400> SEQUENCE: 13

```
tattgctcgg taaccttccc tg                                              22
```

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:RT-PCR
      primer

<400> SEQUENCE: 14

```
aatgagcccc tggagtgaat g                                               21
```

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence:RT-PCR
      primer

<400> SEQUENCE: 15

```
atgtcagagt gtttccatcc cg                                              22
```

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence:RT-PCR
      primer

<400> SEQUENCE: 16

```
gagcgagttc tacatcctaa cg                                              22
```

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence:RT-PCR
      primer

<400> SEQUENCE: 17

```
cacgaagtag gtgtccttga ag                                              22
```

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence:RT-PCR
      primer

<400> SEQUENCE: 18
agactggaac tacaaatgcc c                                         21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:RT-PCR
      primer

<400> SEQUENCE: 19
agattcagag tgccattgtc c                                         21

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence:RT-PCR
      primer
<221> NAME/KEY: modified_base
<222> LOCATION: (10)
<223> OTHER INFORMATION: i

<400> SEQUENCE: 20
acgtttgatn tccasyttgg tccc                                      24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence:RT-PCR
      primer
<221> NAME/KEY: modified_base
<222> LOCATION: (10)
<223> OTHER INFORMATION: i
<221> NAME/KEY: modified_base
<222> LOCATION: (16)
<223> OTHER INFORMATION: i

<400> SEQUENCE: 21
gamatyswgn atgacncagt ctcc                                      24

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence:RT-PCR
      primer

<400> SEQUENCE: 22
acctaracgg tsasctkggt ccc                                       23

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence:RT-PCR
      primer

<400> SEQUENCE: 23
tcytmtgwgc tgactcagsm cc                                        22

<210> SEQ ID NO 24
<211> LENGTH: 19

```
<212> TYPE: DNA
<213> ORGANISM: Artificial Sequence
<220> FEATURE:
<223> OTHER INFORMATION: Description of Artificial Sequence:RT-PCR
      primer

<400> SEQUENCE: 24
gggctggatg aggactcag                                                    19

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:RT-PCR
      primer

<400> SEQUENCE: 25
aaggcaacag gcttcttcag                                                   20
```